US010022503B2

(12) United States Patent
Julian et al.

(10) Patent No.: US 10,022,503 B2
(45) Date of Patent: Jul. 17, 2018

(54) REMOVAL OF NEEDLE SHIELD FROM SYRINGES AND AUTOMATIC INJECTION DEVICES

(71) Applicants: AbbVie Biotechnology Ltd, Hamilton (BM); Elcam Medical Agricultural Cooperative Association Ltd., Kibbutz Bar-Am (IL)

(72) Inventors: Joseph F. Julian, Libertyville, IL (US); Chuan Li, Deerfield, IL (US); Philip D. Anderson, Libertyville, IL (US); Linas P. Laurusonis, Gurnee, IL (US); Lior Raday, D.n. Ashkelon (IL); Ehud Carmel, Ganey Tikva (IL); Lior Marli, Rehovot (IL); David Daily, Herzelia (IL); Guy Keenan, Tel Aviv-Jaffa (IL)

(73) Assignees: AbbVie Biotechnology Ltd, Hamilton (BM); Elcam Medical Agricultural Cooperative Association Ltd, Kibbutz Bar-Am (IL)

( * ) Notice: Subject to any disclaimer, the term of this patent is extended or adjusted under 35 U.S.C. 154(b) by 138 days.

(21) Appl. No.: 15/094,364

(22) Filed: Apr. 8, 2016

(65) Prior Publication Data

US 2016/0220765 A1 Aug. 4, 2016

Related U.S. Application Data

(63) Continuation of application No. 14/253,348, filed on Apr. 15, 2014, now Pat. No. 9,339,610, which is a
(Continued)

(51) Int. Cl.
*A61M 5/32* (2006.01)
*A61M 5/20* (2006.01)

(52) U.S. Cl.
CPC ............ *A61M 5/3204* (2013.01); *A61M 5/20* (2013.01); *A61M 5/32* (2013.01); *A61M 5/321* (2013.01);
(Continued)

(58) Field of Classification Search
CPC ........ A61M 2205/581; A61M 2207/00; A61M 5/20; A61M 5/32; A61M 5/3204; A61M 5/321; Y10T 29/49826; Y10T 29/53
See application file for complete search history.

(56) References Cited

U.S. PATENT DOCUMENTS 2,398,544 A 4/1946 Lockhart
2,459,875 A 1/1949 Folkman
(Continued)

FOREIGN PATENT DOCUMENTS

DE 2019296 A1 11/1971
DE 19821933 C1 11/1999
(Continued)

OTHER PUBLICATIONS

Owen Mumford drawing/schematic B of the Plunger-Miniject dated Sep. 5, 1997, Drawing No. AJ 654.
(Continued)

*Primary Examiner* — Quynh-Nhu H Vu
(74) *Attorney, Agent, or Firm* — McCarter & English, LLP; David R. Burns

(57) ABSTRACT

Exemplary embodiments provide a needle shield remover that reliably engages with a distal cap of an automatic injection device and with one or more needle shields coupled to a syringe of the device. When a user removes the distal cap, the needle shield remover reliably removes the needle shields (e.g., a soft needle shield and a rigid needle shield) from the syringe, thereby exposing the injection needle for performing an injection. In an exemplary assem-
(Continued)

bly method, a needle shield remover is engaged to a needle shield coupled to a syringe, prior to insertion of the syringe and needle shield remover assembly into a housing of the device. This exemplary assembly method allows visual inspection, outside the housing of the device, to ensure that the needle shield remover is correctly and reliably engaged to the needle shield before the syringe and needle shield remover assembly is inserted into the housing.

30 Claims, 30 Drawing Sheets

Related U.S. Application Data continuation of application No. 13/357,508, filed on Jan. 24, 2012, now Pat. No. 8,708,968.

(60) Provisional application No. 61/435,467, filed on Jan. 24, 2011.

(52) U.S. Cl.
CPC ... *A61M 2205/581* (2013.01); *A61M 2207/00* (2013.01); *Y10T 29/49826* (2015.01); *Y10T 29/53* (2015.01)

(56) References Cited

U.S. PATENT DOCUMENTS

| | | |
|---|---|---|
| 2,565,081 A | 8/1951 | Maynes |
| 2,591,457 A | 4/1952 | Maynes |
| 2,701,566 A | 2/1955 | Krug |
| 2,752,918 A | 7/1956 | Uytenbogaart |
| 2,832,339 A | 4/1958 | Sarnoff et al. |
| 2,888,924 A | 6/1959 | Dunmire |
| 2,960,087 A | 11/1960 | Uytenbogaart |
| 3,051,173 A | 8/1962 | Johnson et al. |
| 3,055,362 A | 9/1962 | Uytenbogaart |
| 3,066,670 A | 12/1962 | Stauffer |
| 3,136,313 A | 6/1964 | Enstrom et al. |
| 3,314,428 A | 4/1967 | Johnson et al. |
| 3,330,279 A | 7/1967 | Sarnoff et al. |
| 3,403,680 A | 10/1968 | Sinclair et al. |
| 3,543,603 A | 12/1970 | Gley |
| 3,605,743 A | 9/1971 | Arce |
| 3,618,603 A | 11/1971 | Levenson |
| 3,702,609 A | 11/1972 | Steiner |
| 3,712,301 A | 1/1973 | Sarnoff |
| 3,742,948 A | 7/1973 | Post et al. |
| 3,797,488 A | 3/1974 | Hurschman et al. |
| 3,797,489 A | 3/1974 | Sarnoff |
| 3,882,863 A | 5/1975 | Sarnoff et al. |
| 3,892,237 A | 7/1975 | Steiner |
| 3,910,260 A | 10/1975 | Sarnoff et al. |
| 3,941,130 A | 3/1976 | Tibbs |
| 4,004,577 A | 1/1977 | Sarnoff |
| 4,031,893 A | 6/1977 | Kaplan et al. |
| 4,106,770 A | 8/1978 | Gray |
| 4,178,928 A | 12/1979 | Tischlinger |
| 4,202,314 A | 5/1980 | Smirnov et al. |
| 4,214,584 A | 7/1980 | Smirnov et al. |
| 4,226,235 A | 10/1980 | Sarnoff et al. |
| 4,258,713 A | 3/1981 | Wardlaw |
| 4,261,358 A | 4/1981 | Vargas et al. |
| 4,275,729 A | 6/1981 | Silver et al. |
| 4,394,863 A | 7/1983 | Bartner |
| 4,425,120 A | 1/1984 | Sampson et al. |
| 4,437,859 A | 3/1984 | Whitehouse et al. |
| 4,447,231 A | 5/1984 | Bekkering |
| 4,530,695 A | 7/1985 | Phillips et al. |
| 4,565,543 A | 1/1986 | Bekkering et al. |
| 4,573,976 A | 3/1986 | Sampson et al. |
| 4,578,064 A | 3/1986 | Sarnoff et al. |
| 4,624,660 A | 11/1986 | Mijers et al. |
| 4,637,403 A | 1/1987 | Garcia et al. |
| 4,664,653 A | 5/1987 | Sagstetter et al. |
| 4,678,461 A | 7/1987 | Mesa |
| 4,689,042 A | 8/1987 | Sarnoff et al. |
| 4,723,937 A | 2/1988 | Sarnoff et al. |
| 4,755,169 A | 7/1988 | Sarnoff et al. |
| 4,795,432 A | 1/1989 | Karczmer |
| 4,795,433 A | 1/1989 | Sarnoff |
| 4,820,286 A | 4/1989 | van der Wal |
| 4,822,340 A | 4/1989 | Kamstra |
| 4,850,994 A | 7/1989 | Zerbst et al. |
| 4,852,768 A | 8/1989 | Bartsch |
| 4,902,279 A | 2/1990 | Schmidtz et al. |
| 4,923,447 A | 5/1990 | Morgan |
| 4,927,416 A | 5/1990 | Tomkiel |
| 4,929,237 A | 5/1990 | Medway |
| 4,955,868 A | 9/1990 | Klein |
| 4,964,866 A | 10/1990 | Szwarc |
| 4,966,592 A | 10/1990 | Burns et al. |
| 4,994,034 A | 2/1991 | Botich et al. |
| 5,041,088 A | 8/1991 | Ritson et al. |
| 5,042,977 A | 8/1991 | Bechtold et al. |
| 5,049,133 A | 9/1991 | Villen Pascual |
| D322,479 S | 12/1991 | Miyaguchi |
| 5,085,641 A | 2/1992 | Sarnoff et al. |
| 5,085,642 A | 2/1992 | Sarnoff et al. |
| 5,092,842 A | 3/1992 | Bechtold et al. |
| 5,092,843 A | 3/1992 | Monroe et al. |
| 5,102,393 A | 4/1992 | Sarnoff et al. |
| 5,104,380 A | 4/1992 | Holman et al. |
| 5,114,406 A | 5/1992 | Gabriel et al. |
| 5,114,410 A | 5/1992 | Caralt Batlle |
| 5,137,516 A | 8/1992 | Rand et al. |
| 5,163,918 A | 11/1992 | Righi et al. |
| 5,201,708 A | 4/1993 | Martin |
| 5,224,936 A | 7/1993 | Gallagher |
| 5,242,240 A | 9/1993 | Gorham |
| 5,244,465 A | 9/1993 | Michel |
| 5,259,840 A | 11/1993 | Boris |
| 5,263,934 A | 11/1993 | Haak |
| 5,267,963 A | 12/1993 | Bachynsky |
| 5,267,972 A | 12/1993 | Anderson |
| 5,267,976 A | 12/1993 | Guerineau et al. |
| 5,273,544 A | 12/1993 | van der Wal |
| D343,897 S | 2/1994 | Rand et al. |
| 5,295,965 A | 3/1994 | Wilmot |
| 5,295,975 A | 3/1994 | Lockwood, Jr. |
| 5,298,024 A | 3/1994 | Richmond |
| D346,219 S | 4/1994 | Fardigh |
| 5,300,030 A | 4/1994 | Crossman et al. |
| 5,318,538 A | 6/1994 | Martin |
| 5,320,609 A | 6/1994 | Haber et al. |
| 5,334,144 A | 8/1994 | Alchas et al. |
| 5,342,308 A | 8/1994 | Boschetti |
| 5,346,480 A | 9/1994 | Hess et al. |
| 5,358,489 A | 10/1994 | Wyrick |
| 5,376,080 A | 12/1994 | Petrussa |
| 5,378,233 A | 1/1995 | Haber et al. |
| 5,383,865 A | 1/1995 | Michel |
| 5,391,151 A | 2/1995 | Wilmot |
| 5,425,715 A | 6/1995 | Dalling et al. |
| 5,433,712 A | 7/1995 | Stiles et al. |
| 5,478,316 A | 12/1995 | Bitdinger et al. |
| 5,480,387 A | 1/1996 | Gabriel et al. |
| 5,531,705 A | 7/1996 | Alter et al. |
| 5,569,192 A | 10/1996 | van der Wal |
| 5,591,138 A | 1/1997 | Vaillancourt |
| 5,599,309 A | 2/1997 | Marshall et al. |
| 5,616,128 A | 4/1997 | Meyer |
| 5,620,421 A | 4/1997 | Schmitz |
| 5,634,906 A | 6/1997 | Haber et al. |
| 5,637,094 A | 6/1997 | Stewart, Jr. et al. |
| 5,645,534 A | 7/1997 | Chanoch |
| 5,658,259 A | 8/1997 | Pearson et al. |
| 5,681,291 A | 10/1997 | Galli |
| 5,744,360 A | 4/1998 | Hu et al. |
| 5,779,677 A | 7/1998 | Frezza |
| 5,807,335 A | 9/1998 | Kriesel et al. |
| 5,807,346 A | 9/1998 | Frezza |

(56) References Cited

U.S. PATENT DOCUMENTS

| | | |
|---|---|---|
| 5,817,111 A | 10/1998 | Riza |
| 5,843,036 A | 12/1998 | Olive et al. |
| 5,885,250 A | 3/1999 | Kriesel et al. |
| 5,931,817 A | 8/1999 | Nguyen et al. |
| 5,957,886 A | 9/1999 | Weston |
| 5,957,897 A | 9/1999 | Jeffrey |
| 5,984,900 A | 11/1999 | Mikkelsen |
| 5,993,421 A | 11/1999 | Kriesel |
| 6,048,336 A | 4/2000 | Gabriel |
| 6,056,728 A | 5/2000 | von Schuckmann |
| 6,077,247 A | 6/2000 | Marshall et al. |
| 6,090,070 A | 7/2000 | Hager et al. |
| 6,090,080 A | 7/2000 | Jost et al. |
| 6,090,382 A | 7/2000 | Salfeld et al. |
| 6,099,503 A | 8/2000 | Stradella |
| 6,102,896 A | 8/2000 | Roser |
| 6,110,147 A | 8/2000 | Perouse |
| 6,149,626 A | 11/2000 | Bachynsky et al. |
| 6,159,181 A | 12/2000 | Crossman et al. |
| 6,171,285 B1 | 1/2001 | Johnson |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,221,044 B1 | 4/2001 | Greco |
| 6,241,709 B1 | 6/2001 | Bechtold et al. |
| 6,258,068 B1 | 7/2001 | Kirchhofer et al. |
| 6,258,562 B1 | 7/2001 | Salfeld et al. |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchhofer et al. |
| 6,312,412 B1 | 11/2001 | Saied et al. |
| 6,319,233 B1 | 11/2001 | Jansen et al. |
| 6,319,234 B1 | 11/2001 | Restelli et al. |
| 6,322,540 B1 | 11/2001 | Grabis et al. |
| 6,371,939 B2 | 4/2002 | Bergens et al. |
| 6,387,074 B1 | 5/2002 | Horppu et al. |
| 6,387,078 B1 | 5/2002 | Gillespie, III |
| 6,413,237 B1 | 7/2002 | Caizza et al. |
| 6,419,658 B1 | 7/2002 | Restelli et al. |
| D461,555 S | 8/2002 | Binet et al. |
| 6,475,194 B2 | 11/2002 | Domici, Jr. et al. |
| 6,509,015 B1 | 1/2003 | Salfeld et al. |
| 6,517,517 B1 | 2/2003 | Farrugia et al. |
| 6,537,252 B1 | 3/2003 | Hansen |
| 6,544,234 B1 | 4/2003 | Gabriel |
| 6,575,939 B1 | 6/2003 | Brunel |
| 6,589,210 B1 | 7/2003 | Rolfe |
| 6,656,163 B1 | 12/2003 | Marshall et al. |
| 6,656,164 B1 | 12/2003 | Smith |
| 6,673,035 B1 | 1/2004 | Rice et al. |
| 6,692,469 B1 | 2/2004 | Weekes et al. |
| 6,712,788 B2 | 3/2004 | Righi et al. |
| 6,743,203 B1 | 6/2004 | Pickhard |
| 6,752,798 B2 | 6/2004 | McWethy et al. |
| 6,767,336 B1 | 7/2004 | Kaplan |
| D494,270 S | 8/2004 | Reschke |
| 6,773,415 B2 * | 8/2004 | Heiniger ............... A61M 5/326 604/110 |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen et al. |
| 6,872,194 B2 | 3/2005 | Doyle et al. |
| 6,926,697 B2 | 8/2005 | Malenchek |
| 6,932,793 B1 | 8/2005 | Marshall et al. |
| 6,945,960 B2 | 9/2005 | Barker et al. |
| 6,976,976 B2 | 12/2005 | Doyle |
| 6,986,760 B2 | 1/2006 | Giambattista et al. |
| 7,001,364 B1 | 2/2006 | Farhi |
| 7,004,929 B2 | 2/2006 | McWethy et al. |
| D518,175 S | 3/2006 | Hardin, Jr. et al. |
| 7,056,306 B1 | 6/2006 | Halseth et al. |
| 7,223,394 B2 | 5/2007 | Salfeld et al. |
| 7,320,682 B2 | 1/2008 | Cocker et al. |
| 7,361,160 B2 | 4/2008 | Hommann et al. |
| 7,497,847 B2 | 3/2009 | Crawford et al. |
| 7,541,031 B2 | 6/2009 | Salfeld et al. |
| 7,588,761 B2 | 9/2009 | Salfeld et al. |
| 7,694,828 B2 | 4/2010 | Swift et al. |
| 7,736,333 B2 | 6/2010 | Gillespie, III |
| D622,374 S | 8/2010 | Julian et al. |
| 7,771,397 B1 * | 8/2010 | Olson ................. A61M 5/3202 604/192 |
| D629,509 S | 12/2010 | Julian et al. |
| 7,863,426 B2 | 1/2011 | Wan et al. |
| 7,919,264 B2 | 4/2011 | Maksymowych et al. |
| 7,938,802 B2 | 5/2011 | Bicknell et al. |
| 8,162,887 B2 | 4/2012 | Bicknell et al. |
| D677,380 S | 3/2013 | Julian et al. |
| 9,180,244 B2 | 11/2015 | Anderson et al. |
| 2001/0005781 A1 | 6/2001 | Bergens et al. |
| 2001/0053894 A1 | 12/2001 | Steenfeldt-Jensen et al. |
| 2002/0002344 A1 | 1/2002 | Douglas et al. |
| 2002/0016563 A1 | 2/2002 | Hill et al. |
| 2002/0042592 A1 | 4/2002 | Wilmot et al. |
| 2002/0095120 A1 | 7/2002 | Larsen et al. |
| 2002/0111587 A1 | 8/2002 | Hommann et al. |
| 2002/0161337 A1 | 10/2002 | Shaw |
| 2002/0169408 A1 | 11/2002 | Beretta et al. |
| 2002/0183690 A1 | 12/2002 | Arnisolle |
| 2003/0004466 A1 | 1/2003 | Bitdinger et al. |
| 2003/0004467 A1 | 1/2003 | Musick et al. |
| 2003/0023203 A1 | 1/2003 | Lavi et al. |
| 2003/0023205 A1 | 1/2003 | Botich et al. |
| 2003/0050606 A1 | 3/2003 | Brand et al. |
| 2003/0093036 A1 | 5/2003 | Crossman et al. |
| 2003/0105430 A1 | 6/2003 | Lavi et al. |
| 2003/0161744 A1 | 8/2003 | Vilks et al. |
| 2003/0187401 A1 | 10/2003 | Doyle |
| 2003/0212362 A1 | 11/2003 | Roser |
| 2003/0229308 A1 | 12/2003 | Tsals et al. |
| 2003/0236502 A1 | 12/2003 | De La Serna et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0054327 A1 | 3/2004 | Gillespie |
| 2004/0147875 A1 | 7/2004 | Wallace et al. |
| 2004/0199117 A1 | 10/2004 | Giambattista et al. |
| 2004/0215151 A1 | 10/2004 | Marshall et al. |
| 2004/0225262 A1 | 11/2004 | Fathallah et al. |
| 2005/0020979 A1 | 1/2005 | Westbye et al. |
| 2005/0020984 A1 | 1/2005 | Lesch |
| 2005/0027255 A1 | 2/2005 | Lavi et al. |
| 2005/0049550 A1 | 3/2005 | Kirchhofer et al. |
| 2005/0049561 A1 | 3/2005 | Hommann et al. |
| 2005/0085776 A1 | 4/2005 | Hommann et al. |
| 2005/0096597 A1 | 5/2005 | Crawford et al. |
| 2005/0101919 A1 | 5/2005 | Brunnberg |
| 2005/0124940 A1 | 6/2005 | Martin et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0209569 A1 | 9/2005 | Ishikawa et al. |
| 2005/0222539 A1 | 10/2005 | Gonzales et al. |
| 2005/0222540 A1 | 10/2005 | Kirchhofer et al. |
| 2005/0261634 A1 | 11/2005 | Karlsson |
| 2005/0273054 A1 | 12/2005 | Asch |
| 2005/0273055 A1 | 12/2005 | Harrison et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0030819 A1 | 2/2006 | Young et al. |
| 2006/0036216 A1 | 2/2006 | Rimlinger et al. |

(56) References Cited

U.S. PATENT DOCUMENTS

| | | |
|---|---|---|
| 2006/0047250 A1 | 3/2006 | Hickingbotham et al. |
| 2006/0069350 A1 | 3/2006 | Buenger et al. |
| 2006/0069354 A1 | 3/2006 | Buenger et al. |
| 2006/0100588 A1 | 5/2006 | Brunnberg et al. |
| 2006/0111666 A1 | 5/2006 | Hommann et al. |
| 2006/0111674 A1 | 5/2006 | Vedrine |
| 2006/0129122 A1 | 6/2006 | Wyrick |
| 2006/0167413 A1 | 7/2006 | Marshall et al. |
| 2006/0189933 A1 | 8/2006 | Alheidt et al. |
| 2006/0253083 A1 | 11/2006 | Liu |
| 2007/0049865 A1 | 3/2007 | Radmer et al. |
| 2007/0129674 A1 | 6/2007 | Liversidge |
| 2007/0142776 A9 | 6/2007 | Kovelman et al. |
| 2007/0161960 A1 | 7/2007 | Chen et al. |
| 2007/0173772 A1 | 7/2007 | Liversidge |
| 2007/0239117 A1 | 10/2007 | Chelak et al. |
| 2008/0097337 A1 | 4/2008 | Judd et al. |
| 2008/0103453 A1* | 5/2008 | Liversidge ............ A61M 5/326 604/187 |
| 2008/0208125 A1 | 8/2008 | Bicknell et al. |
| 2008/0208140 A1 | 8/2008 | Barrelle |
| 2008/0269692 A1 | 10/2008 | James et al. |
| 2008/0300549 A1 | 12/2008 | Verespej et al. |
| 2009/0024076 A1 | 1/2009 | Babaev |
| 2009/0024093 A1 | 1/2009 | Carrel et al. |
| 2009/0036870 A1 | 2/2009 | Mounce et al. |
| 2009/0157012 A1 | 6/2009 | Magne |
| 2009/0182284 A1 | 7/2009 | Morgan |
| 2009/0240210 A1 | 9/2009 | Walton et al. |
| 2009/0299328 A1 | 12/2009 | Mudd et al. |
| 2010/0160869 A1 | 6/2010 | Liversidge |
| 2010/0160894 A1 | 6/2010 | Julian et al. |
| 2011/0054414 A1 | 3/2011 | Shang et al. |
| 2011/0178500 A1 | 7/2011 | Shang et al. |
| 2011/0218502 A1 | 9/2011 | Iio et al. |
| 2012/0107783 A1 | 5/2012 | Julian et al. |
| 2012/0191047 A1* | 7/2012 | Raday ................. A61M 5/2033 604/198 |
| 2012/0197209 A1 | 8/2012 | Bicknell et al. |
| 2012/0233834 A1 | 9/2012 | Szechinski et al. |
| 2012/0289905 A1 | 11/2012 | Julian et al. |

FOREIGN PATENT DOCUMENTS

| | | |
|---|---|---|
| DE | 60207576 T2 | 6/2006 |
| EP | 0068864 A2 | 1/1983 |
| EP | 0260610 A2 | 3/1988 |
| EP | 1334740 A1 | 8/2003 |
| EP | 1364667 A2 | 11/2003 |
| EP | 1523360 A1 | 4/2005 |
| EP | 2067496 A1 | 6/2009 |
| EP | 2085104 A1 | 8/2009 |
| EP | 2361648 A1 | 8/2011 |
| GB | 2239180 A | 6/1991 |
| GB | 2243552 A | 11/1991 |
| GB | 2388033 A | 11/2003 |
| GB | 2465389 A | 5/2010 |
| JP | 5014835 B2 | 5/1975 |
| JP | 5161712 B2 | 6/1993 |
| JP | 2001-512038 A | 8/2001 |
| JP | 2003-511105 A | 3/2003 |
| JP | 2003-225308 A | 8/2003 |
| JP | 2006-507060 A | 3/2006 |
| JP | 2009-511177 A | 3/2009 |
| JP | 2010-540055 A | 12/2010 |
| KR | 20070050410 A | 5/2007 |
| RU | 2004256 C1 | 12/1993 |
| RU | 2108116 C1 | 4/1998 |
| RU | 2131748 C1 | 6/1999 |
| RU | 2169584 C1 | 6/2001 |
| WO | 1993/013819 A1 | 7/1993 |
| WO | 1994009839 A1 | 5/1994 |
| WO | 1994013342 A1 | 6/1994 |
| WO | 1994026333 A1 | 11/1994 |
| WO | 1999022789 A1 | 5/1999 |
| WO | 1999022792 A1 | 5/1999 |
| WO | 0137908 A1 | 5/2001 |
| WO | 2001062319 A2 | 8/2001 |
| WO | 2003039633 A2 | 5/2003 |
| WO | 2003077968 A2 | 9/2003 |
| WO | 2003097133 A1 | 11/2003 |
| WO | 2003099358 A2 | 12/2003 |
| WO | 2004000397 A1 | 12/2003 |
| WO | 2004047892 A1 | 6/2004 |
| WO | 2004060451 A1 | 7/2004 |
| WO | 2004067068 A1 | 8/2004 |
| WO | 2005002653 A1 | 1/2005 |
| WO | 2005046765 A2 | 5/2005 |
| WO | 2005079889 A1 | 9/2005 |
| WO | 2005090836 A1 | 9/2005 |
| WO | 2005113039 A1 | 12/2005 |
| WO | 2005115508 A1 | 12/2005 |
| WO | 2005115509 A1 | 12/2005 |
| WO | 2005115510 A1 | 12/2005 |
| WO | 2005115511 A1 | 12/2005 |
| WO | 2005115512 A1 | 12/2005 |
| WO | 2005115513 A1 | 12/2005 |
| WO | 2005115516 A1 | 12/2005 |
| WO | 2006000785 A1 | 1/2006 |
| WO | 2006058061 A1 | 6/2006 |
| WO | 2006063015 A2 | 6/2006 |
| WO | 2007/138299 A1 | 12/2007 |
| WO | 2008/005315 A2 | 1/2008 |
| WO | 2009/019439 A1 | 2/2009 |
| WO | 2009/040603 A1 | 4/2009 |
| WO | 2009/155277 A1 | 12/2009 |
| WO | 2012/101629 A1 | 8/2012 |

OTHER PUBLICATIONS

Owen Mumford drawing/schematic of the Abbott-Plunger AUTOject Mini, dated Mar. 25, 2002, Drawing No. P02 207.
Owen Mumford drawing/schematic of the Plunger-Miniject dated Mar. 30, 1993, Drawing No. AJ 358.
Owen Mumford drawing/schematic of the Plunger-Miniject dated Mar. 30, 1993, Drawing No. P93.022.
Patent Examination Report No. 1 issued in Australian Application No. 2012209222, dated May 26, 2014.
Reexamination Decision issued in Chinese Application No. 200580020958.6, dated Jun. 13, 2011.
Rejection Decision issued in Chinese Application No. 200580020958.6, dated Jun. 5, 2009.
Summons to Attend Oral Proceedings pursuant to Rule 115(1) EPC, dated Apr. 20, 2012.
Written Opinion issued in International Application No. PCT/GB2005/002487, dated Dec. 23, 2006.
Written Opinion issued in International Application No. PCT/US2004/013278, dated Oct. 29, 2006.
Written Opinion issued in International Application No. PCT/US2007/015095, dated Sep. 11, 2008.
Written Opinion issued in International Application No. PCT/US2010/033012, dated Jul. 2, 2010.
Written Opinion issued in International Application No. PCT/2010/060496, dated Feb. 16, 2011.
Written Opinion issued in International Application No. PCT/US2011/033504, dated Jul. 8, 2011.
Written Opinion issued in International Application No. PCT/US2012/022433, dated Jul. 5, 2012.
Written Opinion of International Search Authority for International Application No. PCT/IL2012/000037; dated May 15, 2012 (5 pages).
Preliminary Rejection in Korean Patent Application No. 10-2013-7022181 dated Mar. 22, 2016.
Decision to Grant in Ukraine Patent Application No. 201310406 dated Apr. 26, 2016.
Office Action issued in Israel patent applicaiton No. 227238 dated Jul. 26, 2016.
"Abbott Receives FDA Approval for New Humira Delivery Device," Press Release, dated Jun. 26, 2006 (color).

(56) References Cited

OTHER PUBLICATIONS

BD Preventis, Shielding System for Prefilled Syringes, http://www.bd.com/pharmaceuticals/products/safety-engineered.asp, last accessed Aug. 26, 2010.
Communication of a Notice of Opposition issued in European Application No. 04822031.3-1526, dated Jan. 6, 2010.
Communication pursuant to Article 94(3) EPC issued by the European Patent Office in European Application No. 05758156.3-2320, dated Jan. 18, 2011.
Communication pursuant to Article 96(2) EPC issued in European Application No. 04822031.3-1526, dated May 31, 2007.
Communication under Rule 112 EPC issued in European Application No. 04822031.3, dated Mar. 13, 2007.
Correspondence from Dept. of Health & Human Services, Food and Drug Administration, to Robert Shaw/Owen Mumford, Inc. regarding Section 501(k) notification to market device, dated Mar. 6, 2000.
Decision of Final Rejection issued in Japanese Application No. 2007-517459, dated Jan. 10, 2012.
Decision on Grant issued in Russian Application No. 2006145501/14(049694), dated Nov. 2, 2009.
Decision on Grant issued in Russian Application No. 2009102986/14(003862), dated Jun. 30, 2011.
Examination Report issued in New Zealand Application No. 552340, dated Apr. 27, 2009.
Examination Report issued in New Zealand Application No. 552340, dated Aug. 12, 2010.
First Examination Report issued in New Zealand Application No. 612784, issued May 26, 2014.
First Examination Report issued in New Zealand Patent Application No. 711448, dated Sep. 16, 2015.
International Preliminary Report on Patentability issued for International Application No. PCT/IL2012/000037; dated Jul. 30, 2013 (6 pages).
International Preliminary Report on Patentability issued in International Application No. PCT/GB2005/002487, dated Sep. 7, 2006.
International Preliminary Report on Patentability issued in International Application No. PCT/US2004/013278, dated Nov. 1, 2006.
International Preliminary Report on Patentability issued in International Application No. PCT/US2007/015095, dated Jun. 19, 2009.
International Preliminary Report on Patentability issued in International Application No. PCT/US2010/033012, dated Nov. 1, 2011.
International Search Report and Written Opinion issued in International Application No. PCT/US2012/022432, dated Apr. 18, 2012.
International Search Report for International Application No. PCT/IL2012/000037; dated May 15, 2012 (2 pages).
International Search Report issued in International Application No. PCT/GB2005/002487, dated Aug. 19, 2005.
International Search Report issued in International Application No. PCT/US2004/013278, dated May 30, 2005.
International Search Report issued in International Application No. PCT/US2007/015095, dated Sep. 11, 2008.
International Search Report issued in International Application No. PCT/US2010/033012, dated Jul. 2, 2010.
International Search Report issued in International Application No. PCT/US2010/060496, dated Feb. 16, 2011.
International Search Report issued in International Application No. PCT/US2011/033504, dated Jul. 8, 2011.
International Search Report issued in International Application No. PCT/US2012/022433, dated Jul. 5, 2012.
Notice of Acceptance issued for Australian Application No. 2012209222, dated Jun. 26, 2015.
Notice of Reasons for Rejection issued in Japanese Application No. 2007-517459, dated Aug. 24, 2010.
Notice of Reasons for Rejection issued in Japanese Application No. 2007-517459, dated Mar. 8, 2011.
Notice of Rejection issued in Japanese Application No. 2009-518284, dated May 29, 2012.
Notification of Provisional Rejection issued in Korean Application No. 10-2006-7026814, dated Jul. 19, 2011.
Notification of Reexamination issued in Chinese Application No. 200580020958.6, dated Aug. 17, 2010.
Nov. 10, 1999 correspondence from Dept. of Health & Human Services, Food and Drug Administration to Robert Shaw/Owen Mumford regarding Section 501 (k) notification intent to market device.
Office Action issued in Australian Application No. 2005256832, dated Apr. 18, 2011.
Office Action issued in Australian Application No. 2005256832, dated Feb. 22, 2010.
Office Action issued in Canadian Application No. 2,571,571, dated Oct. 24, 2011.
Office Action issued in Canadian Patent Application No. 2,824,454, dated Oct. 26, 2015.
Office Action issued in Chinese Application No. 200580020958.6, dated Sep. 5, 2008.
Office Action issued in Chinese Application No. 201010576413.6, dated Nov. 2, 2011.
Office Action issued in Chinese Application No. 201280006285.9, dated Dec. 22, 2014.
Office Action issued in Colombian Application No. 13198327, dated Jul. 25, 2014.
Office Action issued in Japanese Patent Application No. 2013-550667, dated Aug. 25, 2015.
Office Action issued in Mexican Application No. PA/a/2006/015056, dated Apr. 1, 2011.
Office Action issued in Mexican Application No. PA/a/2006/015056, dated Jul. 28, 2010.
Office Action issued in Philippines Application No. 1-2013-501516, dated Nov. 6, 2014.
Office Action issued in Russian Application No. 2006145501/14(049694), dated May 21, 2009.
Office Action issued in Russian Application No. 2013139355, dated Dec. 4, 2014.
Owen Mumford drawing/schematic A of the Plunger-Miniject dated Sep. 5, 1997, Drawing No. AJ 654.

* cited by examiner

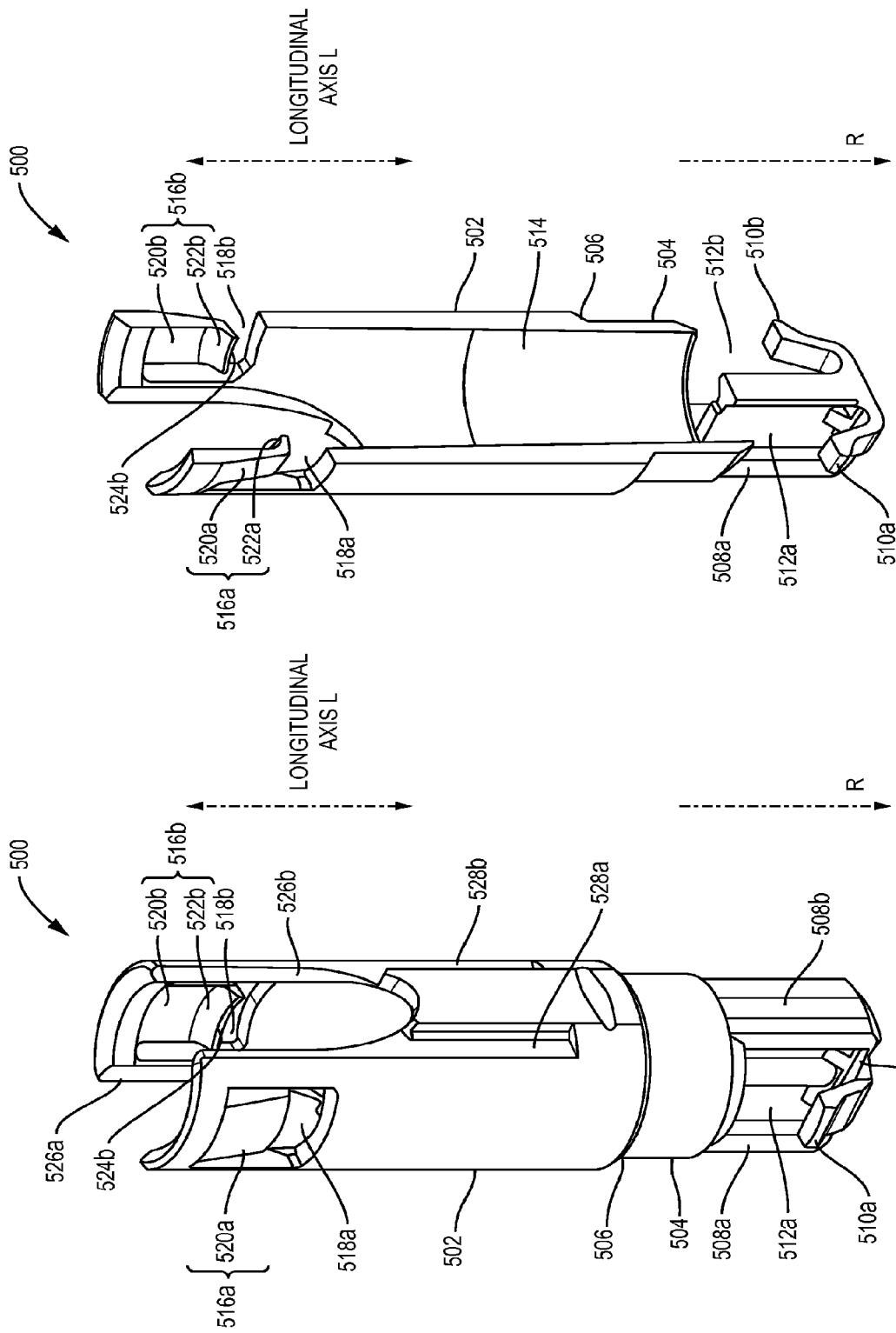

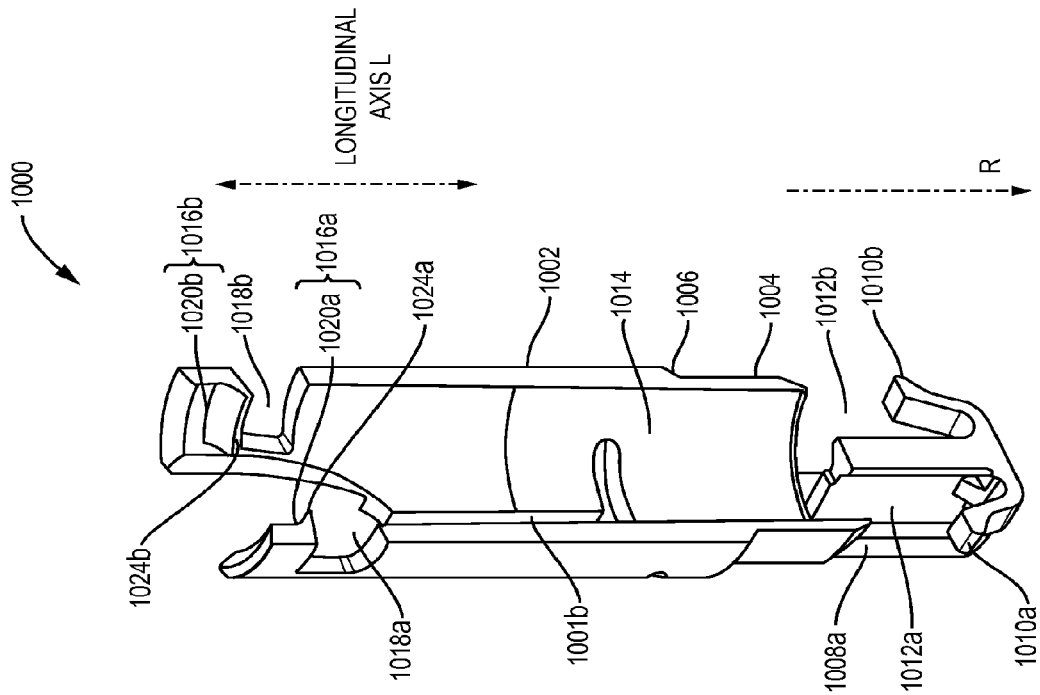
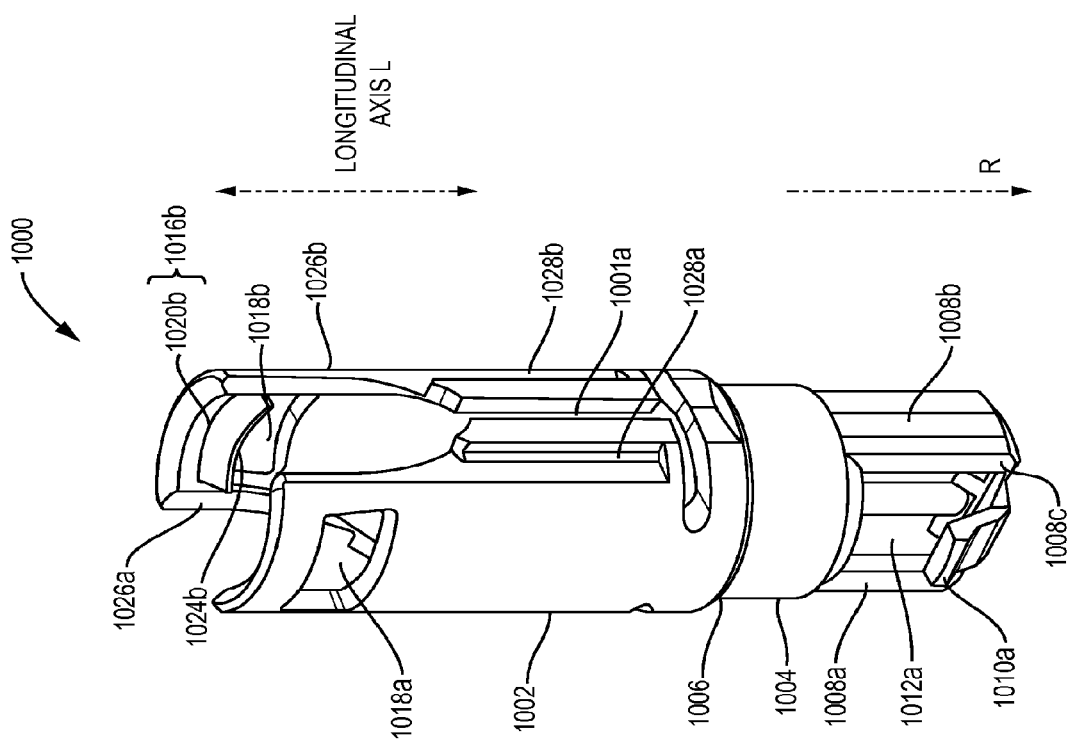

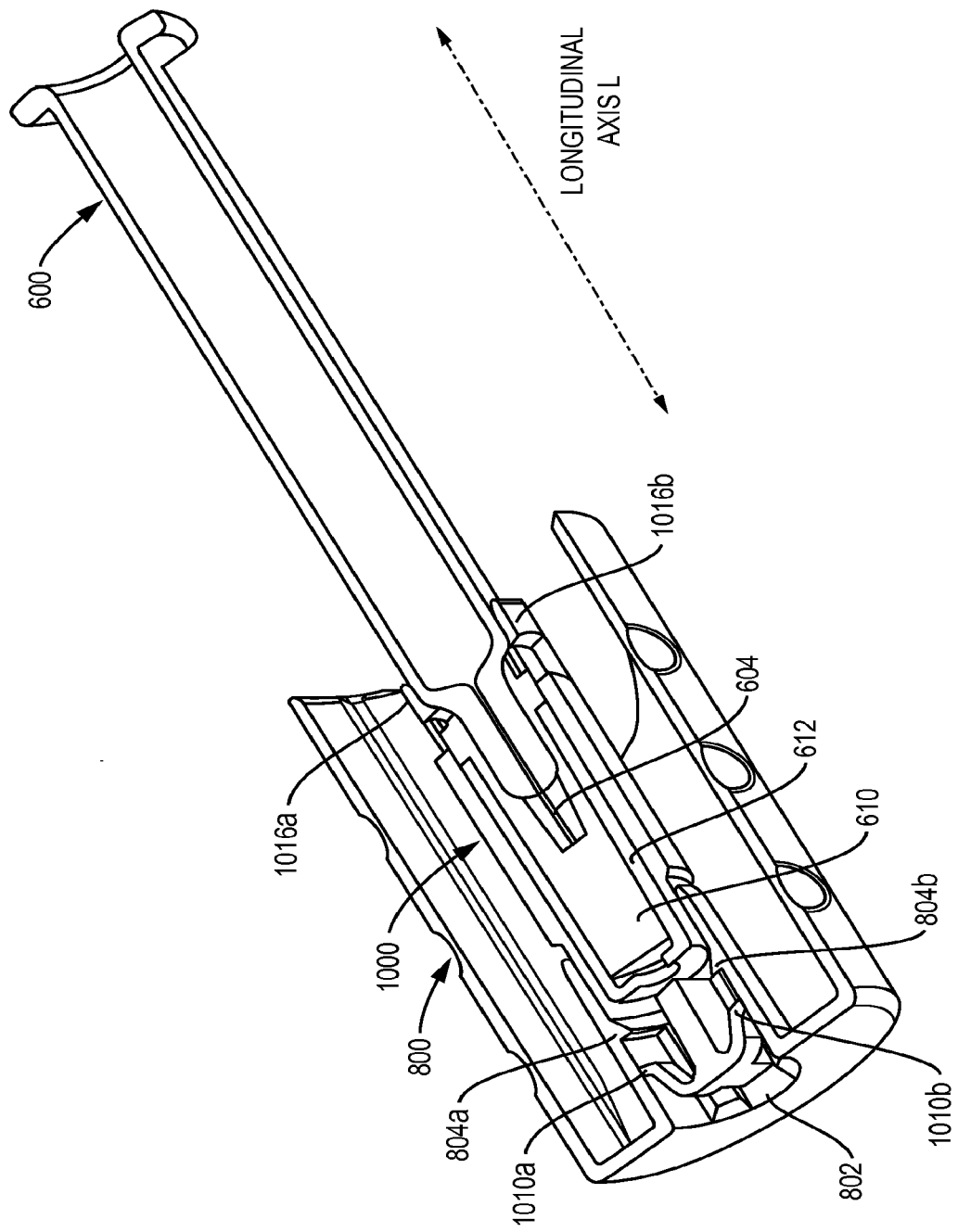

REMOVAL OF NEEDLE SHIELD FROM SYRINGES AND AUTOMATIC INJECTION DEVICES

RELATED APPLICATIONS

This application is a continuation of and claims the benefit of priority to U.S. Ser. No. 14/253,348, filed on Apr. 15, 2014, which is a continuation of and claims benefit of priority to U.S. Ser. No. 13/357,508, filed on Jan. 24, 2012, which claims the benefit of priority to U.S. Provisional Patent Application No. 61/435,467, filed Jan. 24, 2011, the entire contents of each application are incorporated herein by reference.

BACKGROUND

Automatic injection devices offer an alternative to manually-operated syringes for administering therapeutic agents into patients' bodies and allowing patients to self-administer therapeutic agents. Automatic injection devices may be used to administer medications under emergency conditions, for example, to administer epinephrine to counteract the effects of a severe allergic reaction. Automatic injection devices have also been described for use in administering anti-arrhythmic medications and selective thrombolytic agents during a heart attack. See, for example, U.S. Pat. Nos. 3,910,260; 4,004,577; 4,689,042; 4,755,169; and 4,795,433, the entire contents of which are incorporated herein in their entirety by reference. Various types of automatic injection devices are also described in, for example, U.S. Pat. Nos. 3,941,130; 4,261,358; 5,085,642; 5,092,843; 5,102,393; 5,267,963; 6,149,626; 6,270,479; and 6,371,939; and International Patent Publication No. WO/2008/005315, the entire contents of which are incorporated herein in their entirety by reference.

Conventionally, an automatic injection device houses a syringe and, when operated, causes the syringe to move forwardly and a needle to project from the housing so that a therapeutic agent contained in the syringe is injected into a patient's body.

A conventional automatic injection may include one or more needle shields to protect the syringe needle from damage and accidental contact and to maintain sterility of the injection needle. Needle shields include a soft needle shield that is formed of a flexible material, and a rigid needle shield that is formed of a rigid, inflexible material and that provide greater mechanical protection to the injection needle. Conventional automatic injection devices may also include a removable cap covering the needle shields to provide mechanical protection for the needle shields and to facilitate removal of the needle shields before an injection may be performed.

FIGS. 1A and 1B illustrate an exemplary syringe 100 including a substantially tubular syringe body 102 for holding a therapeutic agent. FIG. 1A illustrates a side view of the exemplary syringe 100. FIG. 1B illustrates a cross-sectional view of the exemplary syringe 100 bisected along the longitudinal axis L. An injection needle may be coupled at a distal end of the syringe body 102. The injection needle may be covered and protected by a soft needle shield 104 and a rigid needle shield 106 that surrounds the soft needle shield 104. One or more apertures 108 may be provided in a side wall of the rigid needle shield 106 to allow a portion of the soft needle shield 104 to extend through the apertures 108. This permits the soft needle shield 104 and the rigid needle shield 106 to latch together which, in turn, permits removal of both the soft needle shield 104 and the rigid needle shield 106 when the rigid needle shield 106 is pulled away from the syringe body 102 in the distal direction (represented by arrow R), thereby exposing the injection needle for use in performing an injection. In an exemplary embodiment, a ridged portion 110 may be provided in the exterior surface of the rigid needle shield 106. The ridged portion 110 may include one or more alternating outwardly-projecting ridges interspaced with grooves, and may thereby provide a region of higher friction contact for removal of the rigid needle shield 106 from the syringe.

SUMMARY

Exemplary embodiments provide a needle shield remover that reliably engages with a distal cap of an automatic injection device and with one or more needle shields coupled to a syringe of the device. An exemplary needle shield remover includes one or more inwardly-projecting shield engagement mechanisms that reliably engage with the needle shields, and one or more cap engagement mechanisms that reliably engage with the distal cap. When a user removes the distal cap, the needle shield remover reliably removes the needle shields (e.g., a soft needle shield and a rigid needle shield) from the syringe, thereby exposing the injection needle for performing an injection. In an exemplary assembly method, an exemplary needle shield remover is engaged to a needle shield coupled to a syringe, prior to insertion of the syringe and needle shield remover assembly into a housing of the automatic injection device. This exemplary assembly method allows visual inspection, outside the housing of the device, to ensure that the needle shield remover is correctly and reliably engaged to the needle shield before the syringe and needle shield remover assembly is inserted into the housing.

In accordance with one exemplary embodiment, an apparatus is provided for removing a needle shield from a syringe. The apparatus includes a tubular member for enclosing the needle shield coupled to the syringe. The apparatus also includes one or more cap engagement mechanisms provided at a distal end of the tubular member and configured for engagement with a distal cap provided for covering a distal end of the syringe. The apparatus also includes one or more shield engagement mechanisms provided at a proximal end of the tubular member and configured for engagement with the needle shield. When the apparatus is pulled away from the syringe, the one or more shield engagement mechanisms exert force against the needle shield to remove the needle shield from the syringe.

In accordance with another exemplary embodiment, an automatic injection device is provided. The automatic injection device includes a syringe, a needle shield coupled to a distal end of the syringe, and a distal cap for covering the needle shield. The automatic injection device also includes a needle shield remover disposed between the needle shield and the distal cap. The needle shield includes a tubular member for enclosing the needle shield coupled to the syringe, one or more cap engagement mechanisms provided at a distal end of the tubular member and engaged with the distal cap, and one or more shield engagement mechanisms provided at a proximal end of the tubular member and engaged with the needle shield. When the needle shield remover is pulled away from the syringe, the one or more shield engagement mechanisms exert force against the needle shield to remove the needle shield from the syringe.

In accordance with another exemplary embodiment, a method is provided for assembling an automatic injection device. The method includes coupling a needle shield to a distal end of a syringe. The method also includes engaging one or more shield engagement mechanisms of a needle shield remover to the needle shield. The method further includes inserting an assembly comprising the syringe, the needle shield and the needle shield remover into a housing of the automatic injection device.

BRIEF DESCRIPTION TO THE DRAWINGS

The foregoing and other objects, aspects, features, and advantages of exemplary embodiments will become more apparent and may be better understood by referring to the following description taken in conjunction with the accompanying drawings, in which:

FIG. 5A illustrates a perspective view of an exemplary needle shield remover.

FIG. 5B illustrates a cross-sectional perspective view of the exemplary needle shield remover of FIG. 5A bisected along a longitudinal axis L.

FIG. 10A illustrates a perspective view of an exemplary needle shield remover.

FIG. 10B illustrates a cross-sectional perspective view of the exemplary needle shield remover of FIG. 10A bisected along a longitudinal axis L.

FIG. 11 illustrates a cross-sectional perspective view of the exemplary needle shield remover of FIGS. 10A and 10B assembled with a syringe and a distal cap.

DETAILED DESCRIPTION

Figure 1A:
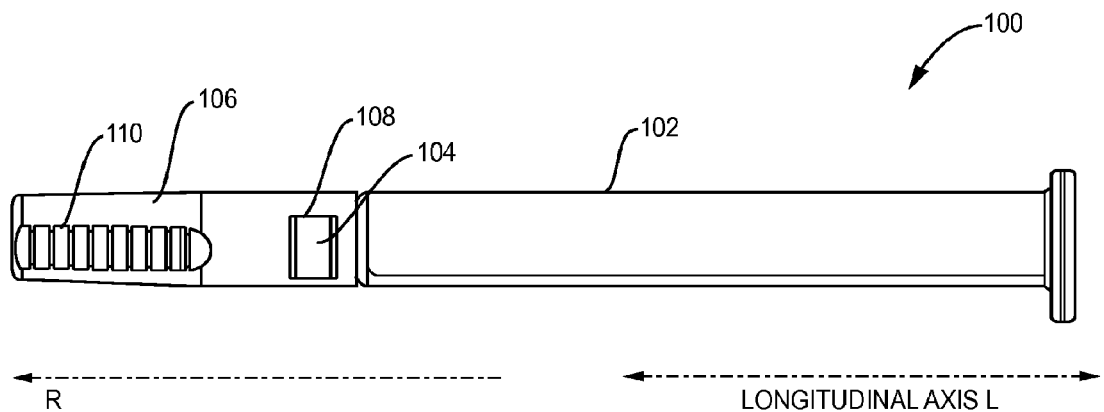
FIG. 1A illustrates a side view of an exemplary syringe.
Figure 1B:
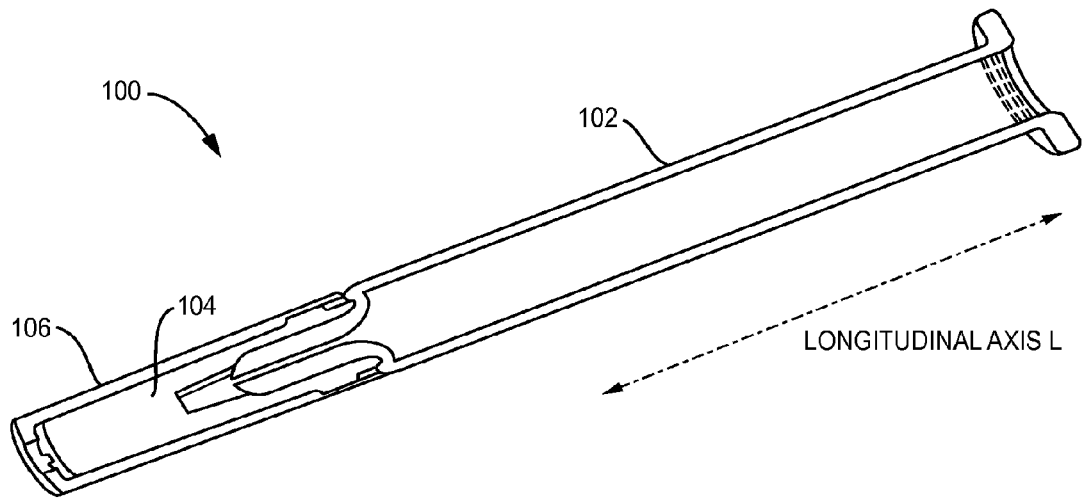
FIG. 1B illustrates a cross-sectional view of the exemplary syringe of FIG. 1A bisected along the longitudinal axis L.

One difficulty in the design of conventional automatic injection devices lies in providing a mechanism that reliably engages a soft needle shield and/or a rigid needle shield to remove it from the syringe. For example, in certain conventional automatic injection devices, a removable distal cap includes a mechanism that snaps into position in a gap formed between the syringe body and the needle shield. When the removable distal cap is removed, the mechanism in the cap allows the needle shield to be removed as well because of its engagement with the cap. However, due to component tolerances and other component variations that arise during the manufacturing process, it is difficult to achieve, in a conventional automatic injection device, a needle shield removal mechanism that consistently fits within the gap formed between the syringe body and the needle shield. For the same reasons, it is difficult to ensure, in a conventional automatic injection device, that the needle shield removal mechanism is maintained in engagement with the needle shield, and that the needle shield removal mechanism applies an appropriate level of force to the needle shield when the user removes the cap in order to remove the needle shield.

Exemplary embodiments address the deficiencies in conventional automatic injection devices by providing a needle shield remover that reliably engages and removes one or more needle shields when a removable distal cap is removed from a distal end of the device. An exemplary needle shield remover may be provided separately from one or more needle shields and from a removable distal cap covering the distal end of the device. The needle shield remover may include one or more inwardly-projecting shield engagement mechanisms that reliably engage with one or more needle shields, and one or more cap engagement mechanisms that reliably engage with the removable distal cap. When a user removes the removable distal cap covering the distal end of the device, the exemplary needle shield remover reliably removes the needle shields from the syringe, thereby exposing the injection needle for performing an injection.

U.S. Provisional Patent Application No. 61/435,467, filed Jan. 24, 2011, to which the present application claims priority, teaches some exemplary needle shield removers that employ the concept of "float" relative to a removable distal cap and a needle shield remover attached thereto prior to placement of the removable distal cap onto an automatic injection device. U.S. Provisional Patent Application No. 61/435,467, filed Jan. 24, 2011, also teaches some exemplary needle shield removers that are "floatless" and do not employ the concept of "float" relative to a removable distal cap and a needle shield remover attached to an automatic injection device.

The concept of "float" refers to the structure, function and operation of a needle shield remover and a removable distal cap that form a single assembly and, as part of the assembly, slide relative to each other along a longitudinal axis during attachment to an automatic injection device, where the relative movement exceeds acceptable tolerances that account for manufacturing variations in the assembled components. The employment of "float" refers to a single assembly formed of a needle shield remover and a removable distal cap that are pre-assembled before the needle shield remover is engaged to a needle shield. That is, in an automatic injection device that employs "float," the pre-assembled removable distal cap and needle shield remover form a one-piece assembly that is engaged to the needle shield and the automatic injection device after the syringe is loaded into the automatic injection device. The pre-assembled removable distal cap and needle shield remover are engaged to the automatic injection device in at least two steps in which the distal cap is first engaged to the automatic injection device, and subsequently the needle shield remover is engaged to the needle shield by sliding along a longitudinal axis from a first position to an second engaged position while the distal cap remains engaged to the automatic injection device.

Other exemplary needle shield removers and distal caps taught in the present application are "floatless" and do not rely on the concept of "float" for correctly and reliably assembling a needle shield remover and a removable distal cap in an automatic injection device. The concept of "floatless" or "floatlessness" refers to the structure, function and operation of an exemplary needle shield remover and a removable distal cap that are not pre-assembled as a single assembly and that are not configured to slide relative to each other along a longitudinal axis during attachment to an automatic injection device in order to engage the needle shield remover to the needle shield, where the relative movement exceeds acceptable tolerances that account for manufacturing variations in the assembled components. That is, in an automatic injection device that does not employ "float" (i.e., "floatless") the removable distal cap and the exemplary needle shield remover are not pre-assembled and do not form a one-piece assembly. That is, in exemplary "floatless" embodiments an exemplary needle shield remover is an assembly engaged to a needle shield attached to a syringe prior to insertion of the syringe and needle shield remover assembly into a housing of the automatic injection device. In turn, the removable distal cap is then engaged to the device in a one-step process in which coupling the distal cap to the distal end of the device housing also engages the distal cap with the needle shield remover. The structure, function and operation of the removable distal cap and the needle shield remover in "floatless" embodiments do not accommodate pre-assembly as a one piece assembly and do not accommodate movement of the needle shield remover attached to the removable distal cap from a first position to an engaged position along a longitudinal axis.

Automatic injection devices that do not rely on the concept of "float" to assemble an exemplary needle shield remover and a distal cap are advantageous over automatic injection devices that rely on the "float" concept. This is because reliance on the relative movement between the needle shield remover and the distal cap in automatic injection devices that use "float" increases the risk of unreliable and incorrect engagement of the needle shield remover with the needle shield, and thereby reduces robustness of the assembly.

Furthermore, the ability, in exemplary embodiments, to assemble the exemplary needle shield remover with the needle shield outside the device housing and outside the distal cap allows visual inspection of the assembly process to ensure that the needle shield remover is correctly and reliably engaged with a gap between the syringe body and the needle shield.

I. Definitions

Certain terms are defined in this section to facilitate understanding of exemplary embodiments.

The terms "automatic injection device" and "autoinjector," as used herein, refer to a device that enables a patient to self-administer a therapeutically effective dose of a therapeutic agent, wherein the device differs from a conventional syringe by the inclusion of a mechanism for automatically delivering the therapeutic agent to the patient by injection when the mechanism is engaged.

The terms "vessel" and "container," as used herein, refer to a syringe or cartridge that may be used in an exemplary automatic injection device for holding a dose of a therapeutic agent.

The terms "syringe" and "cartridge," as used herein, refer to a sterile barrel portion of an automatic injection device that is filled with a dose of a therapeutic agent prior to distribution or sale of the device to a patient or other non-medical professional for administration of the therapeutic agent to a patient. In an exemplary embodiment, a distal end of the barrel portion of a syringe may be coupled to a sterile hypodermic injection needle. In an exemplary embodiment, a distal end of the barrel portion of a cartridge may not be coupled to an injection needle. That is, in exemplary embodiments, a syringe may be a cartridge with a pre-attached injection needle coupled to its barrel portion.

Exemplary embodiments described herein with reference to a syringe assembly may also be implemented using a cartridge assembly. Similarly, exemplary embodiments described herein with reference to a cartridge assembly may also be implemented using a syringe assembly.

The term "pre-filled syringe," as used herein, refers to a syringe that is filled with a therapeutic agent immediately prior to administration of the therapeutic agent to a patient, and a syringe that is filled with a therapeutic agent and stored in this pre-filled form for a period of time before administration of the therapeutic agent to a patient.

The terms "injection needle" and "needle," as used herein, refer to a needle in an automatic injection device that is inserted into a patient's body to deliver a dose of a therapeutic agent into the patient's body. In an exemplary embodiment, the injection needle may be directly coupled to or may otherwise be in contact with a syringe assembly or a cartridge assembly that holds a dose of the therapeutic agent. In another exemplary embodiment, the injection needle may be indirectly coupled to the syringe or cartridge assembly, for example, via a syringe needle and/or a transfer mechanism that provides fluid communication between the syringe or cartridge assembly and the injection needle.

The term "thermoplastic material," as used herein, refers to a material that has the property of softening or fusing when heated and of hardening and becoming rigid again when cooled. Thermoplastic materials can be re-melted and cooled repeatedly without undergoing any appreciable chemical change. A thermoplastic is a polymer that turns to a liquid when heated and freezes to a very glassy state when cooled sufficiently. Most thermoplastics are high-molecular-weight polymers whose chains associate through weak Van der Waals forces (polyethylene); stronger dipole-dipole interactions and hydrogen bonding (nylon); or even stacking of aromatic rings (polystyrene). Thermoplastic polymers differ from thermosetting polymers (vulcanized rubber) as they can, unlike thermosetting polymers, be re-melted and re-molded. Many thermoplastic materials are addition polymers; e.g., vinyl chain-growth polymers such as polyethylene and polypropylene.

The term "pre-injection state," as used herein, refers to a state of an automatic injection device prior to activation of the device, i.e., prior to the start of delivery of a therapeutic agent contained in the device.

The term "injection state," as used herein, refers to one or more states of an automatic injection device during the delivery of a therapeutic agent contained in the device.

The term "post-injection state," as used herein, refers to completion of delivery of a therapeutically effective dose of a therapeutic agent contained in the device, or removal of the device from the patient prior to completion of delivery of a therapeutically effective dose of the therapeutic agent.

The term "patient" or "user," as used herein, refers to any type of animal, human or non-human, that may be administered a substance using exemplary automatic injection devices.

The term "proximal," as used herein, refers to a portion, end or component of an exemplary automatic injection device that is farthest from an injection site on a patient's body when the device is held against the patient for an injection or for mimicking an injection.

The term "distal," as used herein, refers to a portion, end or component of an exemplary automatic injection device that is closest to an injection site on a patient's body when the device is held against the patient for an injection or for mimicking an injection.

The term "planar" is used herein, in a broad lay sense, to mean exactly planar or approximately planar within some tolerance from the exactly planar.

The term "concave" is used herein, in a broad lay sense, to mean exactly concave or approximately concave within some tolerance from the exactly concave.

The term "convex" is used herein, in a broad lay sense, to mean exactly convex or approximately convex within some tolerance from the exactly convex.

The term "elliptical" is used herein, in a broad lay sense, to mean exactly elliptical or approximately elliptical within some tolerance from the exactly elliptical.

The term "oval" is used herein, in a broad lay sense, to mean exactly oval or approximately oval within some tolerance from the exactly oval.

The term "rectangular" is used herein, in a broad lay sense, to mean exactly rectangular or approximately rectangular within some tolerance from the exactly rectangular.

The term "parallel" is used herein, in a broad lay sense, to mean exactly parallel or approximately parallel within some tolerance from the exactly parallel.

The term "straight" is used herein, in a broad lay sense, to mean exactly straight or approximately straight within some tolerance from the exactly straight.

The term "equal" is used herein, in a broad lay sense, to mean exactly equal or approximately equal within some tolerance.

The term "adjacent" is used herein, in a broad lay sense, to mean immediately adjacent or approximately adjacent within some tolerance.

The term "transverse axis" is used herein to refer to an axis substantially perpendicular to a longitudinal axis.

The term "inwardly-projecting" is used herein to refer to one or more tabs or teeth on a needle shield remover extending length wise along a longitudinal axis and having a proximal end attached to a tubular structure of the needle shield remover and a distal end detached from the tubular structure of the needle shield remover and projecting inwardly into an inner cavity of the tubular structure.

II. Exemplary Needle Shield Removers

In an exemplary embodiment, a needle shield remover may be provided as a separate component from a needle shield for covering an injection needle and from a removable distal cap for covering a distal end of an automatic injection device. The needle shield remover may include one or more cap engagement mechanisms configured for engagement with the removable distal cap so that removal of the distal cap from the device housing automatically removes the needle shield remover as well. The needle shield remover may include one or more inwardly-projecting shield engagement mechanisms configured for directly or indirect engagement with a rigid needle shield (in a device that includes a rigid needle shield) and/or a soft needle shield (in a device that includes a soft needle shield but lacks a rigid needle shield). Since the needle shield remover is engaged to the needle shield, when the needle shield remover is removed from the device housing (e.g., by removal of the distal cap engaged to the needle shield remover), this results in the removal of the needle shield engaged to the needle shield remover.

Exemplary needle shield removers are configured and designed for quick, easy and reliable engagement to both the distal cap and to a needle shield. One or more exemplary methods may be used to assemble an exemplary needle shield remover to a needle shield coupled to a syringe. In an exemplary method, an exemplary needle shield remover may be assembled with a needle shield coupled to a syringe after the syringe has been inserted into the housing of the device. In another exemplary method, an exemplary needle shield remover—that is provided as a separate component from a distal cap and a syringe—may be assembled with a needle shield coupled to a syringe prior to insertion of the syringe into the housing of the device. The ability to assemble the needle shield remover to the needle shield outside the device housing allows visual inspection of the assembly process to ensure that the needle shield remover reliably engages the needle shield on the syringe before the syringe assembly is inserted into the device housing. Thus, assembly of the exemplary needle shield remover in the automatic injection device allows one to be certain that, when the syringe assembly is inserted into the device housing, the needle shield remover is engaged reliably and correctly with the needle shield, thereby resolving the issue of unreliable positioning of needle shield removal mechanisms in conventional automatic injection devices.

Figure 2A:
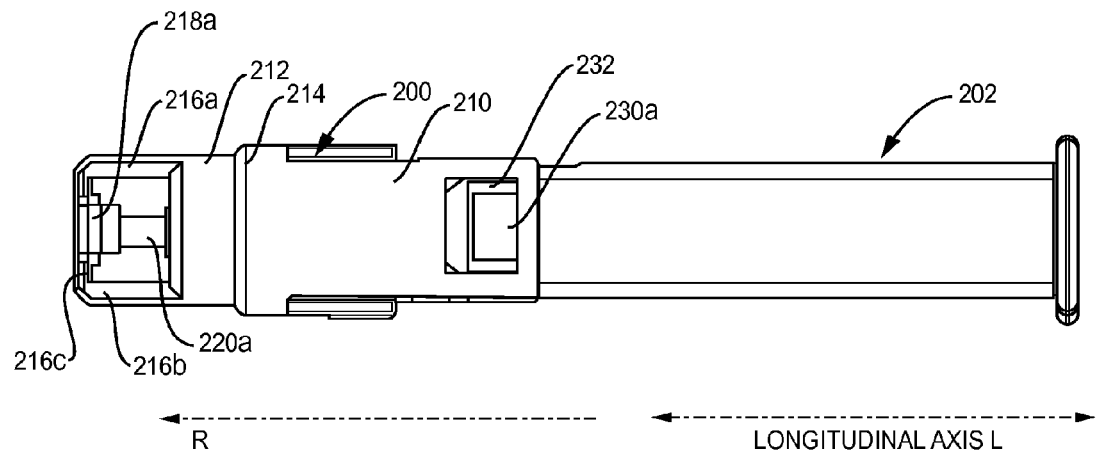
FIG. 2A illustrates a side view of an exemplary needle shield remover engaged to a syringe.
Figure 2B:
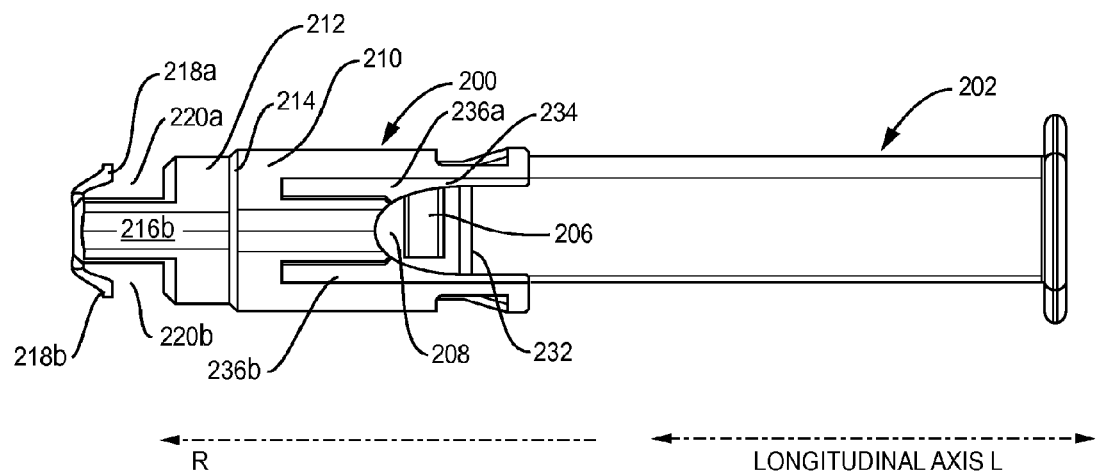
FIG. 2B illustrates another side view of the exemplary needle shield remover of FIG. 2A rotated by about 90 degrees.
Figure 2C:
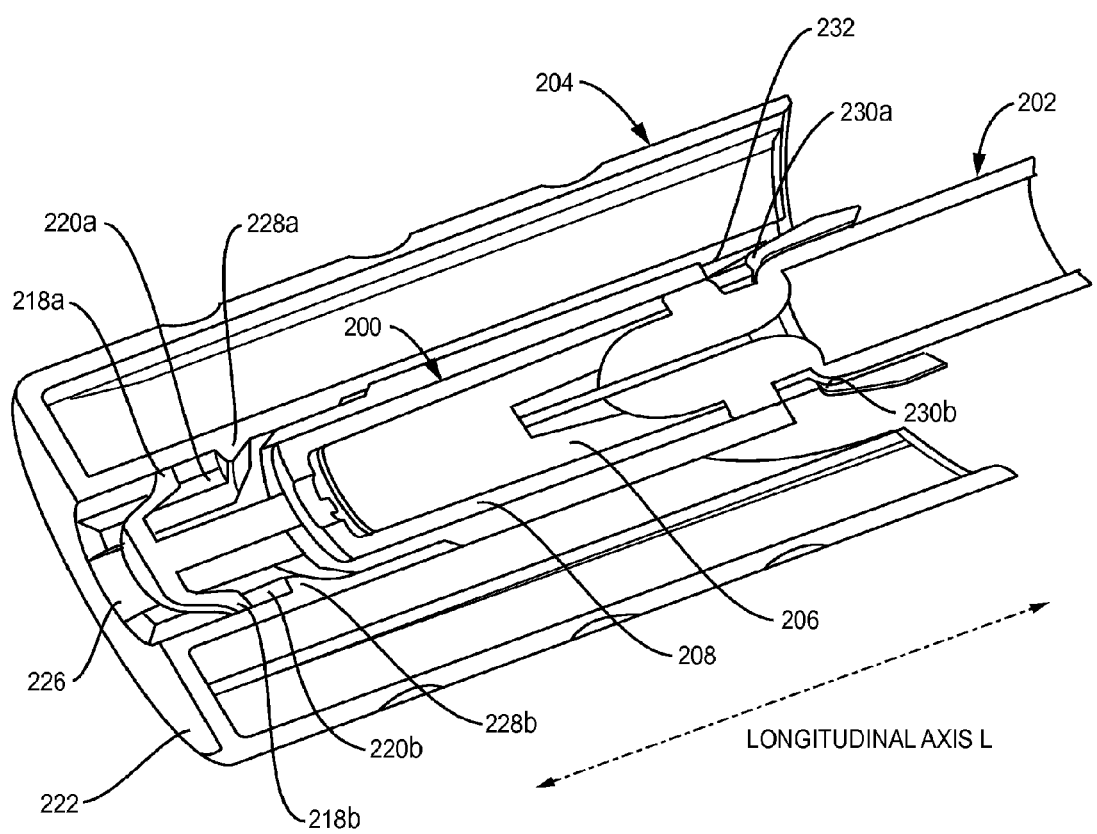
FIG. 2C illustrates a cross-sectional perspective view of the exemplary needle shield remover of FIGS. 2A and 2B engaged to a syringe and a distal cap.
Figure 2D:
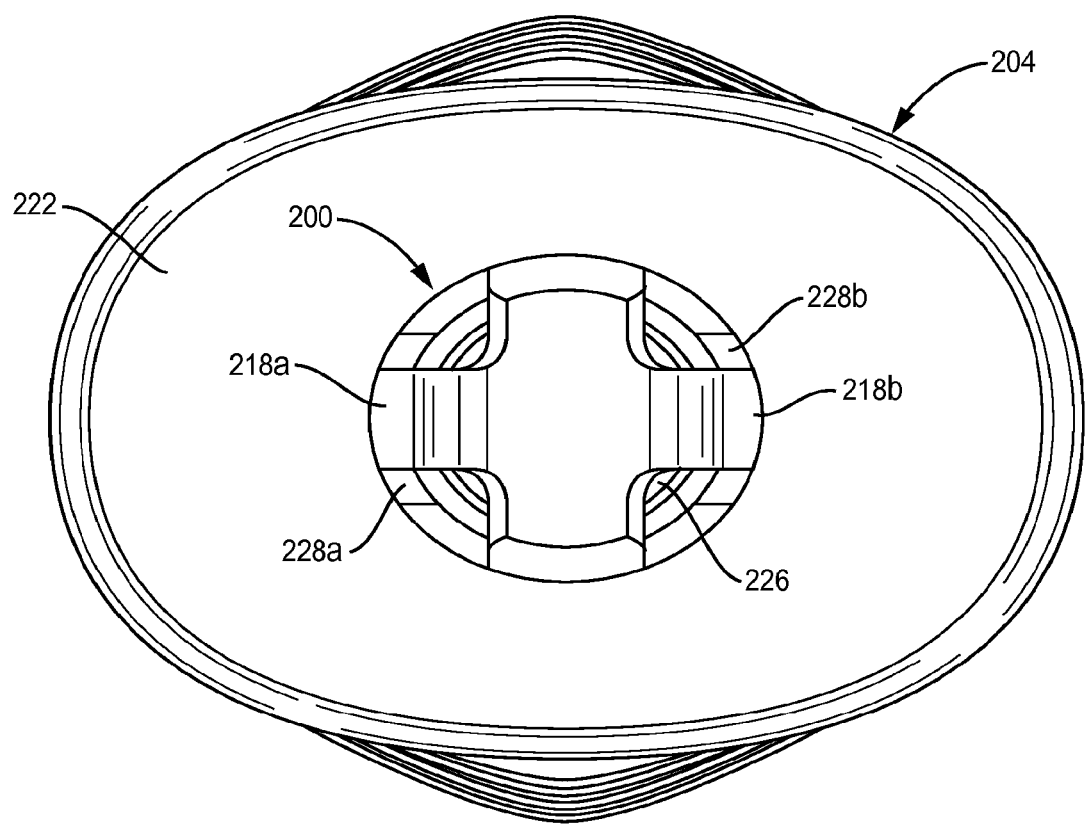
FIG. 2D is a bottom view of the exemplary distal cap of FIG. 2C showing engagement of the needle shield remover to the distal cap.

FIGS. 2A-2D illustrate an exemplary needle shield remover 200 engaged to a syringe 202 and to a distal cap 204. FIG. 2A illustrates a side view of an exemplary needle shield remover engaged to a syringe. FIG. 2B illustrates another side view of the exemplary needle shield remover of FIG. 2A rotated by about 90 degrees. FIG. 2C illustrates a cross-sectional perspective view of the exemplary needle shield remover of FIGS. 2A and 2B engaged to a syringe and a distal cap. FIG. 2D is a bottom view of the exemplary distal cap of FIG. 2C showing engagement of the needle shield remover to the distal cap. The length of an exemplary needle shield remover 200 may range from about 10 mm to about 50 mm, but is not limited to this exemplary range.

FIGS. 2A-2D are presented for the purpose of generally describing the structure, function and operation of an exemplary needle shield remover. Certain specific but non-limiting exemplary embodiments of needle shield removers are described in connection with FIGS. 5-24.

In the exemplary embodiment of FIGS. 2A-2D, an injection needle (not pictured) is coupled to the distal end of the syringe 202. The needle is covered with a soft needle shield 206 that is, in turn, positioned within and covered by a rigid needle shield 208. Portions of the soft needle shield 206 may extend through one or more apertures in the rigid needle shield 208 as shown in FIG. 2B. The exemplary needle shield remover 200 is positioned over the rigid needle shield 208. The needle shield remover 200 may be used to remove all of the needle shields when the needle shield remover 200 is removed from its engagement to the syringe 202.

The exemplary needle shield remover 200 may include a single tubular member. In other exemplary embodiments, the needle shield remover 200 may include two, three or more tubular members. In the exemplary embodiment illustrated in FIGS. 2A-2D, the exemplary needle shield remover 200 may include a proximal tubular member 210 that, at its distal edge, is integrally coupled to a distal tubular member 212 in some exemplary embodiments. The distal tubular member 212 may have a smaller outer diameter and a shorter length than the proximal tubular member 210, and may extend along a shorter length of the needle shield remover 200 along the longitudinal axis L than the proximal tubular member 210. A transition portion 214 may extend between the proximal tubular member 210 and the distal tubular member 212. An exemplary transition portion 214 may be a stepped transition, a ramped transition, or a combination of both.

The distal tubular member 212 may be substantially cylindrical in shape with a substantially circular or oval cross-section. At its distal end, the side wall of the distal tubular member 212 may include one or more platform structures that project longitudinally from the face of the distal tubular member 212 toward a removable distal cap. In an exemplary embodiment, a platform structure may include a first longitudinally-projecting portion 216a, a second longitudinally-projecting portion 216b, and a transverse portion 216c that extends between the longitudinally-projecting portions 216a, 216b at a distal end of the platform structure. The transverse portion 216c may support one or more cap engagement mechanisms in one exemplary embodiment.

At its distal end, an exemplary platform structure may support or define or provide one or more cap engagement mechanisms 218a, 218b that project radially outwardly from the platform structure. Exemplary cap engagement mechanisms may take the form of protrusions, teeth, clips, and other suitable engagement mechanisms. Exemplary cap engagement mechanisms 218a, 218b may have any suitable dimensions and structure. Exemplary lengths of the cap engagement mechanisms may include, but are not limited to, about 1, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.5, 7 mm, all intermediate numbers, and the like.

In the exemplary embodiment illustrated in FIGS. 2A and 2B, a first cap engagement mechanism 218a and a second cap engagement mechanism 218b are provided at opposite sides of the platform structure, i.e., separated from each other by about 180 degrees. In the exemplary embodiment illustrated in FIGS. 2A and 2B, the cap engagement mechanisms are provided separately and spaced from each other. In another exemplary embodiment, a single cap engagement mechanism may be provided to extend in an annular manner around the platform structure. One of ordinary skill in the art will recognize that exemplary needle shield removers may include any suitable number of cap engagement mechanisms extending from the platform structure including, but not limited to, one, two, three, four, five, six, seven, and the like.

A first end of each cap engagement mechanism 218a, 218b may be coupled to or may be provided integrally with the platform structure, and a second end of each cap engagement mechanism 218a, 218b may be suspended over a corresponding gap 220a, 220b between the second end of the cap engagement mechanism and the distal tubular member 212. During assembly of the needle shield remover 200 with a removable distal cap 204, provided to cover the needle shield remover, the cap engagement mechanisms 218a, 218b may be coupled to the cap 204 so that removal of the cap also automatically removes the needle shield remover 200.

FIG. 2C illustrates a cross-sectional perspective view of the removable distal cap 204 in which a central aperture 226 is provided along longitudinal axis L. FIG. 2D is a bottom view of a distal face 222 of the distal cap 204 showing engagement of the needle shield remover 200 to the distal cap 204. One or more inwardly-projecting stop portions 228a, 228b (e.g., flanges or raised edges) may be provided at the interior surface of the central aperture 226 of the distal cap 204. In the exemplary embodiment of FIGS. 2C and 2D, the inwardly-projecting stop portions 228a, 228b may not extend along the entire periphery of the central aperture 226.

In another exemplary embodiment, the inwardly-projecting stop portions may extend along the entire periphery of the central aperture 226.

As shown in FIG. 2C, the one or more cap engagement mechanisms 218a, 218b of the needle shield remover 200 may be made to fit through the aperture 226 of the distal cap 204. In this assembled configuration of the needle shield remover 200 and the distal cap 204, inwardly-projecting stop portions 228a, 228b (e.g., flanges or raised edges) provided in the aperture 226 of the distal cap 204 may be positioned reliably within the gap 220a, 220b of the needle shield remover 200. This allows the needle shield remover 200 to be reliably engaged to the distal cap 204 upon assembly and during removal of the cap 204 from the device housing, thus causing removal of the distal cap 204 from the device housing to automatically remove the needle shield remover 200 as well. Since the needle shield remover 200 is reliably engaged to one or more needle shields 206, 208, removal of the needle shield remover, in turn, automatically removes the needle shields as well.

The cap engagement mechanisms 218a, 218b may snap into place in the aperture 226 of the distal cap 204 so that the inwardly-projecting stop portions 228a, 228b are positioned within the gap 220a, 220b of the needle shield remover 200. In an exemplary embodiment, when the cap engagement mechanisms 218a, 218b are engaged with the distal cap 204, there may be a decrease in the force experienced against insertion of the distal cap 204 over the needle shield remover 200. In an exemplary embodiment, this decrease in the force may be sensed by a user or automatically by an assembly machine to determine that the inwardly-projecting stop portions 228a, 228b of the distal cap 204 have been reliably positioned within the gap 220a, 220b of the needle shield remover 200. In an exemplary embodiment, when the cap engagement mechanisms 218a, 218b are engaged with the distal cap 204, an audible "click" sound may be emitted to provide an audible indication that the distal cap 204 has been successfully engaged with the needle shield remover 200.

The proximal tubular member 210 of the needle shield remover 200 may be substantially cylindrical in shape with a substantially circular or oval cross-section. The side wall of the first tubular member 210 may enclose and define a substantially cylindrical cavity for housing the injection needle covered by the soft needle shield 206 and the rigid needle shield 208.

At or near its proximal edge, the side wall of the proximal tubular member 210 may define and/or include one or more inwardly-projecting shield engagement mechanisms 230a, 230b that are biased by the side wall to reliably remain positioned within a gap 232 formed between the body of the syringe 202 and the proximal edge of the rigid needle shield 208. In the exemplary embodiment of FIGS. 2A and 2B, a first inwardly-projecting shield engagement mechanism 230a and a second inwardly-projecting shield engagement mechanism 230b are provided at opposite sides of the needle shield remover 200, i.e., separated from each other by about 180 degrees.

The inwardly-projecting shield engagement mechanisms 230a, 230b may be positioned in the gap 232 during the assembly process and may reliably be positioned in the gap during the use of the device. When the removable distal cap covering the injection needle is removed before performing an injection (by pulling in the direction indicated by arrow R), the inwardly-projecting shield engagement mechanisms 230a, 230b exert force in the direction R against the peripheral edge of the rigid needle shield 208, thereby pulling the rigid needle shield 208 and the soft needle shield 206 away from the syringe body 202 in the direction R and exposing the injection needle for performing an injection.

Exemplary inwardly-projecting shield engagement mechanisms 230a, 230b may be configured to bias against the gap 232 with a sufficient force to ensure that when the needle shield remover is removed from the device, the needle shield remover 200 remains engaged with the rigid needle shield 208 and thereby reliably removes the rigid needle shield 208 from the body of the syringe 202. Exemplary inwardly-projecting shield engagement mechanisms 230a, 230b may be configured to interface with the gap 232 over a sufficient area or width to apply a sufficient force to remove the rigid needle shield when the needle shield remover is pulled away from the syringe. In exemplary embodiments, a width of an exemplary inwardly-projecting shield engagement mechanism 230a, 230b that interfaces with the gap 232 may range from about 3 mm to about 7 mm, but is not limited to this exemplary range. In an exemplary embodiment, the edge of the inwardly-projecting shield engagement mechanisms 230a, 230b that interfaces with the gap 232 may be substantially straight. In another exemplary embodiment, the edge of the inwardly-projecting shield engagement mechanisms 230a, 230b that interfaces with the gap 232 may be serrated.

In an exemplary embodiment, the inner diameter of the needle shield remover 200 at the inwardly-projecting shield engagement mechanisms 230a, 230b may be less than the outer diameter of the rigid needle shield 208. The inner diameter of the needle shield remover 200 at the inwardly-projecting shield engagement mechanisms 230a, 230b may also be less than the outer diameter of the syringe body 202. The inner diameter of the needle shield remover 200 at the inwardly-projecting shield engagement mechanisms 230a, 230b may be substantially equal to the outer diameter of the gap 232 formed between the syringe body and the proximal end of the rigid needle shield 208. This configuration of the inwardly-projecting shield engagement mechanisms 230a, 230b allows the shield engagement mechanisms to snap into place at the gap 232 in a reliable and tight manner so that disengagement requires a minimal threshold level of force. This configuration also prevents creep of the inwardly-projecting shield engagement mechanisms 230a, 230b out of the gap 232 before the needle shield remover 200 is pulled away from the syringe body.

An exemplary inner diameter of the needle shield remover 200 may range from about 5 mm to about 20 mm, but is not limited to this exemplary range. An exemplary inner diameter of the needle shield remover 200 may range from about 8 mm to about 11 mm in some exemplary embodiments. An exemplary inner diameter of the needle shield remover 200 may be about 8.5 mm in an exemplary embodiment. An exemplary inner diameter of the needle shield remover 200 may be about 11 mm in another exemplary embodiment.

The inwardly-projecting shield engagement mechanisms 230a, 230b may snap into place at the gap 232 as the needle shield remover 200 is inserted over the rigid needle shield 208. When the inwardly-projecting shield engagement mechanisms 230a, 230b snap into place at the gap 232, there may be a decrease in the force experienced against insertion of the needle shield remover 200 over the rigid needle shield 208. In an exemplary embodiment, this decrease in the force may be sensed by a user or automatically by an assembly machine to determine that the inwardly-projecting shield engagement mechanisms 230a, 230b have been successfully engaged to the gap 232. In an exemplary embodiment, the positioning of the inwardly-projecting shield engagement mechanisms 230a, 230b in the gap 232 may emit an audible "click" sound that provides an audible indication that the needle shield remover 200 has been successfully engaged with the rigid needle shield 208.

One of ordinary skill in the art will recognize that exemplary needle shield removers may include any suitable number of inwardly-projecting shield engagement mechanisms 230a, 230b including, but not limited to, one, two, three, four, five, six, seven, and the like. Exemplary inwardly-projecting shield engagement mechanisms may take the form of protrusions, teeth, clips, and other suitable engagement mechanisms.

In the exemplary embodiment illustrated in FIGS. 2A and 2B, the one or more inwardly-projecting shield engagement mechanisms 230a, 230b are configured and positioned to consistently and reliably fit within the gap 232 formed between the body of the syringe 202 and the proximal edge of the rigid needle shield 208. In another exemplary embodiment, one or more inwardly-projecting shield engagement mechanisms 230a, 230b may be configured and positioned to consistently and reliably engage with an aperture in the rigid needle shield 208 (for example, exemplary aperture 108 illustrated in FIG. 1A). This allows automatic removal of the rigid needle shield 208 (and an associated soft needle shield 206) by the inwardly-projecting shield engagement mechanisms 230a, 230b of the needle shield remover 200, when the needle shield remover 200 is removed from the device housing by its engagement with a distal cap 204 that is removed by a user.

In another exemplary embodiment, one or more inwardly-projecting shield engagement mechanisms 230a, 230b may be configured and positioned to consistently and reliably engage with a ridged portion in the rigid needle shield 208 (for example, exemplary ridged portion 110 illustrated in FIG. 1A). This allows automatic removal of the rigid needle shield 208 (and an associated soft needle shield 206) by the inwardly-projecting shield engagement mechanisms 230a, 230b of the needle shield remover 200, when the needle shield remover 200 is removed from the device housing by engagement of the needle shield remover 200 with a distal cap 204 that is removed by a user. In another exemplary embodiment in which the injection needle is covered by a soft needle shield 206 and lacks a rigid needle shield 208, one or more inwardly-projecting shield engagement mechanisms 230a, 230b of the needle shield remover 200 may be configured and positioned to consistently and reliably engage with the soft needle shield 206. One of ordinary skill in the art will recognize that the inwardly-projecting shield engagement mechanisms 230a, 230b may be configured and positioned to engage any other suitable component on the rigid needle shield 208 and/or the soft needle shield 206.

In the exemplary embodiment illustrated in FIGS. 2A and 2B, the inwardly-projecting shield engagement mechanisms 230a, 230b are provided in a component separate from the rigid needle shield 208 (i.e., in the needle shield remover 200), and the shield engagement mechanisms 230a, 230b are not permanently engaged with the rigid needle shield 208. In another exemplary embodiment, the inwardly-projecting shield engagement mechanisms 230a, 230b of the needle shield remover 200 may be permanently engaged with the rigid needle shield 208, for example, using glue or epoxy.

At or near its proximal edge, the side wall of the proximal tubular member 210 of the needle shield remover 200 may also define one or more cutout portions 234 for allowing a user to view the contents of the syringe 202 and/or to view an end-of-injection indicator from outside the device housing. That is, the cutout portions 234 of the proximal tubular member 210 may align with a transparent inspection window or inspection aperture provided in the device housing to allow a user to view the contents of the syringe 202 and/or to view an end-of-injection indicator from outside the device. In an exemplary embodiment, two exemplary cutout portions may be provided at opposite sides of the needle shield remover 200, i.e., separated from each other by about 180 degrees. In an exemplary embodiment, the cutout portions 234 may be provided in an alternating manner with the inwardly-projecting shield engagement mechanisms 230a, 230b, all of which may be provided at or near the proximal edge of the proximal tubular member 210. In an exemplary embodiment, each cutout portion 234 may have a substantially concave shape or a semicircular shape, but is not limited to these exemplary shapes.

An exemplary width of the cutout portions may range from about 3 mm to about 7 mm, but is not limited to this exemplary range. Exemplary widths of the cutout portions may include, but are not limited to, about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 mm, and the like.

One or more additional protrusions and/or grooves may be provided in the exterior surface of the proximal tubular member 210 and/or the distal tubular member 212 in order to facilitate engagement of the needle shield remover 200 with another component of the automatic injection device, e.g., a syringe sleeve that cooperatively engages with and covers a proximal portion of the needle shield remover 200, a removable cap 204 that covers a distal portion of the needle shield remover 200, and the like. For example, one or more longitudinally-extending grooves 236a, 236b may be provided in the exterior surface of the needle shield remover 200 to movably engage with a syringe sleeve. In an exemplary embodiment, the syringe sleeve may allow relative movement of the syringe sleeve and/or the needle shield remover 200 along the longitudinal axis L, but may hold the needle shield remover 200 in a substantially fixed axial orientation relative to the syringe sleeve. This ensures that the cutout portions 234 of the needle shield remover 200 are maintained in alignment with a transparent inspection window or inspection aperture provided in the syringe sleeve and with a transparent inspection window or inspection aperture provided in the device housing, thus allowing a user to view the contents of the syringe 202 and/or to view an end-of-injection indicator through the inspection windows or apertures. Certain exemplary embodiments of syringe sleeves are described in connection with FIGS. 3 and 4.

In the exemplary embodiment illustrated in FIGS. 2A-2C, the needle shield remover 200 may be provided as a separate component from the distal cap 204 of the automatic injection device. In another exemplary embodiment, a needle shield remover 200 may be provided integrally with the distal cap 204, for example, by integrally coupling the cap engagement mechanisms 218a, 218b of the needle shield remover 200 with the distal cap 204 of the device.

III. Exemplary Syringe Sleeves for use in Automatic Injection Devices

An exemplary automatic injection device may include a syringe sleeve that is a structural member for enveloping a portion of a syringe fitted with a needle shield remover. The syringe sleeve may be configured to hold and guide the syringe fitted with a needle shield remover, so that the syringe may move forwardly within and relative to the housing of the device from a retracted position (i.e., farther away from the injection site) to an injection position (i.e., closer to the injection site in which the injection needle projects from an open end of the device housing). The syringe may rest within the syringe sleeve, and both may be housed within the housing of the automatic injection device.

Other exemplary automatic injection devices may not provide a syringe sleeve.

An exemplary syringe sleeve may include a transparent inspection window or inspection aperture that may be aligned with both a cutout portion of the needle shield remover and an inspection window or inspection aperture provided the device housing, so that the contents of the syringe may be reliably viewed from outside the device housing. The syringe sleeve may maintain the needle shield remover in a substantially fixed axial orientation so that the cutout portion of the needle shield remover is aligned with the inspection window or inspection aperture of the syringe sleeve and the device housing. This ensures that movement of the needle shield remover within the device does not lead to obscuration of the inspection window or inspection aperture of the device housing.

The syringe sleeve may have any suitable configuration, shape and size suitable for accommodating the syringe fitted with the needle shield remover, and for axially orienting the cutout portion of the needle shield remover in alignment with the inspection window or inspection aperture of the device housing. The syringe sleeve may be formed of any suitable material including, but not limited to, thermoplastic polymers, e.g., polycarbonates.

Figure 3B:
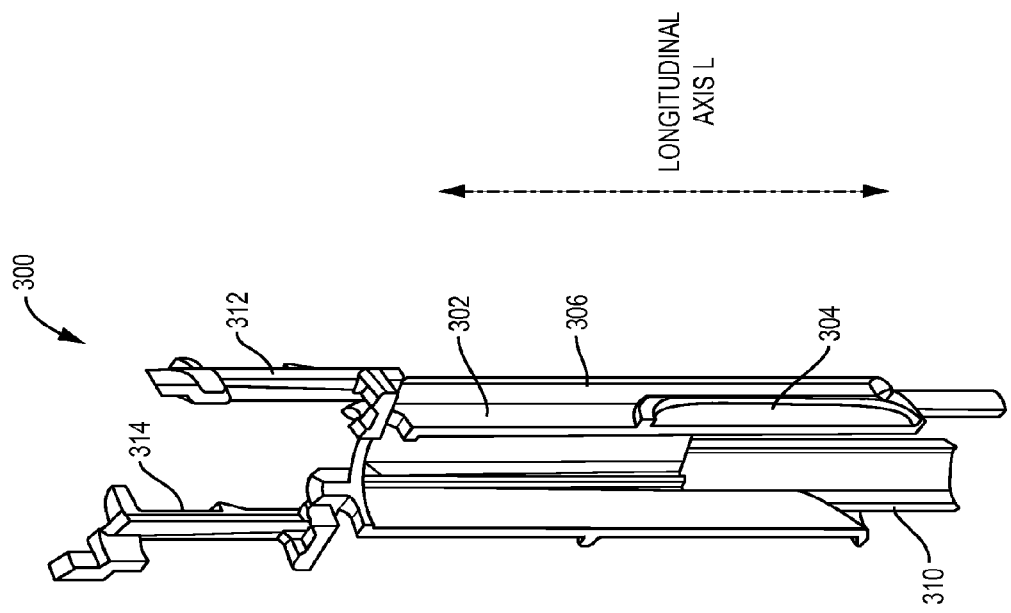
FIG. 3B illustrates a cross-sectional perspective view of the exemplary syringe sleeve of FIG. 3A bisected along a longitudinal axis L.
Figure 3A:
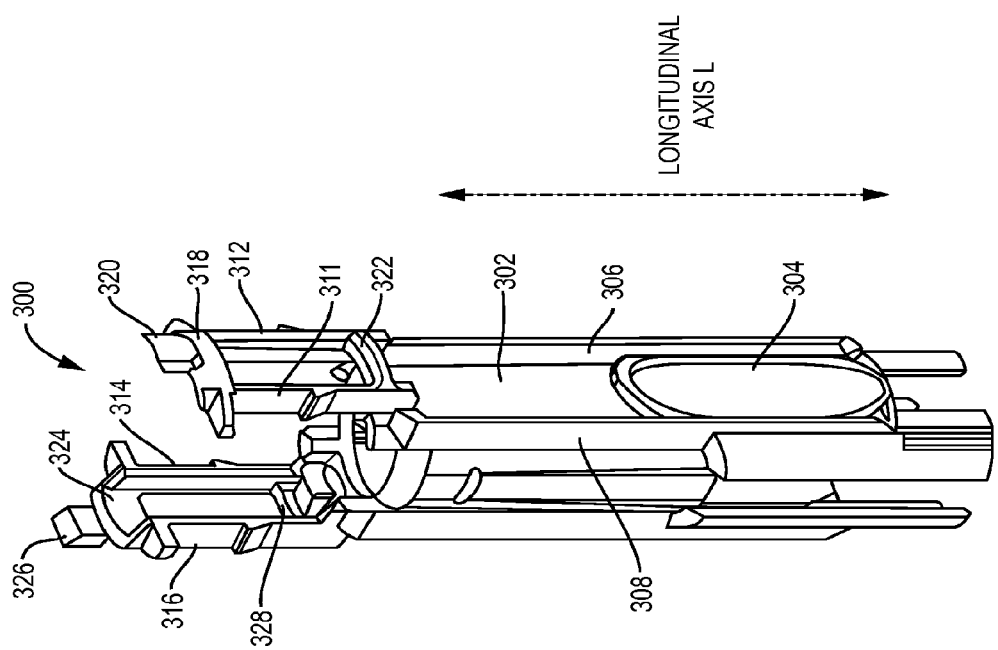
FIG. 3A illustrates a perspective view of an exemplary syringe sleeve.

FIG. 3A illustrates a perspective view of an exemplary syringe sleeve 300. FIG. 3B illustrates a cross-sectional perspective view of the exemplary syringe sleeve 300 bisected along a longitudinal axis L. The exemplary syringe sleeve 300 may include a tubular member 302 that may be substantially cylindrical in shape with a substantially circular or oval cross-section. The side wall of the tubular member 302 may enclose and define a substantially cylindrical cavity for housing a syringe fitted with a needle shield remover.

The side wall of the tubular member 302 may define and/or include one or more transparent inspection windows or inspection apertures 304 for allowing a user of the device to view the contents of the syringe and/or an indicator. The inspection window or inspection aperture of the tubular member 302 may be aligned with the cutout portion of the needle shield remover and with the inspection window or inspection aperture of the automatic injection device housing to provide a clear unobstructed view of the syringe contents and/or an indicator. The inspection window or inspection aperture 304 may have any suitable configuration, size and shape for allowing viewing of the contents of the syringe. Exemplary shapes of the inspection window or inspection aperture 304 may include, but are not limited to, a substantially elongated oval or elliptical shape, a substantially elongated rectangular shape, and the like. In an exemplary embodiment, the inspection window or inspection aperture 304 may have a longer length along the longitudinal axis L than a width along a transverse axis.

In an exemplary embodiment, the entire syringe sleeve 300 may be formed of a transparent material. In another exemplary embodiment, the inspection window or inspection aperture 304 may be the only component of the syringe sleeve 300 that is formed of a transparent material or is an aperture in the tubular member 302.

An exterior surface of the tubular member 302 may include one or more raised structures and/or grooves to engage with one or more other components of the automatic injection device. An exemplary raised structure may be one or more longitudinally-extending rails 306, 308 that may fit movably along internal longitudinally-extending grooves and/or protrusions (not pictured) provided on an interior surface of the device housing. The rails 306, 308 may allow the syringe sleeve 300 to move longitudinally relative to the device housing, and may allow the syringe sleeve 300 to be held in a fixed axial orientation relative to the device housing. In an exemplary embodiment, the rails 306, 308 may extend along the entire length of the tubular member 302. In exemplary embodiments, one, two, three, four, five, six rails may be provided in the exterior surface of the tubular member 302, but the number of rails is not limited to these exemplary numbers. Exemplary lengths of the rails 306, 308 or grooves and/or protrusions in the exterior surface of the tubular member 302 may range from about 1 mm to about 6 mm, but are not limited to this exemplary range.

An interior surface of the tubular member 302 may include one or more raised structures and/or grooves to engage with one or more other components of the automatic injection device. An exemplary raised structure may be one or more longitudinally-extending rails 310 that may fit movably along internal longitudinally-extending grooves and/or protrusions provided on an exterior surface of a needle shield remover. The rails 310 may allow the syringe sleeve 300 to move longitudinally relative to the needle shield remover and to allow the needle shield remover to move longitudinally relative to the syringe sleeve 300. The rails 310 may also allow the needle shield remover to be held in a fixed axial orientation relative to the syringe sleeve 300. The fixed axial orientation between the needle shield remover and the syringe sleeve 300 allows the cutout portion of the needle shield remover to be aligned with the inspection window or inspection aperture of the syringe sleeve 300 and with the inspection window or inspection aperture of the device housing. This ensures that the contents of the syringe may be reliably viewed at any time from the outside of the device through the inspection window or inspection aperture in the device housing. Exemplary lengths of the rails 310 or grooves on the interior surface of the tubular member 302 may range from about 1 mm to about 6 mm, but are not limited to this exemplary range.

A proximal portion of the tubular member 302 (farthest from the injection site) may be coupled to one or more longitudinally-extending syringe alignment guides 311, 312, 314, 316 for aligning a syringe in a substantially fixed axial orientation relative to the syringe sleeve 300. This ensures that the inspection window or inspection aperture 304 of the tubular member 302 is reliably aligned with a corresponding cutout portion of an exemplary needle shield remover attached to the syringe. One of ordinary skill in the art will recognize that any number of syringe alignment guides may be used in exemplary syringe sleeves.

In an exemplary embodiment, two pairs of syringe alignment guides may be provided so that the pairs are provided on opposite sides of the tubular member 302. In an exemplary embodiment, a first pair of guides may include a first syringe alignment guide 311 and a second syringe alignment guide 312. A second pair of guides may be provided on an opposite side of the tubular member 302 (i.e., offset from the first pair of guides by about 180 degrees), and may include a third syringe alignment guide 314 and a fourth syringe alignment guide 316.

At a proximal end of the alignment guides, the alignment guides 311 and 312 may be coupled to each other by a first beam 318 extending along a transverse axis between the alignment guides 311 and 312. In an exemplary embodiment, a tabbed foot 320 may extend outwardly from the first beam 318 to engage with the device housing. At a distal end of the alignment guides, the alignment guides 311 and 312 may be coupled together by a second flexible beam 322 extending along a transverse axis between the alignment guides 311 and 312. In an exemplary embodiment, the second flexible beam 322 may provide a stopping position for the proximal end of the syringe. That is, when a flanged proximal end of the syringe reaches the second flexible beam 322, the syringe may be prevented from farther movement toward the injection site as it has already achieved its injection position.

Similarly, at a proximal end of the alignment guides, the alignment guides 314 and 316 may be coupled to each other by a first beam 324 extending along a transverse axis between the alignment guides 314 and 316. In an exemplary embodiment, a tabbed foot 326 may extend outwardly from the first beam 324 to engage with the device housing. At a distal end of the alignment guides, the alignment guides 314 and 316 may be coupled together by a second flexible beam 328 extending along a transverse axis between the alignment guides 314 and 316. In an exemplary embodiment, the second flexible beam 328 may provide a stopping position for the proximal end of the syringe. That is, when a flanged proximal end of the syringe reaches the second flexible beam 328, the syringe may be prevented from farther movement toward the injection site as it has already achieved its injection position.

Figure 4A:
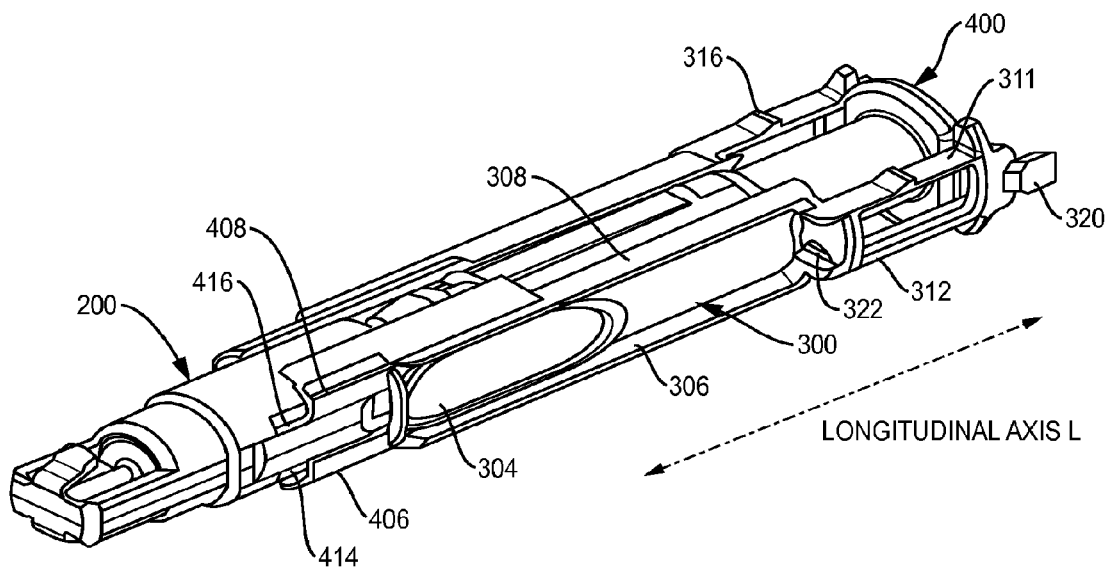
FIG. 4A illustrates a perspective view of an assembly of an exemplary syringe sleeve housing an exemplary syringe that is fitted with an exemplary needle shield remover.

FIG. 4A illustrates a perspective view of an assembly of an exemplary syringe sleeve 300 housing an exemplary syringe 400 that is fitted with an exemplary needle shield remover 200 at its distal end. The syringe alignment guides 311, 312, 314, 316 provided at the proximal portion of the syringe sleeve 300 may align the syringe 400 and hold it in a substantially fixed axial orientation relative to the syringe sleeve 300. As shown in FIG. 4A, the needle shield remover 200 and the syringe sleeve 300 overlap each other at some portions, such that the inspection window or inspection aperture 304 of the syringe sleeve 300 overlaps and is aligned with a cutout portion of the needle shield remover 200.

Figure 4B:
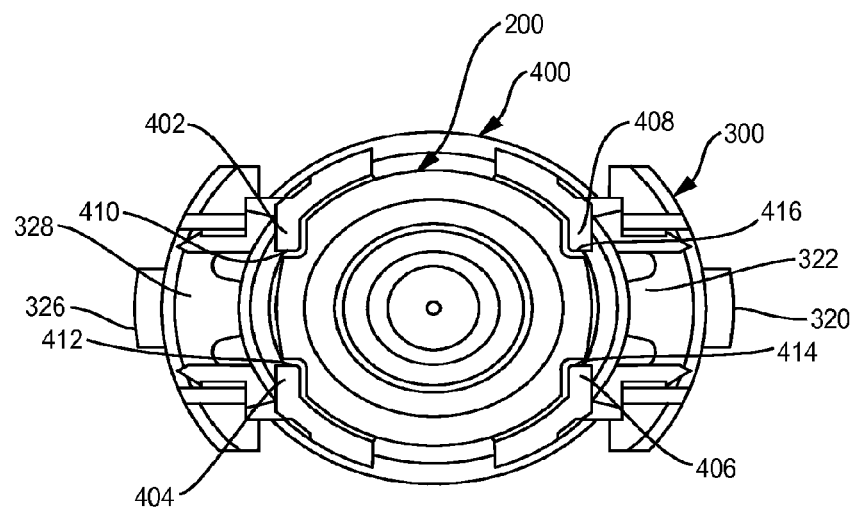
FIG. 4B illustrates a transverse cross-sectional view of the exemplary assembly of FIG. 4A.

FIG. 4B illustrates a transverse cross-sectional view of an exemplary assembly in which an exemplary syringe sleeve 300 that houses an exemplary syringe 400 fitted with an exemplary needle shield remover 200. The exemplary syringe sleeve 300 includes four exemplary longitudinally-extending rails 402, 404, 406, 408 on an interior surface of the exemplary syringe sleeve 300. The syringe sleeve 300 partially encloses an exemplary needle shield remover 200 including four corresponding longitudinal grooves 410, 412, 414, 416, respectively. Each rail of the syringe sleeve 300 may engage with a corresponding groove of the needle shield remover 200, so that the needle shield remover 200 is held in a substantially fixed axial orientation relative to the syringe sleeve 300.

Exemplary components illustrated in FIGS. 4A and 4B that are common to the components illustrated in FIGS. 3A and 3B are described in connection with FIGS. 3A and 3B.

One of ordinary skill in the art will recognize that syringe sleeves other than the exemplary syringe sleeve illustrated in FIGS. 3A, 3B, 4A and 4B may be used in exemplary automatic injection devices.

IV. First Non-Limiting Exemplary Embodiment of a Needle Shield Remover

FIGS. 5A and 5B illustrate an exemplary needle shield remover 500 having two exemplary inwardly-projecting shield engagement mechanisms for engagement with a rigid needle shield. FIG. 5A illustrates a perspective view of the exemplary needle shield remover 500. FIG. 5B illustrates a cross-sectional perspective view of the exemplary needle shield remover 500 of FIG. 5A bisected along a longitudinal axis L.

The exemplary needle shield remover 500 may include a proximal tubular member 502 that, at its distal edge, is integrally coupled to a distal tubular member 504 in some exemplary embodiments. The distal tubular member 504 may have a smaller diameter and a shorter length than the proximal tubular member 502, and may extend along a shorter length of the needle shield remover 500 along the longitudinal axis L than the proximal tubular member 502. A transition portion 506 may extend between the proximal tubular member 502 and the distal tubular member 504. An exemplary transition portion 506 may be a stepped transition, a ramped transition, or a combination of both.

The distal tubular member 504 of the needle shield remover 500 may be substantially cylindrical in shape with a substantially circular or oval cross-section. At its distal end, the side wall of the distal tubular member 504 may include one or more platform structures that project longitudinally from the face of the distal tubular member 504 toward a removable distal cap. In an exemplary embodiment, a platform structure may include a first longitudinally-projecting portion 508a, a second longitudinally-projecting portion 508b, and a transverse portion 508c that extends between the longitudinally-projecting portions 508a, 508b at a distal end of the platform structure. The transverse portion 508c may support one or more cap engagement mechanisms in one exemplary embodiment.

At its distal end, an exemplary platform structure may support or define or provide a first outwardly-projecting flexible cap engagement mechanism 510a and a second outwardly-projecting flexible cap engagement mechanism 510b that project radially outwardly from the platform structure. Exemplary cap engagement mechanisms may be any suitable protrusion, projection, teeth, and the like. In the exemplary embodiment of FIGS. 5A and 5B, the cap engagement mechanisms 510a, 510b are provided at opposite sides of the platform structure, i.e., separated from each other by about 180 degrees. One of ordinary skill in the art will recognize that exemplary needle shield removers may include any suitable number of cap engagement mechanisms extending from the platform structure including, but not limited to, one, two, three, four, five, six, seven, and the like.

A first end of each cap engagement mechanisms 510a, 510b may be coupled to or may be provided integrally with the platform structure, and a second end of each cap engagement mechanism 510a, 510b may be suspended over a gap 512a, 512b between the cap engagement mechanisms 510a, 510b and the distal tubular member 504. During assembly of the needle shield remover 500 with a distal cap of the automatic injection device (not pictured) provided to cover the needle shield remover, the cap engagement mechanisms 510a, 510b may be coupled to the distal cap so that removal of the cap also automatically removes the needle shield remover 500. In an exemplary embodiment, the cap engagement mechanisms 510a, 510b of the needle shield remover 500 may be inserted to fit within a central aperture provided in the distal cap such that one or more inwardly-projecting stop portions (e.g., flanges or raised edges) provided in the central aperture of the distal cap reliably engage the gaps 512a, 512b of the needle shield remover 500. This engagement allows the needle shield remover 500 to be reliably engaged to the distal cap after assembly and during removal of the distal cap from the device housing, thus causing removal of the distal cap from the device housing to automatically remove the needle shield remover 500 as well. Since the needle shield remover 500 is reliably engaged to one or more needle shields, removal of the needle shield remover, in turn, automatically removes the needle shields coupled to a syringe.

In the exemplary embodiment illustrated in FIGS. 5A and 5B, the needle shield remover 500 may be provided as a separate component from a distal cap of the automatic injection device. In another exemplary embodiment, a needle shield remover may be provided integrally with the distal cap, for example, by integrally coupling the cap engagement mechanisms 510*a*, 510*b* of the needle shield remover 500 with the distal cap of the device.

The proximal tubular member 502 of the needle shield remover 500 may be substantially cylindrical in shape with a substantially circular or oval cross-section. The side wall of the proximal tubular member 502 may enclose and define a substantially cylindrical cavity 514 for housing the injection needle covered by a soft needle shield and/or a rigid needle shield coupled to a syringe.

At or near its proximal edge, the side wall of the proximal tubular member 502 may define and/or include a first inwardly-projecting shield engagement mechanisms 516*a* and a second inwardly-projecting shield engagement mechanism 516*b*. The first and second inwardly-projecting shield engagement mechanisms 516*a*, 516*b* may be biased by the side wall to reliably remain positioned within a gap formed between the body of a syringe and the proximal edge of a rigid needle shield. Exemplary inwardly-projecting shield engagement mechanisms 516*a*, 516*b* may be any suitable protrusion, projection, teeth, and the like. In the exemplary embodiment of FIGS. 5A and 5B, the exemplary inwardly-projecting shield engagement mechanisms 516*a*, 516*b* are provided at opposite sides of the needle shield remover 500, i.e., separated from each other by about 180 degrees. The inwardly-projecting shield engagement mechanisms 516*a*, 516*b* may be positioned in a gap formed between a syringe body and a rigid needle shield during the assembly process, and may reliably be positioned in the gap during the use of the device. When a distal cap covering the injection needle is removed before performing an injection (by pulling in the direction indicated by arrow R), the inwardly-projecting shield engagement mechanisms 516*a*, 516*b* exert force in the direction R against the peripheral edge of the rigid needle shield, thereby pulling the rigid needle shield and the soft needle shield away from the syringe body in the direction R and exposing the injection needle for performing an injection.

In an exemplary configuration, each inwardly-projecting shield engagement mechanisms 516*a*, 516*b* may be situated at an aperture 518*a*, 518*b* in the proximal tubular member 502. Each inwardly-projecting shield engagement mechanisms 516*a*, 516*b* may include a first inclined or radial wall 520*a*, 520*b* that extends from a proximal base wall of the aperture 518*a*, 518*b* and projects inwardly into the cavity 514 at a first angle relative to the longitudinal axis L. The first inclined or radial wall 520*a*, 520*b* may be coupled to or may be integrally formed with an inwardly-projecting second inclined or radial wall 522*a*, 522*b*. The second inclined or radial wall 522*a*, 522*b* may extend from the first inclined or radial wall inwardly into the cavity 514 at a second angle relative to the longitudinal axis L.

In an exemplary embodiment, the second angle corresponding to the second inclined or radial wall 522*a*, 522*b* may be substantially greater than the first angle corresponding to the first inclined or radial wall 520*a*, 520*b*, so that the first inclined or radial wall 520*a*, 520*b* extends substantially along the longitudinal axis L and the second inclined or radial wall 522*a*, 522*b* extends substantially orthogonally to the longitudinal axis L. An exemplary first angle may range from about 0 degree to about 20 degrees relative to the longitudinal axis L toward the cavity 514. An exemplary second angle may range from about 30 degrees to about 60 degrees relative to the longitudinal axis L toward the cavity 514.

Providing the shield engagement mechanisms 516*a*, 516*b* as part of the proximal tubular member 502 facilitates robust assembly of the needle shield remover 500 in the automatic injection device. Projection of the inclined or radial walls of the shield engagement mechanisms 516*a*, 516*b* from the proximal base wall of the aperture 518*a*, 518*b* inwardly into the cavity 514 also facilitates robust assembly of the needle shield remover 500 in the device. These structural features, for example, allow the inclined or radial walls of the needle shield remover 500 to move radially outwardly with respect to the proximal tubular member 502, while minimizing a radially outward movement of the proximal tubular member 502 at the shield engagement mechanisms 516*a*, 516*b*, as the needle shield remover 500 is inserted coaxially over a needle shield during assembly. That is, expansion of the outer diameter of the needle shield remover 500 is minimized during assembly in order to minimize the risk of the shield engagement mechanisms 516*a*, 516*b* not being positioned at the gap between the needle shield and the syringe body and to minimize the risk of the shield engagement mechanisms 516*a*, 516*b* from becoming disengaged from the gap between the needle shield and the syringe body.

Certain conventional needle shield removers include shield engagement mechanisms that are not formed as a part of a tubular member. In addition, in certain conventional needle shield removers, the shield engagement mechanisms do not extend from a proximal base edge of an aperture or support mechanism. These conventional needle shield removers do not minimize a radially outward movement needle shield removers at the shield engagement mechanisms. This radially outward movement of the conventional needle shield removers reduces the robustness of the assembly process as it increases the risk of positioning the shield engagement mechanisms outside a gap formed between the syringe body and the needle shield.

Exemplary first and second inclined or radial walls may have any suitable dimension and structure. Exemplary lengths and widths of the first and second inclined or radial walls may include, but are not limited to, about 1, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.5, 7 mm, all intermediate numbers, and the like.

The second inclined or radial walls 522*a*, 522*b* of the inwardly-projecting shield engagement mechanisms 516*a*, 516*b* may be configured to be positioned within a gap formed between a syringe body and a proximal edge of a rigid needle shield. Each second inclined or radial wall 522*a*, 522*b* may have a peripheral edge 524*a*, 524*b* with a width that provides a sufficiently large interface with the rigid needle shield. In exemplary embodiments, the width of the peripheral edge 524*a*, 524*b* may range from about 3 mm to about 7 mm, but is not limited to this exemplary range. In an exemplary embodiment, the width is about 4.00 mm.

In an exemplary embodiment, the inwardly-projecting first and second inclined or radial walls 520*a*, 520*b*, 522*a*, 522*b* cause the inner diameter of the needle shield remover 500 at the inwardly-projecting shield engagement mechanisms 516a, 516b to be less than the outer diameter of the proximal end of the rigid needle shield. In an exemplary embodiment, the inwardly-projecting first and second inclined or radial walls 520a, 520b, 522a, 522b cause the inner diameter of the needle shield remover 500 at the inwardly-projecting shield engagement mechanisms 516a, 516b to be less than the outer diameter of the syringe body. The inner diameter of the needle shield remover 500 at the inwardly-projecting shield engagement mechanisms 516a, 516b may be substantially equal to the outer diameter of the gap formed between the syringe body and the proximal end of the rigid needle shield. This configuration of the inwardly-projecting shield engagement mechanisms 516a, 516b thereby allows the second inclined or radial walls 522a, 522b to snap into place at the gap in a reliable and tight manner so that disengagement requires at least a minimal threshold level of force. This configuration also prevents creep of the second inclined or radial walls 522a, 522b out of the gap after assembly but before removal by a user.

The inwardly-projecting shield engagement mechanisms 516a, 516b may snap into place at the gap formed between the rigid needle shield and the syringe body, as the needle shield remover 500 is inserted over the rigid needle shield. When the inwardly-projecting shield engagement mechanisms 516a, 516b snap into place at the gap, there may be a decrease in the force experienced against insertion of the needle shield remover 500 over the rigid needle shield. In an exemplary embodiment, this decrease in the force may be sensed by a user or automatically by an assembly machine to determine that the inwardly-projecting shield engagement mechanisms 516a, 516b have been successfully engaged to the gap formed between the rigid needle shield and the syringe body. In an exemplary embodiment, the positioning of the inwardly-projecting shield engagement mechanisms 516a, 516b in the gap may emit an audible "click" sound that provides an audible indication that the needle shield remover 500 has been successfully engaged with the rigid needle shield.

In the exemplary embodiment illustrated in FIGS. 5A and 5B, the needle shield remover 500 may be provided as a separate component from a needle shield of the automatic injection device. In another exemplary embodiment, a needle shield remover may be provided integrally with the rigid needle shield, for example, by integrally coupling the inwardly-projecting shield engagement mechanisms 516a, 516b of the needle shield remover 500 with the rigid needle shield.

At or near its proximal edge, the side wall of the proximal tubular member 502 may also define one or more cutout portions 526a, 526b for allowing a user to view of the contents of the syringe and/or to view an indicator from outside the device housing. That is, the cutout portions 526a, 526b of the proximal tubular member 502 align with a transparent inspection window or inspection aperture of the device housing to allow a user to view the syringe contents and/or to view an indicator from outside the device. In the exemplary embodiment of FIGS. 5A and 5B, a first cutout portion 526a and a second cutout portion 526b are provided at opposite sides of the needle shield remover 500, i.e., separated from each other by about 180 degrees. In an exemplary embodiment, the cutout portions 526a, 526b may be provided in an alternating manner with the inwardly-projecting shield engagement mechanisms 516a, 516b, all of which are provided at or near the proximal edge of the proximal tubular member 502. In an exemplary embodiment, each cutout portion 526a, 526b may take a substantially concave shape or a semicircular shape, but is not limited to these exemplary shapes.

In an exemplary embodiment, one or more additional protrusions and/or grooves may be provided in the exterior surface of the proximal tubular member 502 and/or the distal tubular member 504 in order to facilitate engagement of the needle shield remover 500 with another component of the automatic injection device, e.g., a syringe sleeve that cooperatively engages with and covers a proximal portion of the needle shield remover, a removable cap that covers a distal portion of the needle shield remover, and the like. For example, one or more longitudinally-extending grooves 528a, 528b may be provided in the exterior surface of the needle shield remover 500 to movably engage with a syringe sleeve. In an exemplary embodiment, the syringe sleeve may allow relative movement of the syringe sleeve and/or the needle shield remover along the longitudinal axis L, but may hold the needle shield remover in a substantially fixed axial orientation relative to the syringe sleeve. This ensures that the cutout portions 526a, 526b of the needle shield remover 500 are maintained in alignment with a transparent inspection window or inspection aperture of the syringe sleeve and with a transparent inspection window or inspection aperture of the device housing, thus allowing a user to view the contents of the syringe and/or to view an indicator through the inspection windows or inspection apertures.

Figure 6:
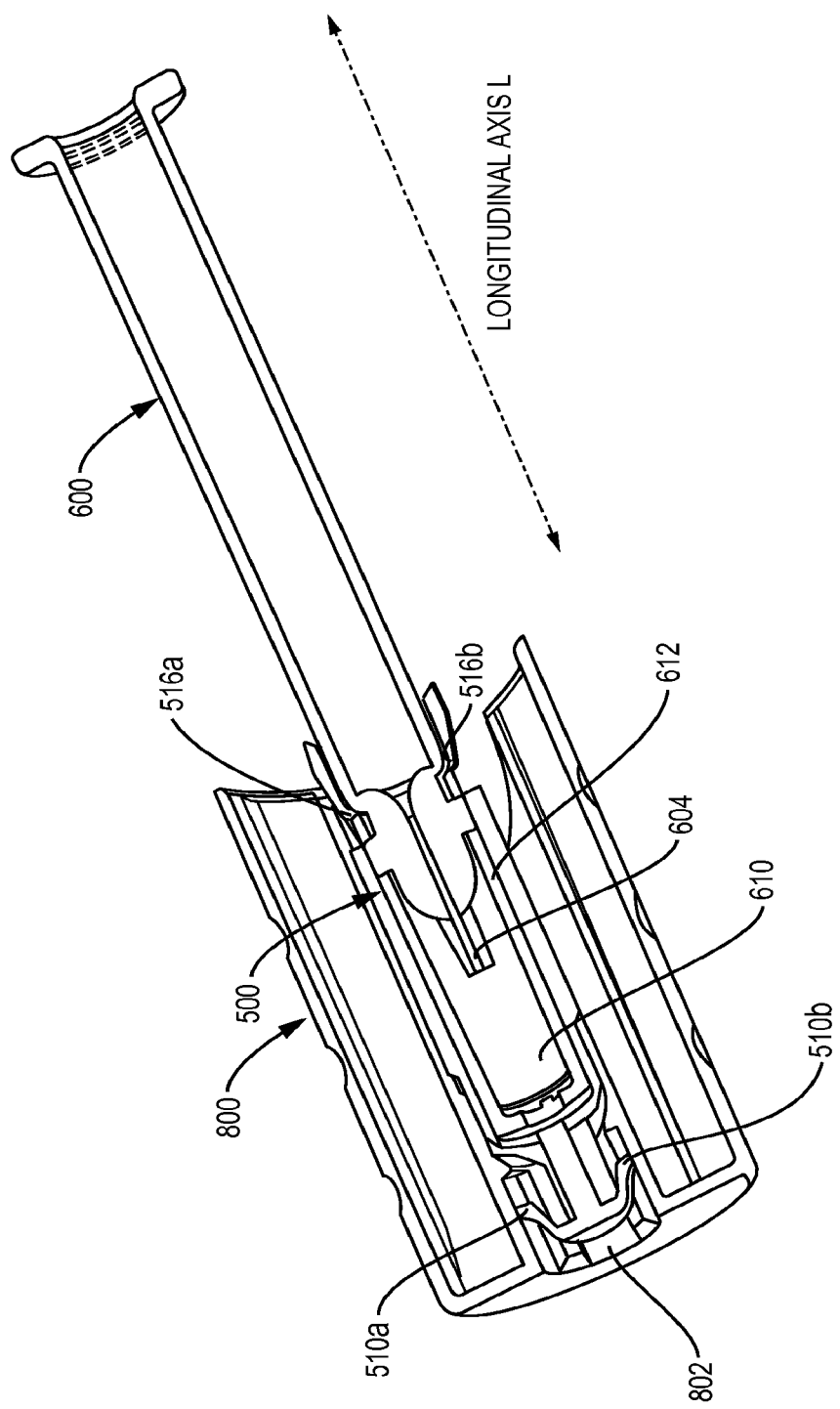
FIG. 6 illustrates a cross-sectional perspective view of the exemplary needle shield remover of FIGS. 5A and 5B assembled with a syringe and a distal cap.
Figure 7:
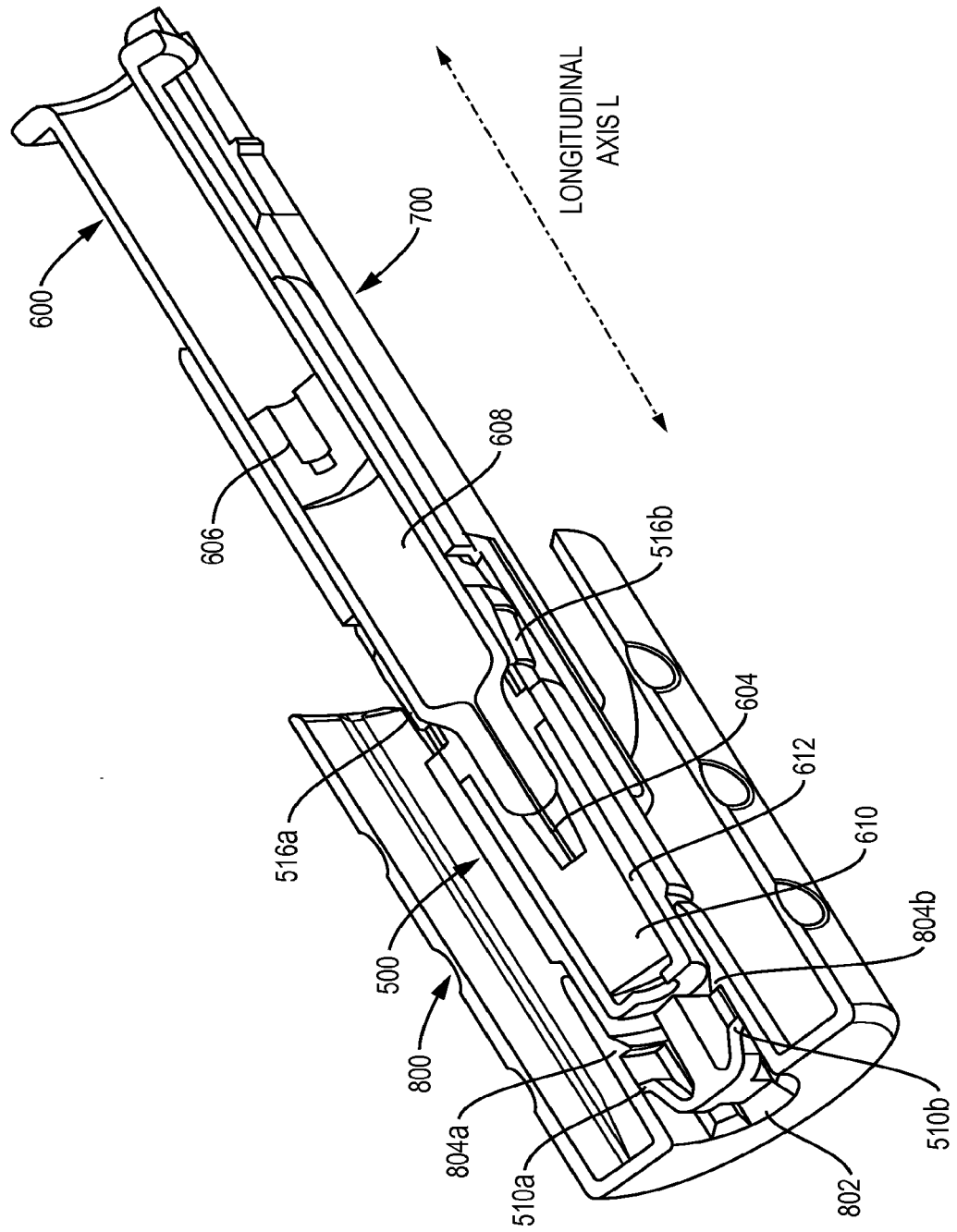
FIG. 7 illustrates a cross-sectional perspective view of the exemplary needle shield remover of FIGS. 5A and 5B assembled with a syringe, a distal cap and a syringe sleeve.
Figure 8:
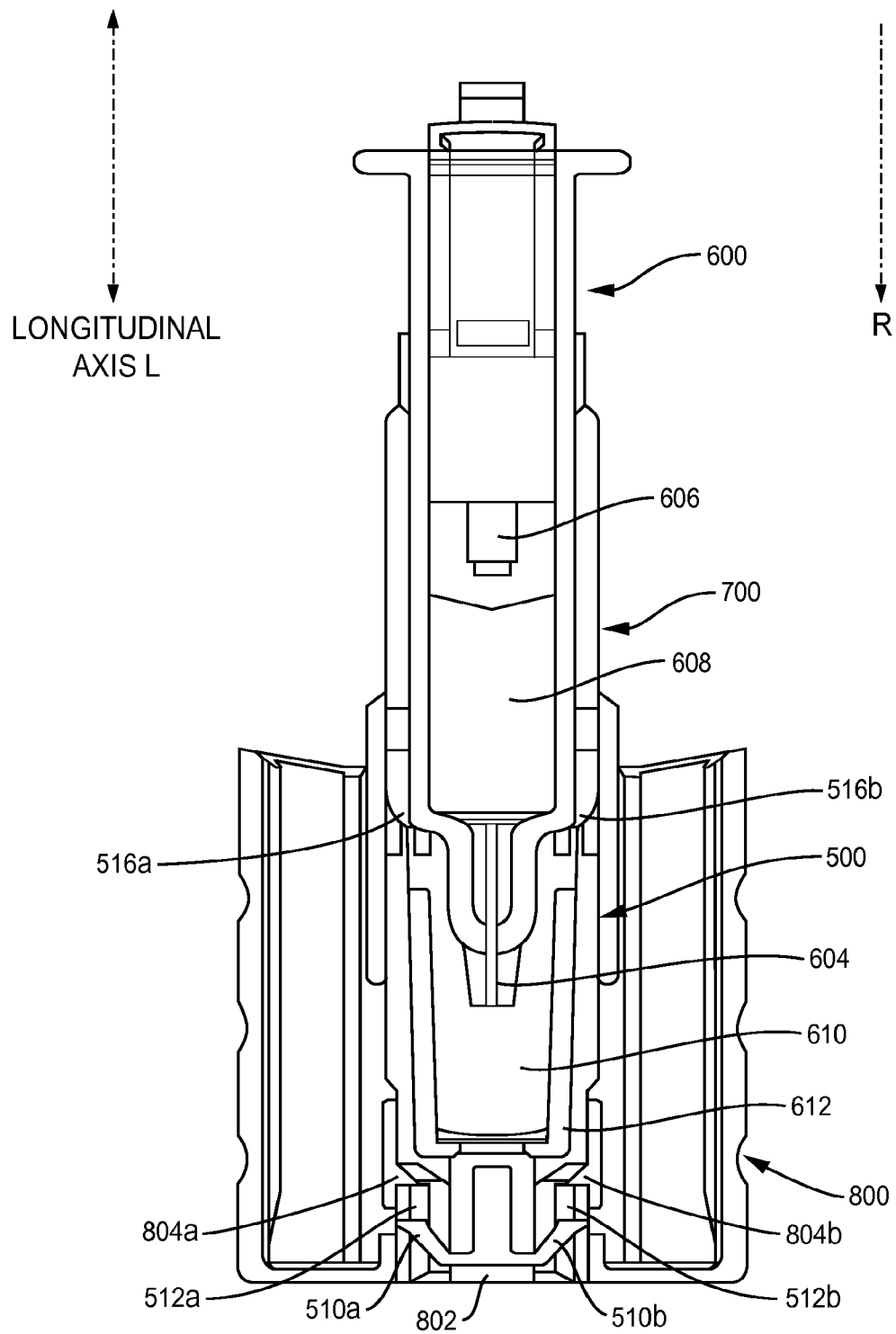
FIG. 8 illustrates a front cross-sectional view of the exemplary assembly of FIG. 7.
Figure 9:
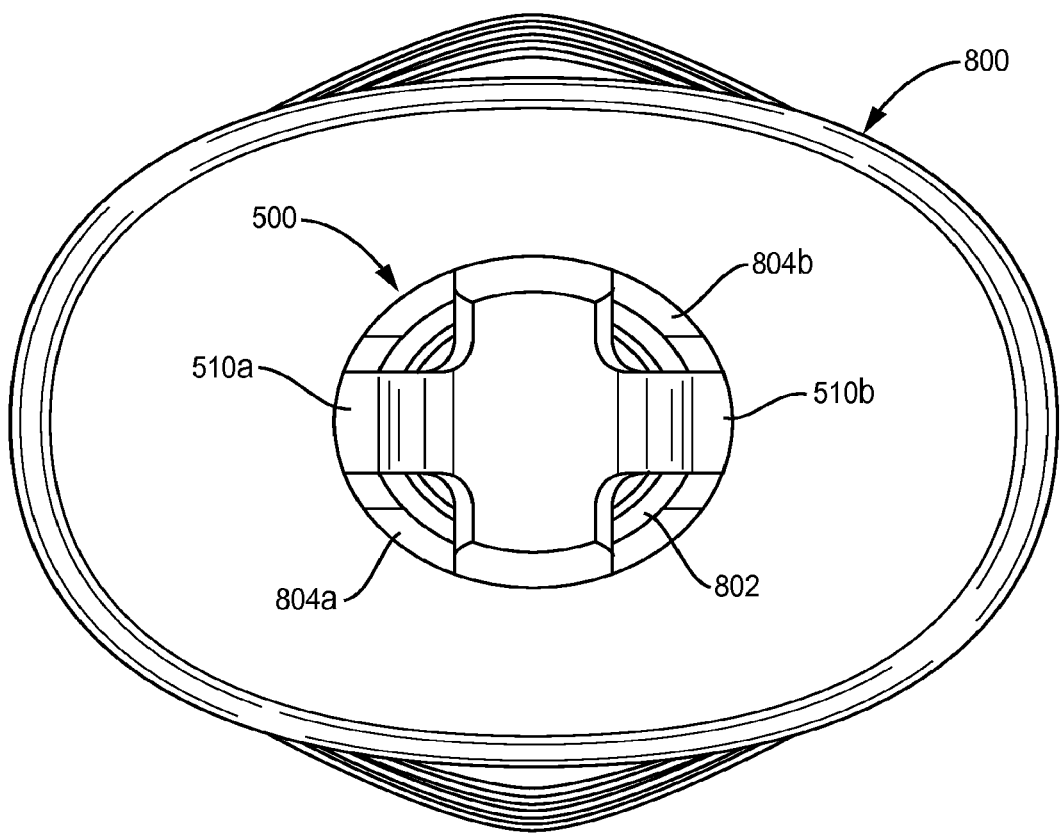
FIG. 9 illustrates a bottom view of an exemplary distal cap that is applicable to FIGS. 6-8.

FIG. 6 illustrates a cross-sectional perspective view of the exemplary needle shield remover 500 of FIGS. 5A and 5B assembled with a syringe 600 and a distal cap 800. In the exemplary embodiment of FIG. 6, the assembly lacks a syringe sleeve. FIG. 7 illustrates a cross-sectional perspective view of the exemplary needle shield remover 500 of FIGS. 5A and 5B assembled with a syringe 600 and a distal cap 800. In the exemplary embodiment of FIG. 7, the assembly includes a syringe sleeve 700. FIG. 8 illustrates a front cross-sectional view of the exemplary assembly of FIG. 7 including a syringe sleeve 700. FIG. 9 illustrates a bottom view of an exemplary distal cap 800 that is applicable to FIGS. 6-8.

An injection needle 604 may be affixed to a distal end of the syringe 600, a bung 606 may be disposed within the syringe 600, and a dose of a therapeutic agent 608 may be provided to fill the syringe 600. The injection needle 604 may be covered with a soft needle shield 610 and a rigid needle shield 612 disposed over the soft needle shield 610. The exemplary needle shield remover 500 may be disposed over the rigid needle shield 612 so that the inwardly-projecting shield engagement mechanisms 516a, 516b of the needle shield remover 500 fit within a gap between the rigid needle shield 612 and the body of the syringe 600. The cap engagement mechanisms 510a, 510b of the needle shield remover 500 may engage with a distal cap 800 provided to cover the distal portion of the device. In an exemplary embodiment, the cap engagement mechanisms 510a, 510b may be accommodated within a central aperture 802 provided in the distal cap 800, so that one or more inwardly-projecting stop portions 804a, 804b (e.g., flanges or raised edges) provided in the central apertures 802 of the distal cap 800 are positioned reliably within gaps 512a, 512b proximal to the cap engagement mechanisms 510a, 510b. In an exemplary embodiment, a single stop portion may extend radially around the periphery of the central aperture 802.

In the exemplary embodiment illustrated in FIGS. 7 and 8, a syringe sleeve 700 may be provided over the syringe 600 and the needle shield remover 500 to maintain the needle shield remover 500 in a substantially fixed axial orientation with the device housing.

Exemplary components illustrated in FIGS. 6-9 that are common to the components illustrated in FIGS. 2-3 are described in connection with FIGS. 2-3.

V. Second Non-Limiting Exemplary Embodiment of a Needle Shield Remover

FIGS. 10A and 10B illustrate an exemplary needle shield remover 1000 having two exemplary inwardly-projecting shield engagement mechanisms for engagement with a rigid needle shield. FIG. 10A illustrates a perspective view of the exemplary needle shield remover 1000. FIG. 10B illustrates a cross-sectional perspective view of the exemplary needle shield remover 1000 bisected along a longitudinal axis L.

The exemplary needle shield remover 1000 may include a proximal tubular member 1002 that, at its distal edge, is integrally coupled to a distal tubular member 1004 in some exemplary embodiments. The distal tubular member 1004 may have a smaller diameter and a shorter length than the proximal tubular member 1002, and may extend along a shorter length of the needle shield remover 1000 along the longitudinal axis L than the proximal tubular member 1002. A transition portion 1006 may extend between the proximal tubular member 1002 and the distal tubular member 1004. An exemplary transition portion 1006 may be a stepped transition, a ramped transition, or a combination of both.

The distal tubular member 1004 of the needle shield remover 1000 may be substantially cylindrical in shape with a substantially circular or oval cross-section. At its distal end, the side wall of the distal tubular member 1004 may include one or more platform structures that project longitudinally from the face of the distal tubular member 1004 toward a removable distal cap. In an exemplary embodiment, a platform structure may include a first longitudinally-projecting portion 1008a, a second longitudinally-projecting portion 1008b, and a transverse portion 1008c that extends between the first and second longitudinally-projecting portions 1008a, 1008b at the distal end of the platform structure. The transverse portion 1008c may support one or more cap engagement mechanisms in one exemplary embodiment.

At its distal end, an exemplary platform structure may support or define or provide a first outwardly-projecting flexible cap engagement mechanism 1010a and a second outwardly-projecting flexible cap engagement mechanism 1010b that project radially outwardly from the platform structure. Exemplary cap engagement mechanisms may be any suitable protrusion, projection, teeth, and the like. In the exemplary embodiment of FIGS. 10A and 10B, the cap engagement mechanisms 1010a, 1010b are provided at opposite sides of the platform structure, i.e., separated from each other by about 180 degrees. One of ordinary skill in the art will recognize that exemplary needle shield removers may include any suitable number of cap engagement mechanisms extending from the platform structure including, but not limited to, one, two, three, four, five, six, seven, and the like.

A first end of each cap engagement mechanisms 1010a, 1010b may be coupled to or may be provided integrally with the platform structure, and a second end of each cap engagement mechanism 1010a, 1010b may be suspended over a gap 1012a, 1012b between the cap engagement mechanisms 1010a, 1010b and the distal tubular member 1004. During assembly of the needle shield remover 1000 with a distal cap of the automatic injection device (not pictured) provided to cover the needle shield remover, the cap engagement mechanisms 1010a, 1010b may be coupled to the distal cap so that removal of the cap also automatically removes the needle shield remover 1000.

In an exemplary embodiment, the cap engagement mechanisms 1010a, 1010b of the needle shield remover 1000 may be inserted to fit within a central aperture provided in the distal cap such that one or more inwardly-projecting stop portions (e.g., flanges or raised edges) provided in the central aperture of the distal cap reliably engage the gap 1012a, 1012b of the needle shield remover 1000. This engagement allows the needle shield remover 1000 to be reliably engaged to the distal cap after assembly and during removal of the distal cap from the device housing, thus causing removal of the distal cap from the device housing to automatically remove the needle shield remover 1000 as well. Since the needle shield remover 1000 is reliably engaged to one or more needle shields, removal of the needle shield remover, in turn, automatically removes the needle shields coupled to the syringe.

In the exemplary embodiment illustrated in FIGS. 10A and 10B, the needle shield remover 1000 may be provided as a separate component from a distal cap of the automatic injection device. In another exemplary embodiment, a needle shield remover may be provided integrally with the distal cap, for example, by integrally coupling the cap engagement mechanisms 1010a, 1010b of the needle shield remover 1000 with the distal cap of the device.

The proximal tubular member 1002 of the needle shield remover 1000 may be substantially cylindrical in shape with a substantially circular or oval cross-section. The side wall of the proximal tubular member 1002 may enclose and define a substantially cylindrical cavity 1014 for housing the injection needle covered by a soft needle shield and/or a rigid needle shield coupled to the syringe.

At or near its proximal edge, the side wall of the proximal tubular member 1002 may define and/or include a first inwardly-projecting shield engagement mechanism 1016a and a second inwardly-projecting shield engagement mechanism 1016b. The first and second inwardly-projecting shield engagement mechanisms 1016a, 1016b may be biased by the side wall to reliably remain positioned within a gap formed between the body of a syringe and the proximal edge of a rigid needle shield. Exemplary inwardly-projecting shield engagement mechanisms 1016a, 1016b may be any suitable protrusion, projection, teeth, and the like. In the exemplary embodiment of FIGS. 10A and 10B, the exemplary inwardly-projecting shield engagement mechanisms 1016a, 1016b are provided at opposite sides of the needle shield remover 1000, i.e., separated from each other by about 180 degrees. The inwardly-projecting shield engagement mechanisms 1016a, 1016b may be positioned in a gap formed between a syringe body and a rigid needle shield during the assembly process, and may reliably be positioned in the gap during the use of the device. When the distal cap covering the injection needle is removed before performing an injection (by pulling in the direction indicated by arrow R), the inwardly-projecting shield engagement mechanisms 1016a, 1016b exert force in the direction R against the peripheral edge of the rigid needle shield, thereby pulling the rigid needle shield and the soft needle shield away from the syringe body in the direction R and exposing the injection needle for performing an injection.

In an exemplary configuration, each inwardly-projecting shield engagement mechanisms 1016a, 1016b may be situated at an aperture 1018a, 1018b that provides an opening in the side wall of the proximal tubular member 1002. Each inwardly-projecting shield engagement mechanisms 1016a, 1016b may include an inwardly-projecting inclined or radial wall 1020a, 1020b that extends from a proximal base wall of the aperture 1018a, 1018b and projects inwardly into the cavity 1014 at an angle relative to the longitudinal axis L. An exemplary angle may range from about 30 degrees to about 60 degrees relative to the longitudinal axis L toward the cavity. Providing the shield engagement mechanisms 1016a, 1016b as part of the proximal tubular member 1002 facilitates robust assembly of the needle shield remover 1000 in the automatic injection device. Projection of the inclined or radial walls of the shield engagement mechanisms 1016a, 1016b from the proximal base wall of the aperture 1018a, 1018b inwardly into the cavity 1014 also facilitates robust assembly of the needle shield remover 1000 in the device. These structural features, for example, allow the inclined or radial walls of the needle shield remover 1000 to move radially outwardly with respect to the proximal tubular member 1002, while minimizing a radially outward movement of the proximal tubular member 1002 at the shield engagement mechanisms 1016a, 1016b, as the needle shield remover 1000 is inserted coaxially over a needle shield during assembly. That is, expansion of the outer diameter of the needle shield remover 1000 is minimized during assembly in order to minimize the risk of the shield engagement mechanisms 1016a, 1016b not being positioned at the gap between the needle shield and the syringe body and to minimize the risk of the shield engagement mechanisms 1016a, 1016b from becoming disengaged from the gap between the needle shield and the syringe body.

Certain conventional needle shield removers include shield engagement mechanisms that are not formed as a part of a tubular member. In addition, in certain conventional needle shield removers, the shield engagement mechanisms do not extend from a proximal base edge of an aperture or support mechanism. These conventional needle shield removers do not minimize a radially outward movement needle shield removers at the shield engagement mechanisms. This radially outward movement of the conventional needle shield removers reduces the robustness of the assembly process as it increases the risk of positioning the shield engagement mechanisms outside a gap formed between the syringe body and the needle shield.

In an exemplary embodiment, the proximal tubular member 1002 may be dissected by one or more slots 1001a, 1001b that extend substantially parallel to the longitudinal axis L at radial locations between the shield engagement mechanisms 1016a, 1016b. In an exemplary embodiment, two exemplary slots 1001a, 1001b may be separated from each other on the proximal tubular member 1002 by about 180 degrees. In an exemplary embodiment, the slots 1001a, 1001b may facilitate in engaging the shield engagement mechanisms 1016a, 1016b of the needle shield remover 1000 with a rigid needle shield.

In this exemplary embodiment, the slots 1001a, 1001b may allow the shield engagement mechanisms 1016a, 1016b to move radially outwardly as the needle shield remover 1000 is inserted coaxially over a needle shield during assembly, which advantageously allows the needle shield remover 1000 to be engaged to the needle shield without requiring the application of a large amount of force opposite to the direction indicated by arrow R. Application to a large amount force during assembly can result in damage to the needle shields and the syringe, thereby adversely affecting the reliability of the assembled needle shield remover.

Exemplary inclined or radial walls may have any suitable dimension and structure. Exemplary lengths and widths of the inclined or radial walls may include, but are not limited to, about 1, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.5, 7 mm, all intermediate numbers, and the like.

The inclined or radial walls 1020a, 1020b of the inwardly-projecting shield engagement mechanisms 1016a, 1016b may be configured to be positioned within a gap formed between a syringe body and a proximal edge of a rigid needle shield. The inclined or radial wall 1020a, 1020b may have a peripheral edge 1024a, 1024b with a width that provides a sufficiently large interface with the rigid needle shield. In exemplary embodiments, the width of the peripheral edge 1024a, 1024b may range from about 3 mm to about 7 mm, but is not limited to this exemplary range. In an exemplary embodiment, the width is about 5.3 mm.

In an exemplary embodiment, the inwardly-projecting inclined or radial walls 1020a, 1020b cause the inner diameter of the needle shield remover 1000 at the inwardly-projecting shield engagement mechanisms 1016a, 1016b to be less than the outer diameter of the proximal end of the rigid needle shield. In an exemplary embodiment, the inwardly-projecting inclined or radial walls 1020a, 1020b cause the inner diameter of the needle shield remover 1000 at the inwardly-projecting shield engagement mechanisms 1016a, 1016b to be less than the outer diameter of the syringe body. The inner diameter of the needle shield remover 1000 at the inwardly-projecting shield engagement mechanisms 1016a, 1016b may be substantially equal to the outer diameter of the gap formed between the syringe body and the proximal end of the rigid needle shield. This configuration of the inwardly-projecting shield engagement mechanisms 1016a, 1016b thereby allows the inclined or radial walls 1020a, 1020b to snap into place at the gap in a reliable and tight manner so that disengagement requires at least a minimal threshold level of force. This configuration also prevents creep of the inclined or radial walls 1020a, 1020b out of the gap after assembly but before removal by a user.

The inwardly-projecting shield engagement mechanisms 1016a, 1016b may snap into place at the gap formed between the rigid needle shield and the syringe body, as the needle shield remover 1000 is inserted over the rigid needle shield. When the inwardly-projecting shield engagement mechanisms 1016a, 1016b snap into place at the gap, there may be a decrease in the force experienced against insertion of the needle shield remover 1000 over the rigid needle shield. In an exemplary embodiment, this decrease in the force may be sensed by a user or automatically by an assembly machine to determine that the inwardly-projecting shield engagement mechanisms 1016a, 1016b have been successfully engaged to the gap formed between the rigid needle shield and the syringe body. In an exemplary embodiment, the positioning of the inwardly-projecting shield engagement mechanisms 1016a, 1016b in the gap may emit an audible "click" sound that provides an audible indication that the needle shield remover 1000 has been successfully engaged with the rigid needle shield.

In the exemplary embodiment illustrated in FIGS. 10A and 10B, the needle shield remover 1000 may be provided as a separate component from a needle shield of the automatic injection device. In another exemplary embodiment, a needle shield remover may be provided integrally with the rigid needle shield, for example, by integrally coupling the inwardly-projecting shield engagement mechanisms 1016a, 1016b of the needle shield remover 1000 with the rigid needle shield.

At or near its proximal edge, the side wall of the proximal tubular member 1002 may also define one or more cutout portions 1026a, 1026b for allowing a user to view of the contents of the syringe and/or to view an indicator from outside the device housing. That is, the cutout portions 1026a, 1026b of the proximal tubular member 1002 align with a transparent inspection window or inspection aperture of the device housing to allow a user to view the syringe contents and/or to view an indicator from outside the device. In the exemplary embodiment of FIGS. 10A and 10B, a first cutout portion 1026a and a second cutout portion 1026b are provided at opposite sides of the needle shield remover 1000, i.e., separated from each other by about 180 degrees. In an exemplary embodiment, the cutout portions 1026a, 1026b may be provided in an alternating manner with the inwardly-projecting shield engagement mechanisms 1016a, 1016b, all of which are provided at or near the proximal edge of the proximal tubular member 1002. In an exemplary embodiment, each cutout portion 1026a, 1026b may take a substantially concave shape or a semicircular shape, but is not limited to these exemplary shapes. In an exemplary embodiment, the distal ends of the cutout portions 1026a, 1026b may contiguously join with the dissection slots 1001a, 1001b.

In an exemplary embodiment, one or more additional protrusions and/or grooves may be provided in the exterior surface of the proximal tubular member 1002 and/or the distal tubular member 1004 in order to facilitate engagement of the needle shield remover 1000 with another component of the automatic injection device, e.g., a syringe sleeve that cooperatively engages with and covers a proximal portion of the needle shield remover, a removable cap that covers a distal portion of the needle shield remover, and the like. For example, one or more longitudinally-extending grooves 1028a, 1028b may be provided in the exterior surface of the needle shield remover 1000 to movably engage with a syringe sleeve. In an exemplary embodiment, the syringe sleeve may allow relative movement of the syringe sleeve and/or the needle shield remover along the longitudinal axis L, but may hold the needle shield remover in a substantially fixed axial orientation relative to the syringe sleeve. This ensures that the cutout portions 1026a, 1026b of the needle shield remover 1000 are maintained in alignment with a transparent inspection window or inspection aperture of the syringe sleeve and with a transparent inspection window or inspection aperture of the device housing, thus allowing a user to view the contents of the syringe and/or to view an indicator through the inspection windows or inspection apertures.

Figure 12:
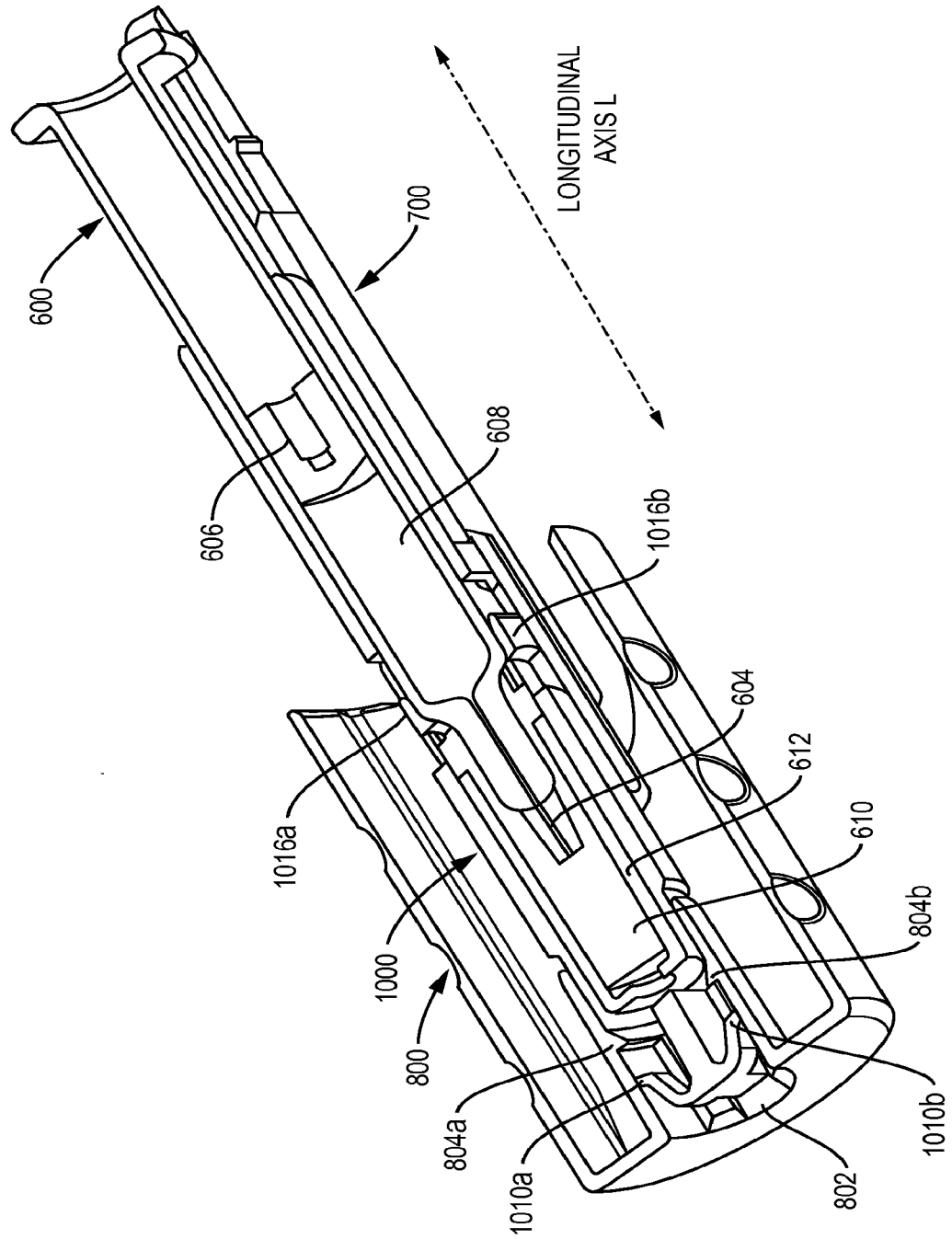
FIG. 12 illustrates a cross-sectional perspective view of the exemplary needle shield remover of FIGS. 10A and 10B assembled with a syringe, a distal cap and a syringe sleeve.
Figure 13:
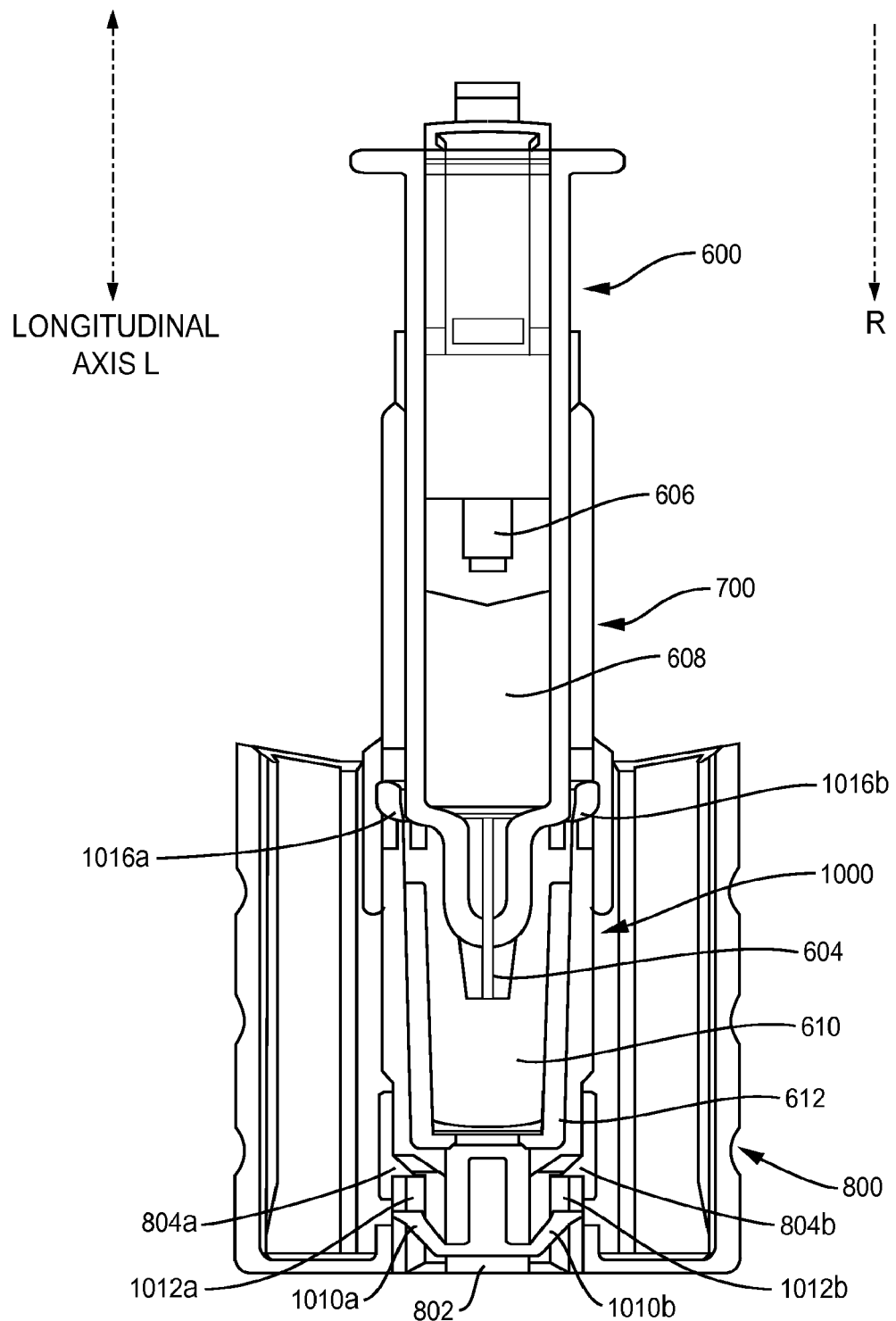
FIG. 13 illustrates a front cross-sectional view of the exemplary assembly of FIG. 12.
Figure 14:
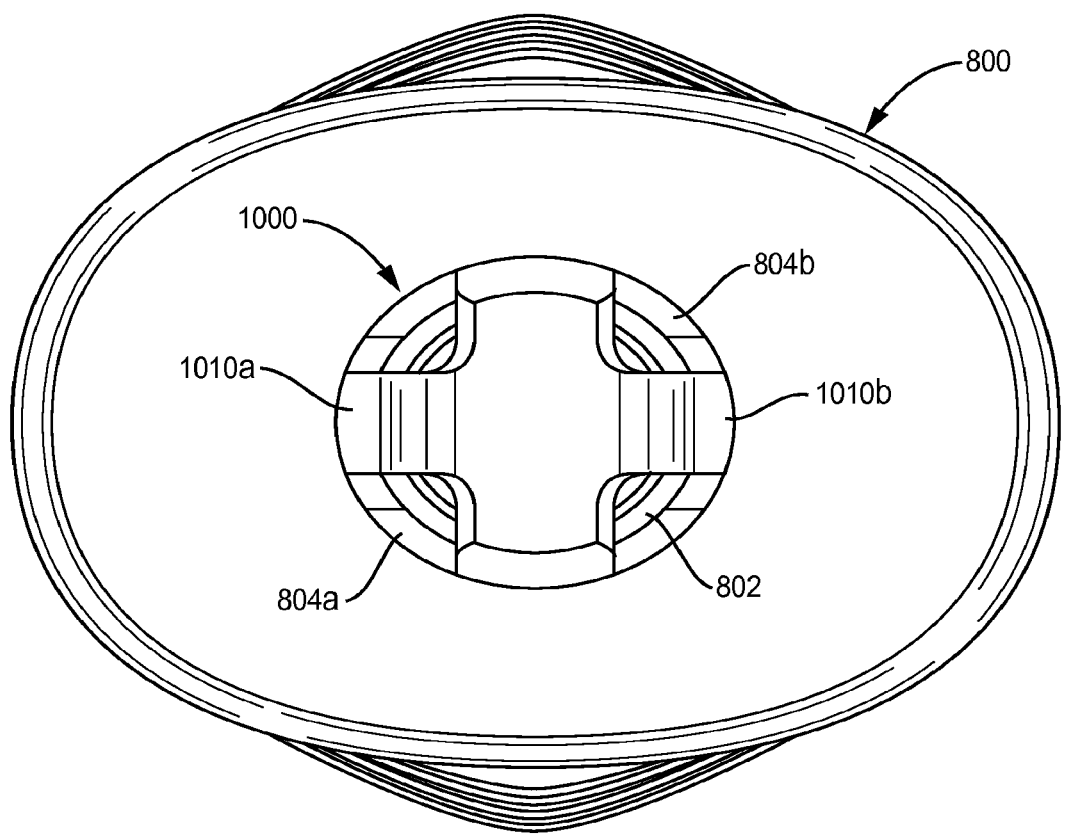
FIG. 14 illustrates a bottom view of an exemplary distal cap that is applicable to FIGS. 11-13.
Figure 15:
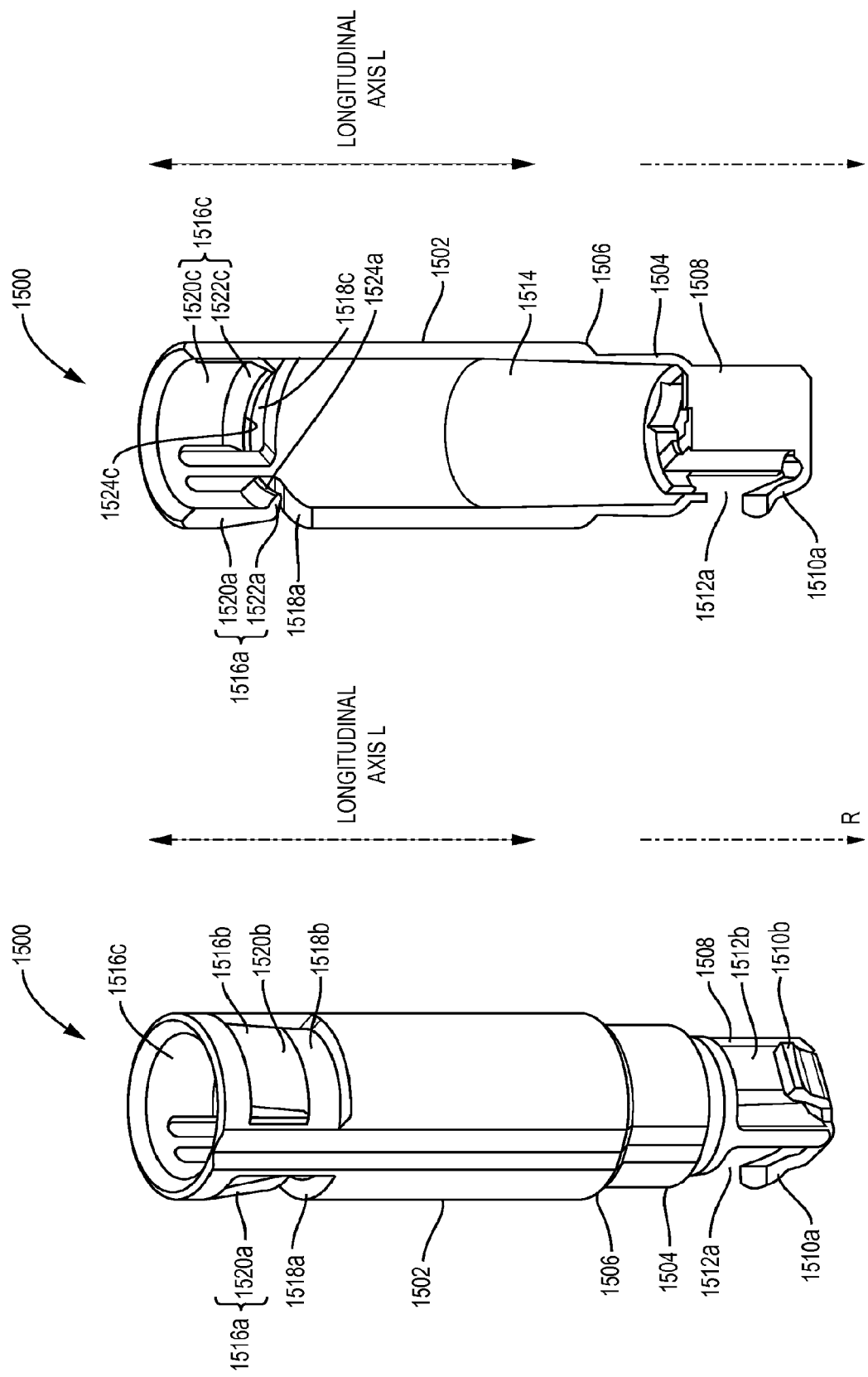
FIG. 15A illustrates a perspective view of an exemplary needle shield remover.
FIG. 15B illustrates a cross-sectional perspective view of the exemplary needle shield remover of FIG. 15A bisected along a longitudinal axis L.

FIG. 11 illustrates a perspective cross-sectional view of the exemplary needle shield remover 1000 of FIGS. 10A and 10B assembled with a syringe 600 and a distal cap 800. In the exemplary embodiment of FIG. 11, the assembly lacks a syringe sleeve. FIG. 12 illustrates a perspective cross-sectional view of the exemplary needle shield remover 1000 of FIGS. 10A and 10B assembled with a syringe 600 and a distal cap 800. In the exemplary embodiment of FIG. 12, the assembly includes a syringe sleeve 700. FIG. 13 illustrates a front cross-sectional view of the exemplary assembly of FIG. 12 including a syringe sleeve 700. FIG. 14 illustrates a bottom view of an exemplary distal cap 800 that is applicable to FIGS. 11-13.

An injection needle 604 may be affixed to a distal end of the syringe 600, a bung 606 may be disposed within the syringe 600, and a dose of a therapeutic agent 608 may be provided to fill the syringe 600. The injection needle 604 may be covered with a soft needle shield 610 and a rigid needle shield 612 disposed over the soft needle shield 610. The exemplary needle shield remover 1000 may be disposed over the rigid needle shield 612 so that the inwardly-projecting shield engagement mechanisms 1016a, 1016b of the needle shield remover 1000 fit within a gap between the rigid needle shield 612 and the body of the syringe 600. The cap engagement mechanisms 1010a, 1010b of the needle shield remover 1000 may engage with a distal cap 800 provided to cover the distal portion of the device. In an exemplary embodiment, the cap engagement mechanisms 1010a, 1010b may be accommodated within a central aperture 802 provided in the distal cap 800, so that inwardly-projecting stop portions 804a, 804b (e.g., flanges or raised edges) provided in the central aperture of the distal cap are positioned reliably within gaps 1012a, 1012b proximal to the cap engagement mechanisms 1010a, 1010b.

In the exemplary embodiment illustrated in FIGS. 12 and 13, a syringe sleeve 700 may be provided over the syringe 600 and the needle shield remover 1000 to maintain the needle shield remover 1000 in a substantially fixed axial orientation with the device housing.

Exemplary components illustrated in FIGS. 11-14 that are common to the components illustrated in FIGS. 2-3 are described in connection with FIGS. 2-3.

VI. Third Non-Limiting Exemplary Embodiment of a Needle Shield Remover

FIGS. 15A and 15B illustrate an exemplary needle shield remover 1500 having three exemplary inwardly-projecting shield engagement mechanisms for engagement with a rigid needle shield. FIG. 15A illustrates a perspective view of the exemplary needle shield remover 1500. FIG. 15B illustrates a cross-sectional perspective view of the exemplary needle shield remover 1500 bisected along a longitudinal axis L.

The exemplary needle shield remover 1500 may include a proximal tubular member 1502 that, at its distal edge, is integrally coupled to a distal tubular member 1504 in some exemplary embodiments. The distal tubular member 1504 may have a smaller diameter and a shorter length than the proximal tubular member 1502, and may extend along a shorter length of the needle shield remover 1500 along the longitudinal axis L than the proximal tubular member 1502. A transition portion 1506 may extend between the proximal tubular member 1502 and the distal tubular member 1504. An exemplary transition portion 1506 may be a stepped transition, a ramped transition, or a combination of both.

The distal tubular member 1504 of the needle shield remover 1500 may be substantially cylindrical in shape with a substantially circular or oval cross-section. At its distal end, the side wall of the distal tubular member 1504 may include one or more platform structures 1508 that project longitudinally from the face of the distal tubular member 1504 toward a removable distal cap. In an exemplary embodiment, a platform structure 1508 may include one or more longitudinally-projecting portions and a transverse portion that extends between the longitudinally-projecting portions at the distal end of the platform structure 1508.

At its distal end, one or more platform structures 1508 may support or define or provide a first outwardly-projecting flexible cap engagement mechanism 1510a, a second outwardly-projecting flexible cap engagement mechanism 1510b and a third outwardly-projecting flexible cap engagement mechanism 1510c, that project radially outwardly from the platform structure 1508. Providing three cap engagement mechanisms in this exemplary embodiment provides a larger surface of the needle shield remover that engages with the distal cap than embodiments that include one or two cap engagement mechanism. The exemplary needle shield remover 1500 thereby allows reliably removal of the needle shield remover from the syringe when the distal cap is removed before administration of an injection.

Exemplary cap engagement mechanisms may be any suitable protrusion, projection, teeth, and the like. In the exemplary embodiment of FIGS. 15A and 15B, the cap engagement mechanisms 1510*a*, 1510*b*, 1510*c* are spaced from one another around the platform structure 1508, i.e., separated by about 120 degrees. One of ordinary skill in the art will recognize that exemplary needle shield removers may include any suitable number of cap engagement mechanisms extending from the platform structure 1508 including, but not limited to, one, two, three, four, five, six, seven, and the like.

A first end of each cap engagement mechanisms 1510*a*, 1510*b*, 1510*c* may be coupled to or may be provided integrally with the platform structure 1508, and a second end of each cap engagement mechanism 1510*a*, 1510*b*, 1510*c* may be suspended over a gap (e.g., gap 1512*a*, 1512*b*, 1512*c*) between the cap engagement mechanisms 1510*a*, 1510*b*, 1510*c* and the distal tubular member 1504. During assembly of the needle shield remover 1500 with a distal cap of the automatic injection device (not pictured) provided to cover the needle shield remover, the cap engagement mechanisms 1510*a*, 1510*b*, 1510*c* may be coupled to the distal cap so that removal of the cap also automatically removes the needle shield remover 1500.

In an exemplary embodiment, the cap engagement mechanisms 1510*a*, 1510*b*, 1510*c* of the needle shield remover 1500 may be inserted to fit within a central aperture provided in the distal cap such that one or more inwardly-projecting stop portions (e.g., flanges or raised edges) provided in the central aperture of the distal cap reliably engage the gaps 1512*a*, 1512*b*, 1512*c* of the needle shield remover 1500. This engagement allows the needle shield remover 1500 to be reliably engaged to the distal cap after assembly and during removal of the distal cap from the device housing, thus causing removal of the distal cap from the device housing to automatically remove the needle shield remover 1500 as well. Since the needle shield remover 1500 is reliably engaged to one or more needle shields, removal of the needle shield remover, in turn, automatically removes the needle shields.

In the exemplary embodiment illustrated in FIGS. 15A and 15B, the needle shield remover 1500 may be provided as a separate component from a distal cap of the automatic injection device. In another exemplary embodiment, a needle shield remover may be provided integrally with the distal cap, for example, by integrally coupling the cap engagement mechanisms 1510*a*, 1510*b*, 1510*c* of the needle shield remover 1500 with the distal cap of the device.

The proximal tubular member 1502 of the needle shield remover 1500 may be substantially cylindrical in shape with a substantially circular or oval cross-section. The side wall of the proximal tubular member 1502 may enclose and define a substantially cylindrical cavity 1514 for housing the injection needle covered by a soft needle shield and/or a rigid needle shield.

At or near its proximal edge, the side wall of the proximal tubular member 1502 may define and/or include a first inwardly-projecting shield engagement mechanism 1516*a*, a second inwardly-projecting shield engagement mechanism 1516*b*, and a third inwardly-projecting shield engagement mechanism 1516*c*. The first, second and third inwardly-projecting shield engagement mechanisms 1516*a*, 1516*b*, 1516*c* may be biased by the side wall to reliably remain positioned within a gap formed between the body of a syringe and the proximal edge of a rigid needle shield. Exemplary inwardly-projecting shield engagement mechanisms 1516*a*, 1516*b*, 1516*c* may be any suitable protrusion, projection, teeth, and the like. In the exemplary embodiment of FIGS. 15A and 15B, the exemplary inwardly-projecting shield engagement mechanisms 1516*a*, 1516*b*, 1516*c* may be spaced from one another around the needle shield remover 1500, i.e., separated from each other by about 120 degrees.

The inwardly-projecting shield engagement mechanisms 1516*a*, 1516*b*, 1516*c* may be positioned in a gap formed between a syringe body and a rigid needle shield during the assembly process, and may reliably be positioned in the gap during the use of the device. When the distal cap covering the injection needle is removed before performing an injection (by pulling in the direction indicated by arrow R), the inwardly-projecting shield engagement mechanisms 1516*a*, 1516*b*, 1516*c* exert force in the direction R against the peripheral edge of the rigid needle shield, thereby pulling the rigid needle shield and the soft needle shield away from the syringe body in the direction R and exposing the injection needle for performing an injection.

In an exemplary configuration, each inwardly-projecting shield engagement mechanism 1516*a*, 1516*b*, 1516*c* may be situated at an aperture 1518*a*, 1518*b*, 1518*c* that provides an opening in the side wall of the proximal tubular member 1502. Each inwardly-projecting shield engagement mechanisms 1516*a*, 1516*b*, 1516*c* may include a first inclined or radial wall 1520*a*, 1520*b*, 1520*c* that extends from a proximal wall of the aperture 1518*a*, 1518*b*, 1518*c* into the cavity 1514 at a first angle relative to the longitudinal axis L. The first inclined or radial wall 1520*a*, 1520*b*, 1520*c* may be coupled to or may be integrally formed with an inwardly-projecting second inclined or radial wall 1522*a*, 1522*b*, 1522*c*. The second inclined or radial wall 1522*a*, 1522*b*, 1522*c* may extend from the first inclined or radial wall into the cavity 1514 at a second angle relative to the longitudinal axis L.

The second angle corresponding to the second inclined or radial wall 1522*a*, 1522*b*, 1522*c* may be substantially greater than the first angle corresponding to the first inclined or radial wall 1520*a*, 1520*b*, 1520*c*, so that the first inclined or radial wall 1520*a*, 1520*b*, 1520*c* extends substantially along the longitudinal axis L and the second inclined or radial wall 1522*a*, 1522*b*, 1522*c* extends substantially orthogonally to the longitudinal axis L. An exemplary first angle may range from about 0 degree to about 20 degrees relative to the longitudinal axis L toward the cavity 1514. An exemplary second angle may range from about 30 degrees to about 60 degrees relative to the longitudinal axis L toward the cavity 1514.

Providing the shield engagement mechanisms 1516*a*, 1516*b*, 1516*c* as part of the proximal tubular member 1502 facilitates robust assembly of the needle shield remover 1500 in the automatic injection device. Projection of the inclined or radial walls of the shield engagement mechanisms 1516*a*, 1516*b*, 1516*c* from the proximal base wall of the aperture 1518*a*, 1518*b*, 1518*c* inwardly into the cavity 1514 also facilitates robust assembly of the needle shield remover 1500 in the device. These structural features, for example, allow the inclined or radial walls of the needle shield remover 1500 to move radially outwardly with respect to the proximal tubular member 1502, while minimizing a radially outward movement of the proximal tubular member 1502 at the shield engagement mechanisms 1516*a*, 516*b*, 1516*c*, as the needle shield remover 1500 is inserted coaxially over a needle shield during assembly. That is, expansion of the outer diameter of the needle shield remover 1500 is minimized during assembly in order to minimize the risk of the shield engagement mechanisms 1516*a*, 1516*b*, 1516*c* not being positioned at the gap between the needle shield and the syringe body and to minimize the risk of the shield engagement mechanisms 1516*a*, 1516*b*, 1516*c* from becoming disengaged from the gap between the needle shield and the syringe body.

Certain conventional needle shield removers include shield engagement mechanisms that are not formed as a part of a tubular member. In addition, in certain conventional needle shield removers, the shield engagement mechanisms do not extend from a proximal base edge of an aperture or support mechanism. These conventional needle shield removers do not minimize a radially outward movement needle shield removers at the shield engagement mechanisms. This radially outward movement of the conventional needle shield removers reduces the robustness of the assembly process as it increases the risk of positioning the shield engagement mechanisms outside a gap formed between the syringe body and the needle shield.

Exemplary first and second inclined or radial walls may have any suitable dimension and structure. Exemplary lengths and widths of the first and second inclined or radial walls may include, but are not limited to, about 1, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.5, 7 mm, all intermediate numbers, and the like.

The second inclined or radial wall 1522*a*, 1522*b*, 1522*c* of the inwardly-projecting shield engagement mechanisms 1516*a*, 1516*b*, 1516*c* may be configured to be positioned within a gap formed between a syringe body and a proximal edge of a rigid needle shield. Providing three inwardly-projecting shield engagement mechanisms 1516*a*, 1516*b*, 1516*c* in this exemplary embodiment provides a larger surface of the needle shield remover that engages with the rigid needle shield than embodiments that include one or two inwardly-projecting shield engagement mechanism. The exemplary needle shield remover 1500 thereby allows reliably removal of the needle shields from the syringe when the needle shield remover is removed before administration of an injection. The second inclined or radial wall 1522*a*, 1522*b*, 1522*c* may have a peripheral edge 1524*a*, 1524*b*, 1524*c* with a width that provides a sufficiently large interface with the rigid needle shield. In exemplary embodiments, the width of the peripheral edge 1524*a*, 1524*b*, 1524*c* may range from about 3 mm to about 7 mm, but is not limited to this exemplary range. In an exemplary embodiment, the width is about 5.4 mm. The greater width of the peripheral edge of the second inclined or radial wall 1522*a*, 1522*b*, 1522*c* also provides a larger surface of the needle shield remover that engages with the rigid needle shield than embodiments that include one or two inwardly-projecting shield engagement mechanism, allowing reliable removal of the needle shields from the syringe when the needle shield remover is removed before administration of an injection In an exemplary embodiment, the inwardly-projecting first and second inclined or radial walls cause the inner diameter of the needle shield remover 1500 at the inwardly-projecting shield engagement mechanisms 1516*a*, 1516*b*, 1516*c* to be less than the outer diameter of the proximal end of the rigid needle shield. In an exemplary embodiment, the inwardly-projecting first and second inclined or radial walls cause the inner diameter of the needle shield remover 1500 at the inwardly-projecting shield engagement mechanisms 1516*a*, 1516*b*, 1516*c* to be less than the outer diameter of the syringe body. The inner diameter of the needle shield remover 1500 at the inwardly-projecting shield engagement mechanisms 1516*a*, 1516*b*, 1516*c* may be substantially equal to the outer diameter of the gap formed between the syringe body and the proximal end of the rigid needle shield. This configuration of the inwardly-projecting shield engagement mechanisms 1516*a*, 1516*b*, 1516*c* thereby allows the second inclined or radial walls 1522*a*, 1522*b*, 1522*c* to snap into place at the gap in a reliable and tight manner so that disengagement requires at least a minimal threshold level of force. This configuration also prevents creep of the second inclined or radial walls 1522*a*, 1522*b*, 1522*c* out of the gap after assembly but before removal by a user.

The inwardly-projecting shield engagement mechanisms 1516*a*, 1516*b*, 1516*c* may snap into place at the gap formed between the rigid needle shield and the syringe body, as the needle shield remover 1500 is inserted over the rigid needle shield. When the inwardly-projecting shield engagement mechanisms 1516*a*, 1516*b*, 1516*c* snap into place at the gap, there may be a decrease in the force experienced against insertion of the needle shield remover 1500 over the rigid needle shield. In an exemplary embodiment, this decrease in the force may be sensed by a user or automatically by an assembly machine to determine that the inwardly-projecting shield engagement mechanisms 1516*a*, 1516*b*, 1516*c* have been successfully engaged to the gap formed between the rigid needle shield and the syringe body. In an exemplary embodiment, the positioning of the inwardly-projecting shield engagement mechanisms 1516*a*, 1516*b*, 1516*c* in the gap may emit an audible "click" sound that provides an audible indication that the needle shield remover 1500 has been successfully engaged with the rigid needle shield.

In the exemplary embodiment illustrated in FIGS. 15A and 15B, the needle shield remover 1500 may be provided as a separate component from a distal cap of the automatic injection device. In another exemplary embodiment, a needle shield remover may be provided integrally with the distal cap, for example, by integrally coupling the inwardly-projecting shield engagement mechanisms 1516*a*, 1516*b*, 1516*c* of the needle shield remover 1500 with the distal cap of the device.

In an exemplary embodiment, one or more additional protrusions and/or grooves may be provided in the exterior surface of the proximal tubular member 1502 and/or the distal tubular member 1504 in order to facilitate engagement of the needle shield remover 1500 with another component of the automatic injection device, e.g., a syringe sleeve that cooperative engages with and covers a proximal portion of the needle shield remover, a removable cap that covers a distal portion of the needle shield remover, and the like.

Figure 16:
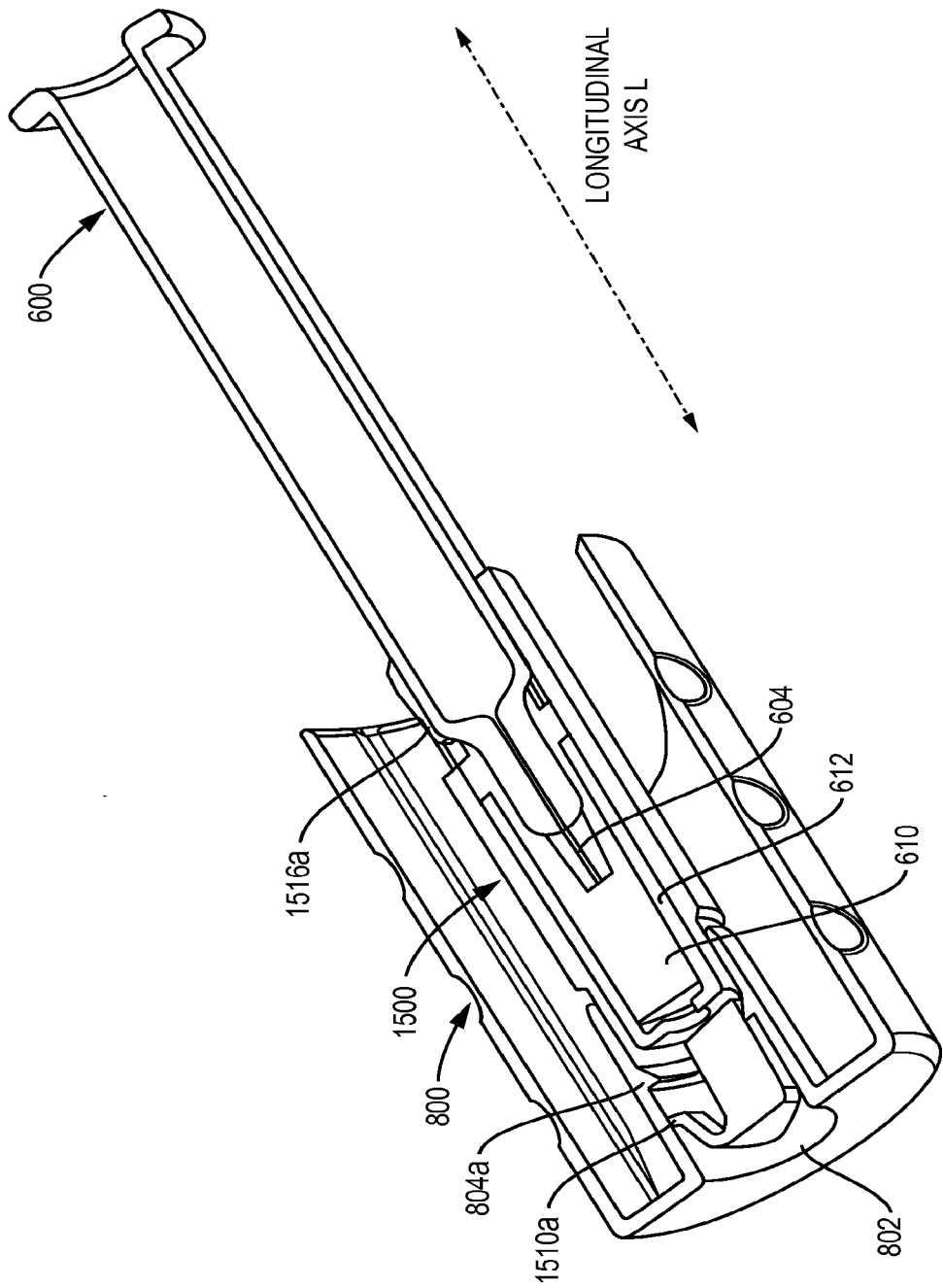
FIG. 16 illustrates a cross-sectional perspective view of the exemplary needle shield remover of FIGS. 15A and 15B assembled with a syringe and a distal cap.
Figure 17:
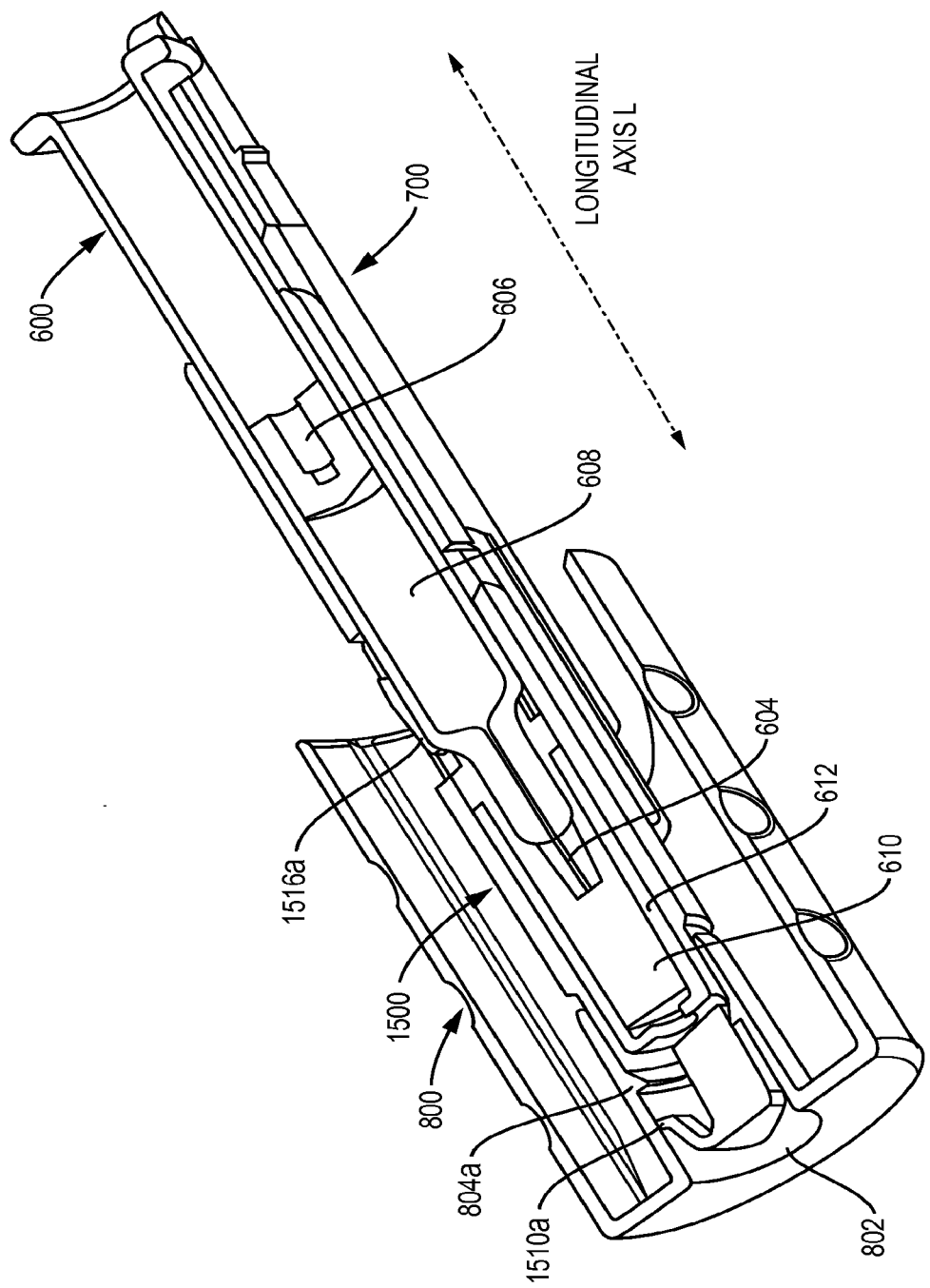
FIG. 17 illustrates a cross-sectional perspective view of the exemplary needle shield remover of FIGS. 15A and 15B assembled with a syringe, a distal cap and a syringe sleeve.
Figure 18:
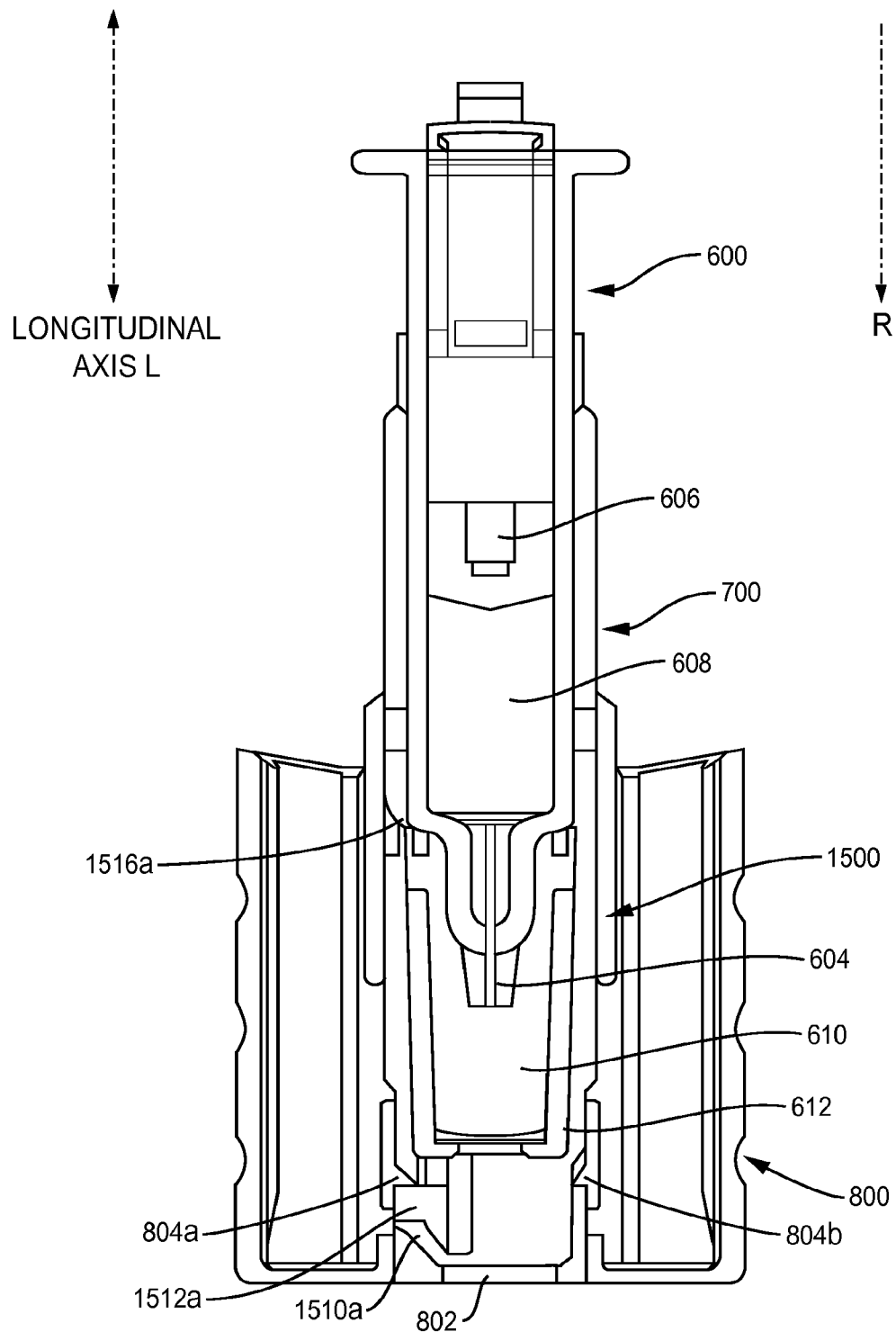
FIG. 18 illustrates a front cross-sectional view of the exemplary assembly of FIG. 17.
Figure 19:
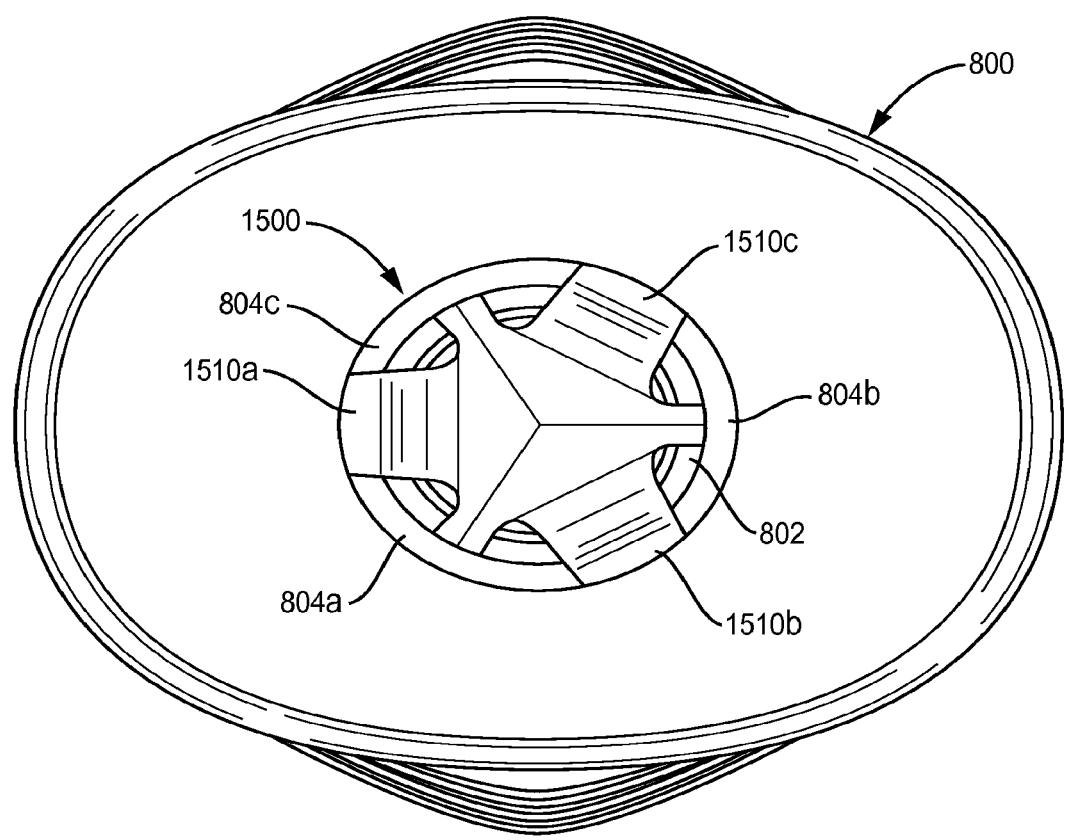
FIG. 19 illustrates a bottom view of an exemplary distal cap that is applicable to FIGS. 16-18.

FIG. 16 illustrates a perspective cross-sectional view of the exemplary needle shield remover 1500 of FIGS. 15A and 15B assembled with a syringe 600 and a distal cap 800. In the exemplary embodiment of FIG. 16, the assembly lacks a syringe sleeve. FIG. 17 illustrates a perspective cross-sectional view of the exemplary needle shield remover 1500 of FIGS. 15A and 15B assembled with a syringe 600 and a distal cap 800. In the exemplary embodiment of FIG. 17, the assembly includes a syringe sleeve 700. FIG. 18 illustrates a front cross-sectional view of the exemplary assembly of FIG. 17 including a syringe sleeve 700. FIG. 19 illustrates a bottom view of an exemplary distal cap 800 that is applicable to FIGS. 16-18.

An injection needle 604 may be affixed to a distal end of the syringe 600, a bung 606 may be disposed within the syringe 600, and a dose of a therapeutic agent 608 may be provided to fill the syringe 600. The injection needle 604 may be covered with a soft needle shield 610 and a rigid needle shield 612 disposed over the soft needle shield 610. The exemplary needle shield remover 1500 may be disposed over the rigid needle shield 612 so that the inwardly-projecting shield engagement mechanisms 1516a, 1516b, 1516c of the needle shield remover 1500 fit within a gap between the rigid needle shield 612 and the body of the syringe 600. The cap engagement mechanisms 1510a, 1510b, 1510c of the needle shield remover 1500 may engage with a distal cap 800 provided to cover the distal portion of the device. In an exemplary embodiment, the cap engagement mechanisms 1510a, 1510b, 1510c may be accommodated within a central aperture 802 provided in the distal cap 800, so that inwardly-projecting stop portions 804a, 804b, 804c (e.g., flanges or raised edges) provided in the central aperture of the distal cap are positioned reliably within gaps 1512a, 1512b, 1512c proximal to the cap engagement mechanisms 1510a, 1510b, 1510c.

In an exemplary embodiment illustrated in FIGS. 17 and 18, a syringe sleeve 700 may be provided over the syringe 600 and the needle shield remover 1500 to maintain the needle shield remover 1500 in a substantially fixed axial orientation with the device housing.

Exemplary components illustrated in FIGS. 16-19 that are common to the components illustrated in FIGS. 2-3 are described in connection with FIGS. 2-3.

Figure 20:
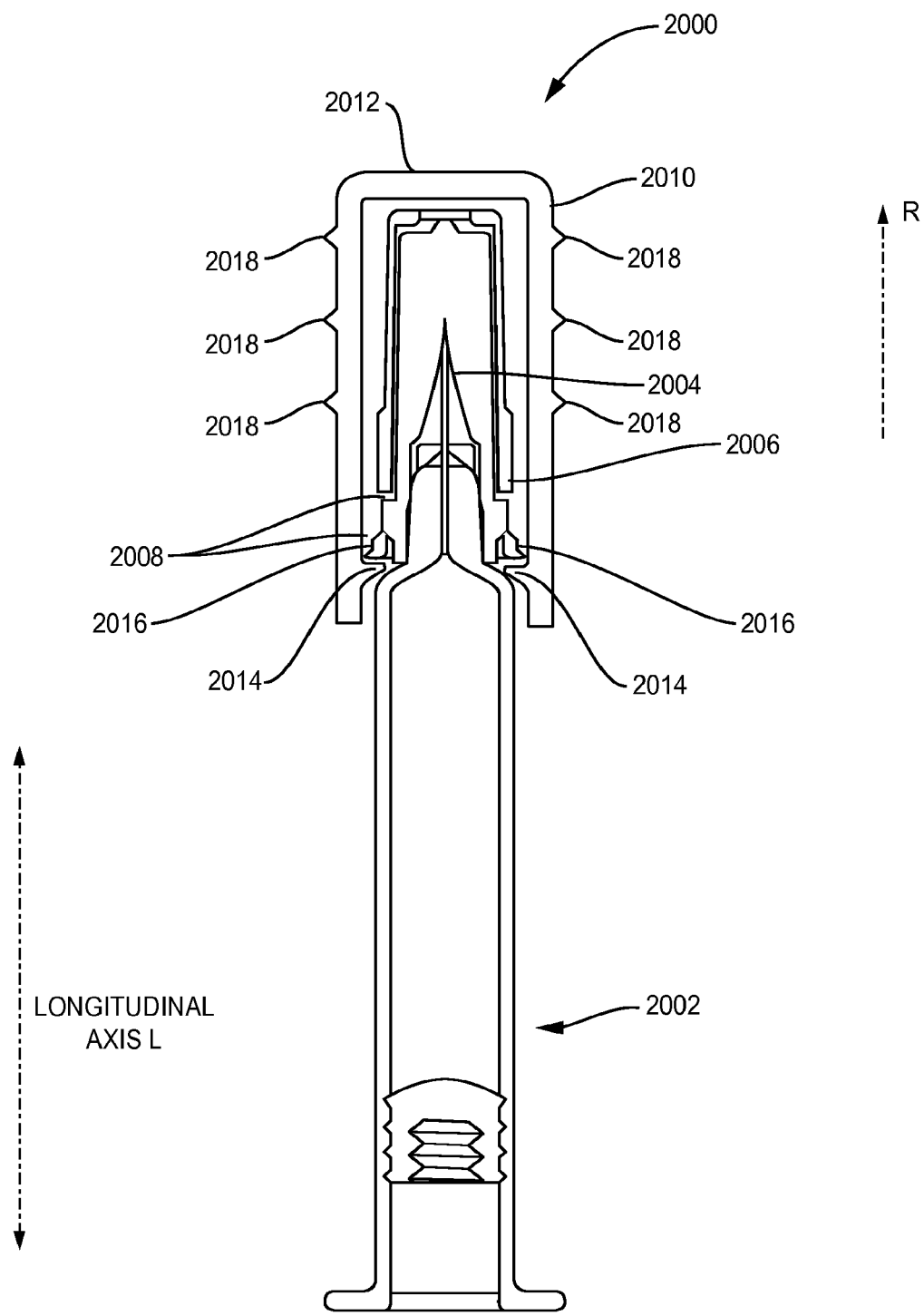
FIG. 20 illustrates a cross-sectional view of another exemplary needle shield remover bisected along the longitudinal axis L.

VII. Certain Other Non-Limiting Exemplary Embodiments of Needle Shield Removers FIG. 20 illustrates a cross-sectional view of an exemplary needle shield remover 2000 bisected along the longitudinal axis L. The needle shield remover 2000 is configured for removing needle shields from a syringe 2002 or an automatic injection device. The syringe 2002 may include any type of syringe typically utilized with an automatic injection device having one or more needle shields, such as a soft needle shield 2004 and a rigid needle shield 2006. As discussed above, the soft needle shield 2004 is positioned within the rigid needle shield 2006, and portions of the soft needle shield 2004 extend through apertures 2008 formed in the rigid needle shield 2006.

The needle shield remover 2000 includes a outer wall 2010 which is attached to and depends from (or is formed integrally with) the periphery of an base wall 2012, and one or more inwardly-facing protrusions or teeth 2014 which are biased by the outer wall 2010 in position within a gap formed between the body of the syringe 2002 and the periphery 2016 of the rigid needle shield 2006. The outer wall 2010 and base wall 2012 may have any desired shape or size (e.g., the needle shield remover 2000 may be cylindrical or other shape), and a plurality of outer walls 2010 may be provided (e.g., if the needle shield remover 2000 is square or rectangular in shape). The needle shield remover 2000 defines a cavity that receives the soft needle shield 2004 and the rigid needle shield 2006. A plurality of outer protrusions 2018 may be provided on the outer surface of the outer wall 2010, to facilitate fixed engagement of the needle shield remover 2000 within a removable cap of an automatic injection device to provide a gripping surface to the removable cap. In this manner the removable cap cooperatively engages with the gripping surface defined by the plurality of protrusions 2018 and the plurality of valleys to reliably remove the rigid needle shield 2006 and the soft needle shield 2004 from the syringe or the automatic injection device.

When the needle shield remover 2000 is pulled away from the syringe body 2002 (as shown by arrow R), the protrusions 2014 exert force against the periphery 2016 of the rigid needle shield 2006, thereby pulling the rigid needle shield 2006 and the soft needle shield 2004 away from the syringe body 2002 and exposing the needle of the syringe 2002 for use. It is noted that the protrusions 2014 may also be configured to fit within the apertures 2008 of the rigid needle shield 2006, or to otherwise contact the rigid needle shield 2006 (e.g., to fit within corresponding recesses formed in the rigid needle shield 2006).

Figure 21:
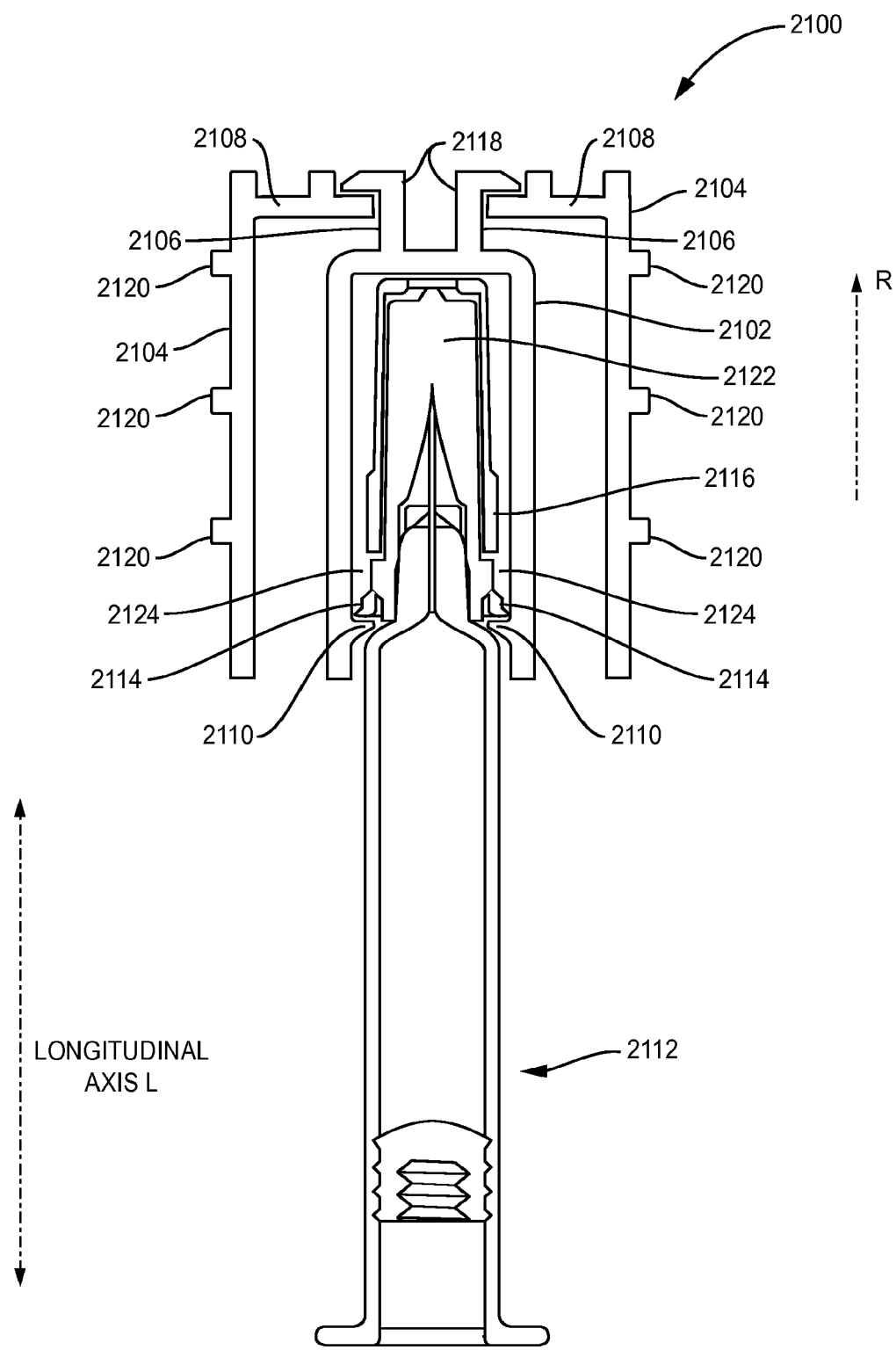
FIG. 21 illustrates a cross-sectional view of another exemplary needle shield remover bisected along the longitudinal axis L.

FIG. 21 illustrates a cross-sectional view of another exemplary needle shield remover 2100 bisected along the longitudinal axis L. In this embodiment, the needle shield remover 2100 includes an inner (first) wall 2102 which is positioned coaxially within an outer (second) wall 2104, and which is coupled to the outer wall 2104 by a hollow projection 2106 extending through an aperture formed in a base wall 2108 that is joined at its periphery to the outer wall 2104 (or formed integrally therewith). Similar to the embodiment shown and discussed above in connection with FIG. 20, the inner wall 2102 includes one or more protrusions 2110 extending therefrom which are biased in a gap formed between the syringe body 2112 and the lower periphery 2114 of the rigid needle shield 2116. The inner wall 2102 may be fixedly or rotatably coupled to the outer wall 2104. One or more protrusions 2118, for example a flange or collar, may be formed at a base end of the hollow projection 2106, so as to couple the base wall 2108 and the outer wall 2104. The inner wall 2102 and the outer wall 2104 may have a circular cross section, an elongated cross section, square cross section, rectangular cross section or any other suitable cross section. The outer wall 2104 may be fixedly coupled to inner surfaces of a removable cap of an automatic injection device, and, as shown in FIG. 21, may include one or more protrusions 2120 to facilitate such coupling and to provide a gripping surface for the removable cap. The protrusions may be rings, collars, flanges or other type of protrusion.

When the outer wall 2104 is pulled away from the syringe body 2112 (as indicated by arrow R), it pulls the inner wall 2102 away from the syringe body 2112, thereby causing the protrusions 2110 to exert force against the lower periphery 2114 of the rigid needle shield 2116 and to pull the rigid needle shield 2116 and the soft needle shield 2122 away from the syringe 2112 to expose the needle for use. As with prior embodiments, it is noted that the protrusions 2110 may be positioned at other locations, e.g., they may be positioned to extend into the apertures 2124 in the rigid needle shield 2116 or to contact other locations (e.g., corresponding recesses) on the rigid needle shield 2116.

Figure 22:
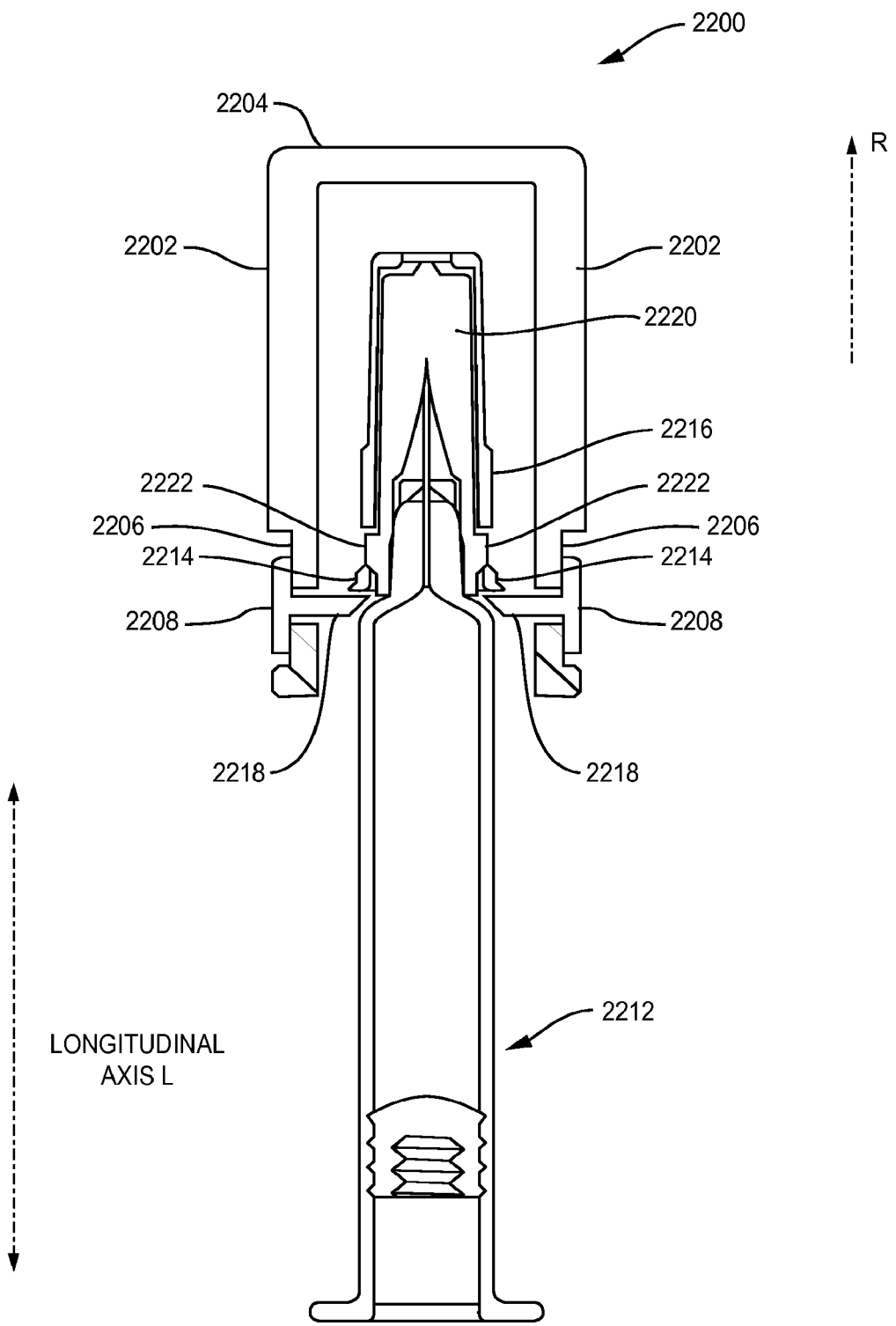
FIG. 22 illustrates a cross-sectional view of another exemplary needle shield remover bisected along the longitudinal axis L.

FIG. 22 illustrates a cross-sectional view of an exemplary needle shield remover 2200 bisected along the longitudinal axis L. The needle shield remover 2200 includes an outer wall 2202 that depends from and is connected to the periphery of a base wall 2204 (or, formed integrally therewith). As mentioned in connection with earlier embodiments, the needle shield remover 2200 may have any shape (e.g., cylindrical or other shape). An annular recess 2206 with an annular opening or a plurality of apertures radially spaced circumferentially about the annular recess is provided along one end of the outer wall 2202, and receives removal element 2208, for example, an annular washer, ring or pins having one or more protrusions 2218 extending through corresponding apertures formed in the recess 2206. Ends of the protrusions 2218 are positioned in a gap formed between the syringe body 2212 and the lower periphery 2214 of the rigid needle shield 2216. The needle shield remover 2200 may be fixedly coupled to inner surfaces of a removable cap of an automatic injection device.

When the needle shield remover 2200 is pulled away from the syringe 2212 (as indicated by arrow R), the protrusions 2218 exert force against the lower periphery 2214 of the rigid needle shield 2216 and pull the rigid needle shield 2216 and the soft needle shield 2220 away from the syringe 2212, thereby exposing the needle for use. It is noted that the removal element 2208 may be positioned so that the protrusions contact other locations, e.g., they may be positioned to extend into the apertures 2222 of the rigid needle shield 2216 or contact other locations of the rigid needle shield 2216 (e.g., they may contact corresponding recesses formed in the rigid needle shield 2216).

Figure 23:
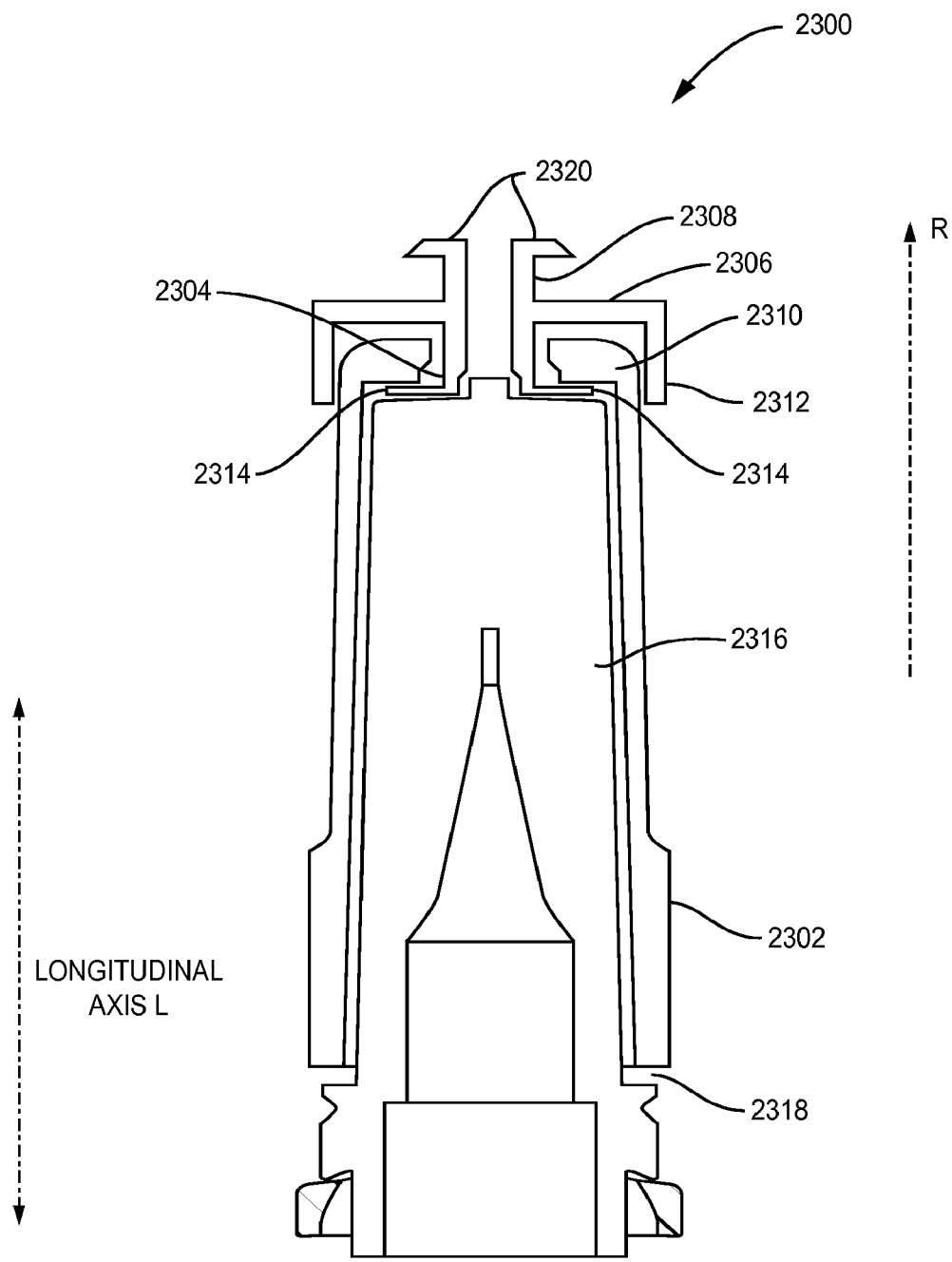
FIG. 23 illustrates a cross-sectional view of another exemplary needle shield remover bisected along the longitudinal axis L.

FIG. 23 illustrates a cross-sectional view of an exemplary needle shield remover 2300 bisected along the longitudinal axis L. The needle shield remover 2300 includes a modified rigid needle shield 2302 having a top aperture 2304, and a captive component 2306 which is coupled to the rigid needle shield 2302. The captive component 2306 includes a hollow axle 2308 that extends through the aperture 2304. Shoulders 2310 of the rigid needle shield 2302 are captured between a peripheral wall 2312 of the captive component 2306 and a transverse annular wall 2314 formed at a lower end of the axle 2308 and positioned between the shoulders 2310 and the soft needle shield 2316. Portions of the soft needle shield 2316 extend through apertures 2318 formed in the rigid needle shield 2302. Protrusions 2320 are provided at a base end of the axle 2308 for coupling (e.g., by way of snap fit) the captive component 2306 to a removable cap of an automatic injection device. When the captive component 2306 is pulled away from a syringe (as indicated by arrow R), the transverse annular wall 2314 exerts force against the shoulders 2310, thereby pulling the rigid needle shield 2302 and the soft needle shield 2316 away from a syringe and exposing the needle for use.

Figure 24:
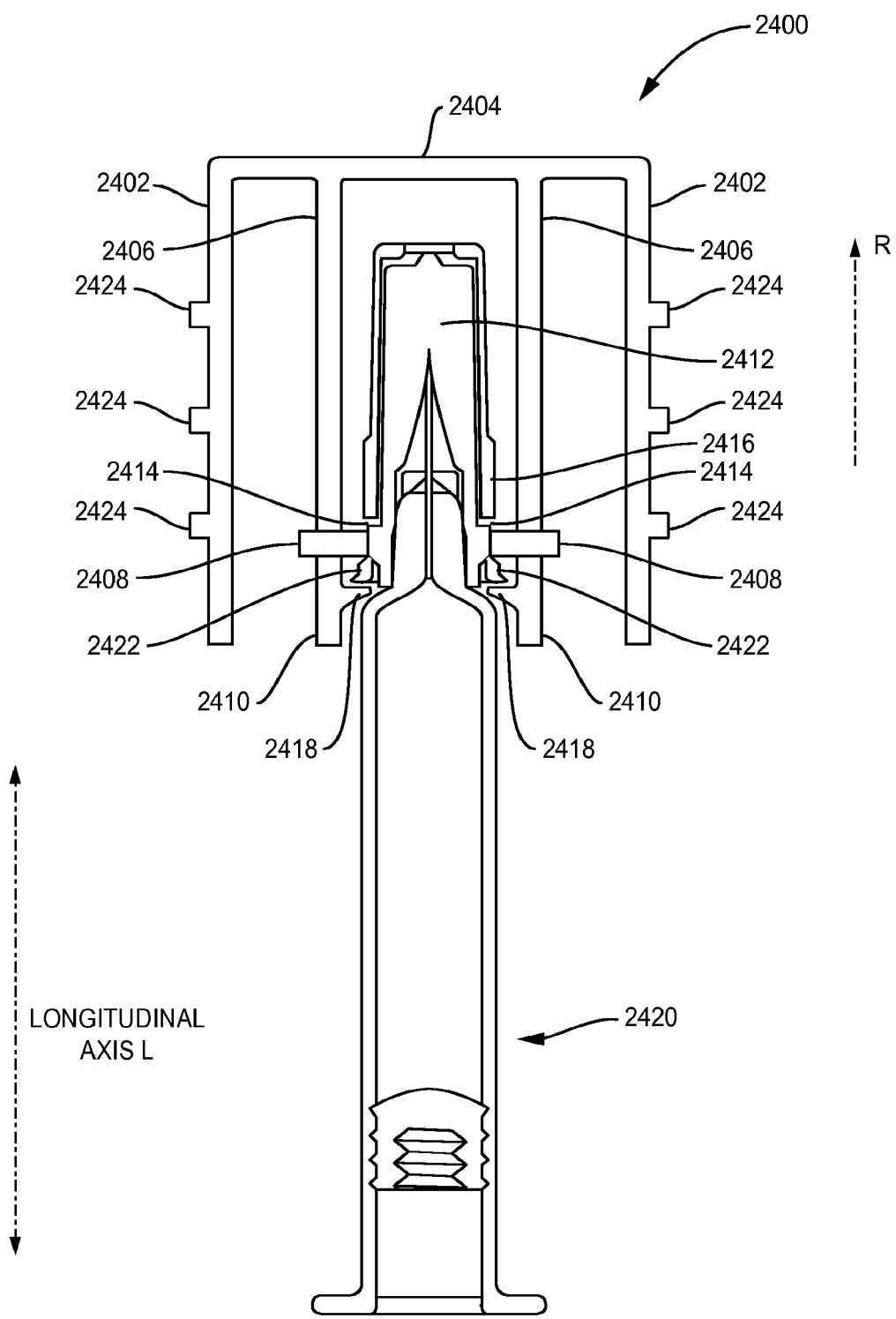
FIG. 24 illustrates a cross-sectional view of another exemplary needle shield remover bisected along the longitudinal axis L.

FIG. 24 illustrates a cross-sectional view of an exemplary needle shield remover 2400 bisected along the longitudinal axis L. The needle shield remover 2400 includes an outer wall 2402 extending from and connected to (or formed integrally with) a base wall 2404, and an inner wall 2406 extending from and connected to (or formed integrally with) the base wall 2404. The outer wall 2402 and the inner wall 2406 may be annularly aligned about a central longitudinal axis of the syringe. The outer wall 2402 and the inner wall 2406 may have a circular cross section, an elongated cross section, square cross section, rectangular cross section or any other suitable cross section.

A collar or spring clip 2408 extends through apertures formed in one end 2410 of the inner wall 2406, and contact the soft needle shield 2412 through the apertures 2414 of the rigid needle shield 2416. One or more protrusions 2418 are formed at the lower end 2410 of the inner wall 2406 and are positioned in a gap formed between the syringe body 2420 and the lower periphery 2422 of the rigid needle shield 2416. The collar/spring clip 2408 stabilizes the protrusions 2418 to prevent them from creeping out of the gap between the syringe body 2420 and the lower periphery 2422 of the rigid needle shield 2416. It is noted that the outer wall 2402 may be fixedly coupled to inner surfaces of a removable cap of an automatic injection device, and, as shown in FIG. 24, may include one or more protrusions 2424 to facilitate such coupling and to provide a gripping surface for the removable cap. The protrusions may be rings, collars, flanges or other type of protrusion.

When the needle shield remover 2400 is pulled away from the syringe 2420 (as indicated by arrow R), the collar 2408 and the protrusions 2418 exert force against the rigid needle shield 2416, thereby pulling the rigid needle shield 2416 and the soft needle shield 2412 away from the syringe 2420 and exposing the needle for use. It is noted that the collar/spring clip 2408, and/or the protrusions 2418, may be positioned to contact other locations of the rigid needle shield 2416 and/or the soft needle shield 2412. The needle shield remover 2400 may be fixedly coupled to inner surfaces of a removable cap of an automatic injection device.

It is noted that, in each of the embodiments discussed herein, the various protrusions which contact the rigid needle shield to remove it from the syringe may be permanently attached to the rigid needle shield, e.g., by way of gluing/epoxy. Of course, such a feature is entirely optional, and the protrusions need not be permanently attached to the rigid needle shield.

VIII. Exemplary Methods of Assembling and Using Automatic Injection Devices

Exemplary needle shield removers are configured and designed for quick, easy and reliable engagement to both a distal cap of an automatic injection device and to one or more needle shields covering an injection needle of the device. One or more exemplary methods may be used to assemble an exemplary needle shield remover with the other components of the device.

In an exemplary method, an exemplary needle shield remover may be assembled with a syringe after the syringe has been inserted into the housing of the device.

In another exemplary method, an exemplary needle shield remover—that is provided as a separate component from a distal cap and from a needle shield—may be assembled with a syringe prior to insertion of the syringe into the housing of the device. The ability to assemble the exemplary needle shield remover with the syringe outside the device housing allows visual inspection of the assembly process to ensure that the needle shield remover is correctly and reliably engaged with the needle shield on the syringe before the syringe and needle shield remover assembly is inserted into the device housing. Thus, assembly of the exemplary needle shield remover in the automatic injection device allows one to be certain that, when the syringe assembly is inserted into the device housing, the needle shield remover is engaged reliably and consistently with the needle shield. This resolves the issue of component tolerance and unreliable positioning of needle shield removal mechanisms in conventional automatic injection devices.

Figure 25:
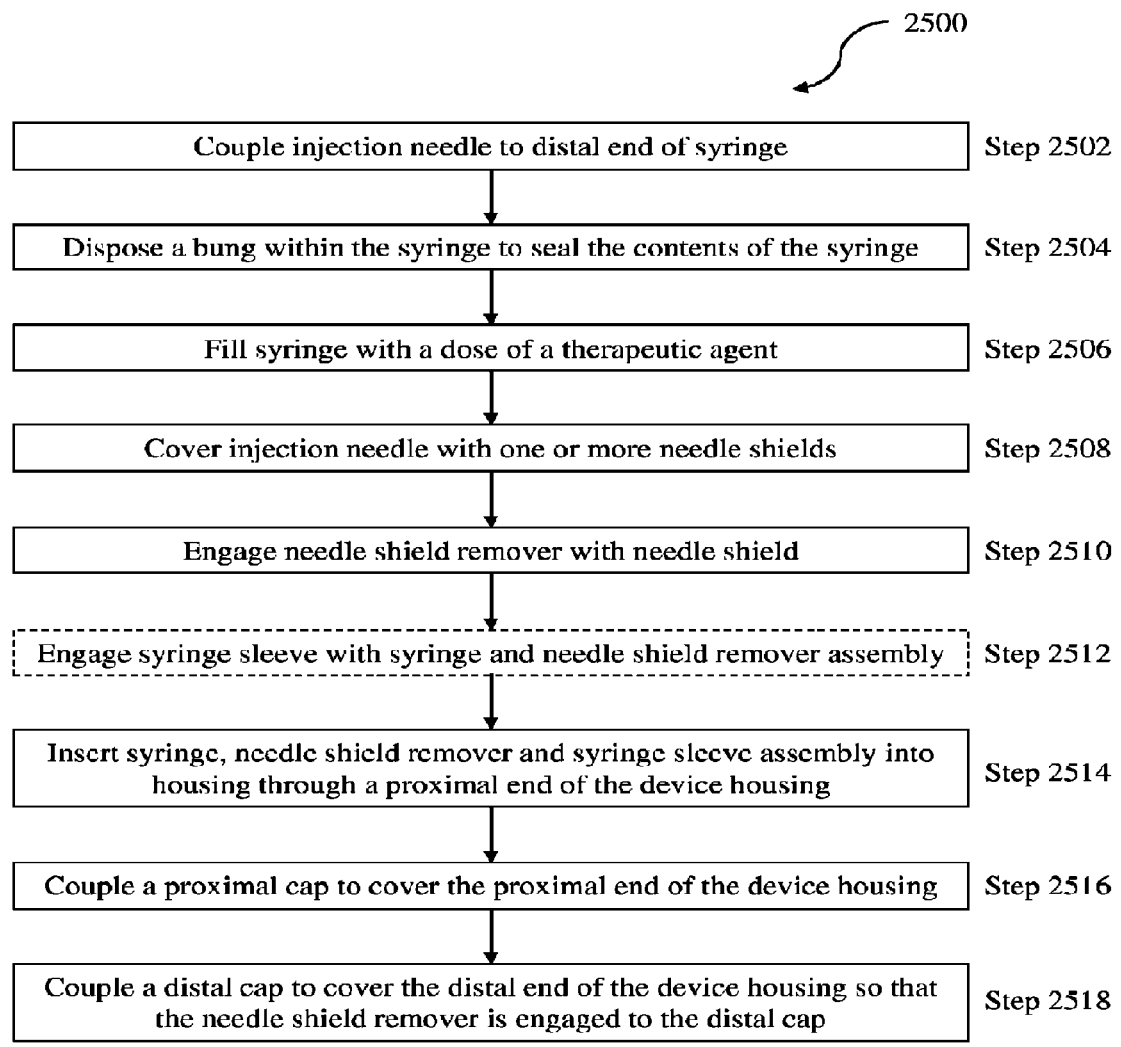
FIG. 25 is a flowchart of an exemplary method for assembling an exemplary needle shield remover with a syringe and a distal cap of an automatic injection device, in which the needle shield remover is assembled with a syringe prior to insertion of the syringe into the housing of the device.

FIG. 25 is a flowchart of an exemplary method 2500 for assembling an exemplary needle shield remover with a syringe and a distal cap of an automatic injection device, in which the needle shield remover is assembled with the syringe prior to insertion of the syringe into the housing of an automatic injection device.

In step 2502, a suitable injection needle may be coupled to a distal end of the syringe. In step 2504, a bung may be disposed within the syringe to seal the contents of the syringe. In step 2506, the syringe may be filled with a dose of a therapeutic agent. In step 2508, the injection needle may be covered by one or more soft needle shields and/or one or more rigid needle shields.

In step 2510, a needle shield remover may be engaged to the rigid needle shield attached to the syringe prior to insertion of the syringe into the housing of the device. The ability to assemble the exemplary needle shield remover to the syringe outside the device housing allows visual inspection of the assembly process to ensure that the needle shield remover reliably engages the needle shield on the syringe before the syringe assembly is inserted into the device housing.

In an exemplary embodiment, one or more inwardly-projecting shield engagement mechanisms of the needle shield remover may be engaged to a gap formed between the proximal end of the rigid needle shield and the syringe body. In an exemplary embodiment, as the needle shield remover is positioned surrounding the rigid needle shield, the shield engagement mechanisms may snap into place at the gap and may not be disengaged during the assembly process. When the inwardly-projecting shield engagement mechanisms snap into place at the gap, there may be a decrease in the force experienced against insertion of the needle shield remover over the rigid needle shield. In an exemplary embodiment, this decrease in the force may be sensed by a user or automatically by an assembly machine to determine that the inwardly-projecting shield engagement mechanisms have been successfully engaged to the needle shield at the gap. In an exemplary embodiment, positioning of the shield engagement components at the gap may emit an audible "click" sound that provides an audible indication that the needle shield remover has been successfully engaged with the rigid needle shield.

In another exemplary embodiment, one or more inwardly-projecting shield engagement mechanisms of the needle shield remover may be engaged to one or more apertures defined in a rigid needle shield. In another exemplary embodiment, one or more inwardly-projecting shield engagement mechanisms of the needle shield remover may be engaged to one or more ridged portions in the exterior surface of the rigid needle shield.

In step 2512, in an exemplary embodiment, a syringe sleeve may be engaged with the syringe and needle shield remover. The syringe sleeve may be maintained in a substantially fixed axial orientation relative to the device housing. The syringe sleeve may, in turn, maintain the needle shield remover in a substantially fixed axial orientation relative to the syringe sleeve. This assembly aligns the cutout portions of the needle shield remover with the inspection window or inspection aperture of the syringe sleeve and with the inspection window or inspection aperture of the device housing. This allows a user to view the contents of the syringe and/or an end-of-injection indicator through the inspection window or inspection aperture of the device housing.

In another exemplary embodiment, a syringe sleeve may be absent in the automatic injection device and step 2512 may be skipped. In this exemplary embodiment, the axial orientation of the needle shield remover may be manually or automatically adjusted relative to the device housing so that the cutout portions of the needle shield remover are aligned with the inspection window or inspection aperture of the device housing. This allows a user to view the contents of the syringe and/or to view an indicator through the inspection window or inspection aperture of the device housing.

In step 2514, the syringe, needle shield remover and syringe sleeve assembly may be inserted into the device housing through a proximal end of the device housing.

In step 2516, a proximal cap may be coupled to the proximal end of the device housing to seal the proximal end.

In step 2518, a distal cap may be coupled to the distal end of the device housing so that the distal cap is engaged to both the distal end of the housing and to the needle shield remover in one step. In an exemplary embodiment, as the distal cap is inserted over the needle shield remover disposed at the distal end of the device housing, one or more cap engagement mechanisms of the needle shield remover may fit within a central aperture provided in the distal cap. One or more inwardly-projecting stop portions (e.g., flanges or raised edges) provided in the central aperture of the distal cap may snap into place within a gap formed under the cap engagement mechanisms. When the cap engagement mechanisms snap into place at the gap over the inwardly-projecting stop portions in the central aperture of the distal cap, there may be a decrease in the force experienced against insertion of the distal cap over the needle shield remover. In an exemplary embodiment, this decrease in the force may be sensed by a user or automatically by an assembly machine to determine that the cap engagement mechanisms have been successfully engaged to the distal cap. In an exemplary embodiment, the engagement of the cap engagement mechanisms with the distal cap may emit an audible "click" sound that provides an audible indication that the needle shield remover has been successfully engaged with the distal cap.

Figure 26:
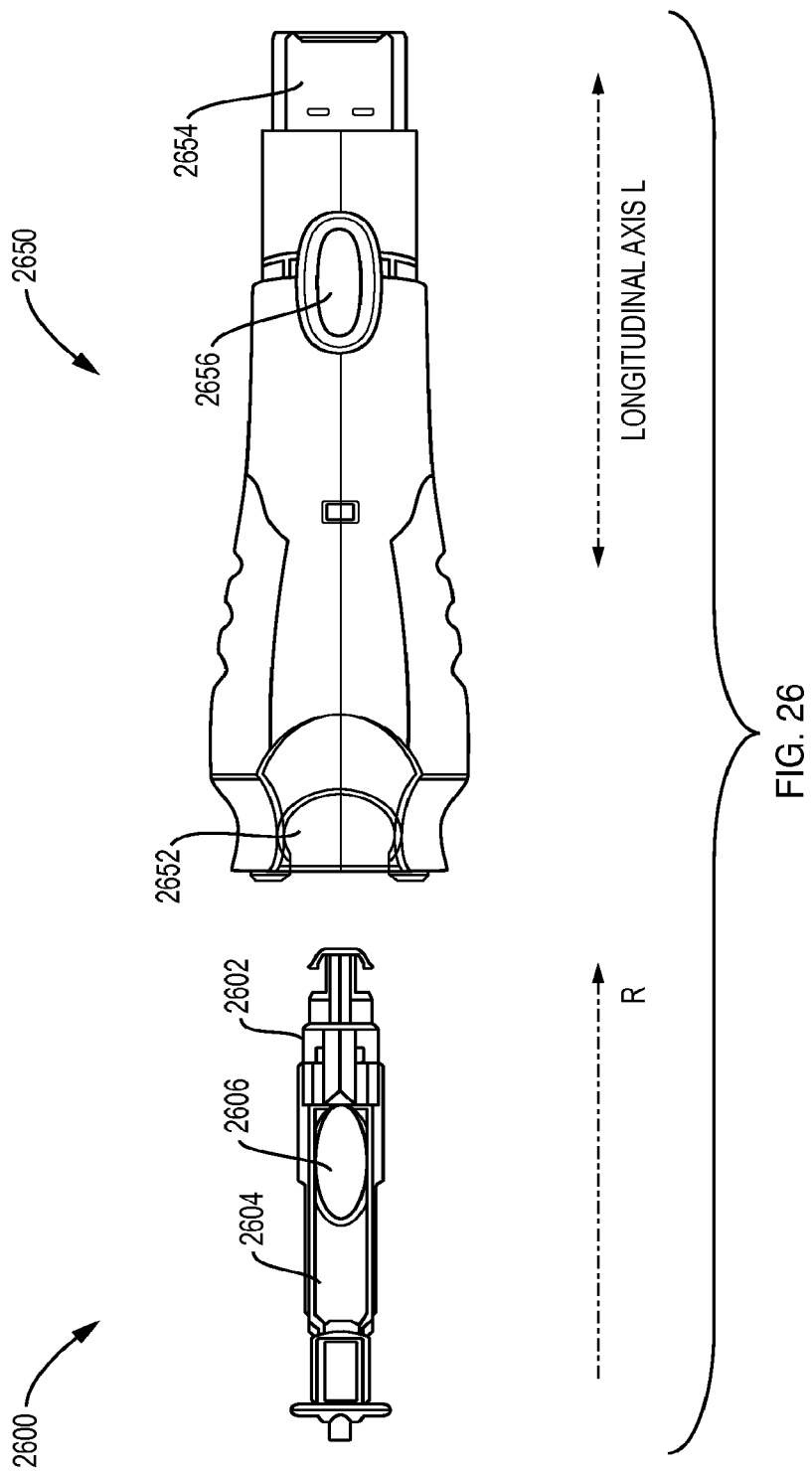
FIG. 26 illustrates a device view of the exemplary method of FIG. 25 by which an exemplary automatic injection device may be assembled.

FIG. 26 illustrates a device view of the exemplary method 2500 of FIG. 25 by which an exemplary automatic injection device may be assembled. A syringe assembly 2600 may include a syringe, a needle shield remover 2602 coupled to the syringe, and a syringe sleeve 2604 coupled to the syringe and the needle shield remover 2602. A side wall of the syringe sleeve 2604 may define or include a transparent inspection window or inspection aperture 2606. The syringe assembly 2600 may be assembled before its insertion into a housing 2650 of the automatic injection device. The housing 2650 may have a proximal end 2652 that is open during assembly and that may be covered by a proximal cap (not pictured) after the syringe assembly is inserted into the housing 2650. The housing 2650 may have a distal end 2654 that is open during assembly and that may be covered by a distal cap (not pictured) after the syringe assembly is inserted into the housing 2650. A side wall of the housing 2650 may define or include a transparent inspection window or inspection aperture 2656 through which a user may view the contents of the syringe.

The assembled syringe 2600 may be inserted into the device housing 2650 at the proximal end 2652 in the direction represented by arrow R, so that the distal end of the needle shield remover 2602 is disposed at the distal end 2654 of the device housing 2650. Once the syringe assembly 2600 is inserted in the housing 2650, the inspection window or inspection aperture 2656 of the housing 2650 is aligned with the inspection window or inspection aperture 2606 of the syringe sleeve 2604. The transparent inspection window or inspection aperture 2606 of the syringe sleeve 2604 is, in turn, aligned with a cutout portion on the needle shield remover 2602, thus allowing a user of the device to view the contents of the syringe and/or to view an end-of-injection indicator through the inspection window or inspection aperture 2656 of the device housing 2650.

Figure 27:
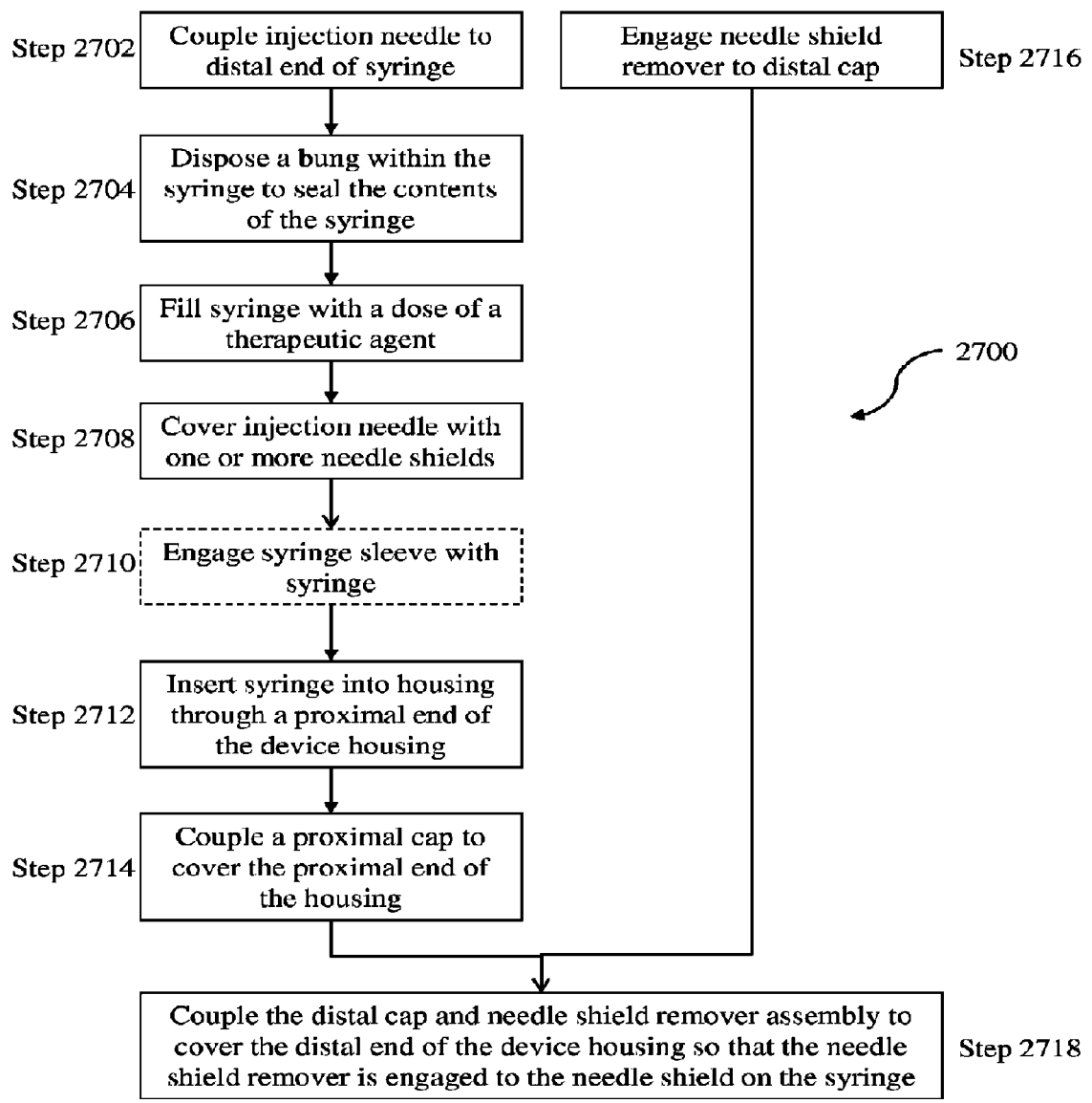
FIG. 27 is a flowchart of an exemplary method for assembling an exemplary needle shield remover with a syringe and a distal cap of an automatic injection device, in which the needle shield remover is assembled with a syringe after insertion of the syringe into the housing of the device.

FIG. 27 is a flowchart of an exemplary method 2700 for assembling an exemplary needle shield remover with a syringe and a distal cap of an automatic injection device, in which the needle shield remover is assembled with the syringe after insertion of the syringe into the housing of the device.

In step 2702, a suitable injection needle may be coupled to a distal end of the syringe. In step 2704, a bung may be disposed within the syringe to seal the contents of the syringe. In step 2706, the syringe may be filled with a dose of a therapeutic agent. In step 2708, the injection needle may be covered by one or more soft needle shields and/or one or more rigid needle shields.

In step 2710, in an exemplary embodiment, a syringe sleeve may be engaged to the syringe. The syringe sleeve may be maintained in a substantially fixed axial orientation relative to the device housing. The syringe sleeve may, in turn, maintain a needle shield remover in a substantially fixed axial orientation relative to the syringe sleeve. This assembly aligns the cutout portions of the needle shield remover with the inspection window or inspection aperture of the syringe sleeve and with the inspection window or inspection aperture of the device housing. This allows a user to view the contents of the syringe and/or to view an end-of-injection indicator through the inspection window or inspection aperture of the device housing.

In another exemplary embodiment, a syringe sleeve may be absent in the automatic injection device and step 2710 may be skipped. In this exemplary embodiment, the axial orientation of the needle shield remover may be manually or automatically adjusted relative to the device housing so that the cutout portions of the needle shield remover are aligned with the inspection window or inspection aperture of the device housing. This allows a user to view the contents of the syringe and/or to view an end-of-injection indicator through the inspection window or inspection aperture of the device housing.

In step 2712, the syringe and syringe sleeve assembly may be inserted into the device housing through a proximal end of the device housing.

In step 2714, a proximal cap may be coupled to the proximal end of the device housing to seal the proximal end.

In step 2716, a needle shield remover may be engaged to a distal cap of the automatic injection device. In an exemplary embodiment, as the distal cap is inserted over the needle shield remover, the distal end of the needle shield remover may fit within a central aperture provided in the distal cap. One or more inwardly-projecting stop portions (e.g., flanges or raised edges) provided in the central aperture of the distal cap may snap into place within a gap formed under the cap engagement mechanisms provided at the distal end of the needle shield remover. When the cap engagement mechanisms snap into place at the gap over the inwardly-projecting stop portions in the central aperture of the distal cap, there may be a decrease in the force experienced against insertion of the distal cap over the needle shield remover. In an exemplary embodiment, this decrease in the force may be sensed by a user or automatically by an assembly machine to determine that the cap engagement mechanisms have been successfully engaged to the distal cap. In an exemplary embodiment, the engagement of the cap engagement mechanisms with the distal cap may emit an audible "click" sound that provides an audible indication that the needle shield remover has been successfully engaged with the distal cap.

In step 2718, the distal cap and needle shield assembly may be coupled to the distal end of the device housing to cover the distal end, so that the needle shield remover is engaged to the needle shield on the syringe. In an exemplary embodiment, one or more inwardly-projecting shield engagement mechanisms of the needle shield remover are engaged to a gap formed between the rigid needle shield and the syringe body. In an exemplary embodiment, as the needle shield remover is inserted over the rigid needle shield, the inwardly-projecting shield engagement mechanisms may snap into place at the gap and may not be disengaged during the assembly process. When the inwardly-projecting shield engagement mechanisms snap into place at the gap, there may be a decrease in the force experienced against insertion of the needle shield remover over the rigid needle shield. In an exemplary embodiment, this decrease in the force may be sensed by a user or automatically by an assembly machine to determine that the inwardly-projecting shield engagement mechanisms have been successfully engaged to the needle shield at the gap. In an exemplary embodiment, positioning of the shield engagement components at the gap may emit an audible "click" sound that provides an audible indication that the needle shield remover has been successfully engaged with the rigid needle shield.

In another exemplary embodiment, one or more inwardly-projecting shield engagement mechanisms of the needle shield remover may be engaged to one or more apertures defined in a rigid needle shield. In another exemplary embodiment, one or more inwardly-projecting shield engagement mechanisms of the needle shield remover may engaged to one or more ridged portions in the exterior surface of the rigid needle shield.

Figure 28:
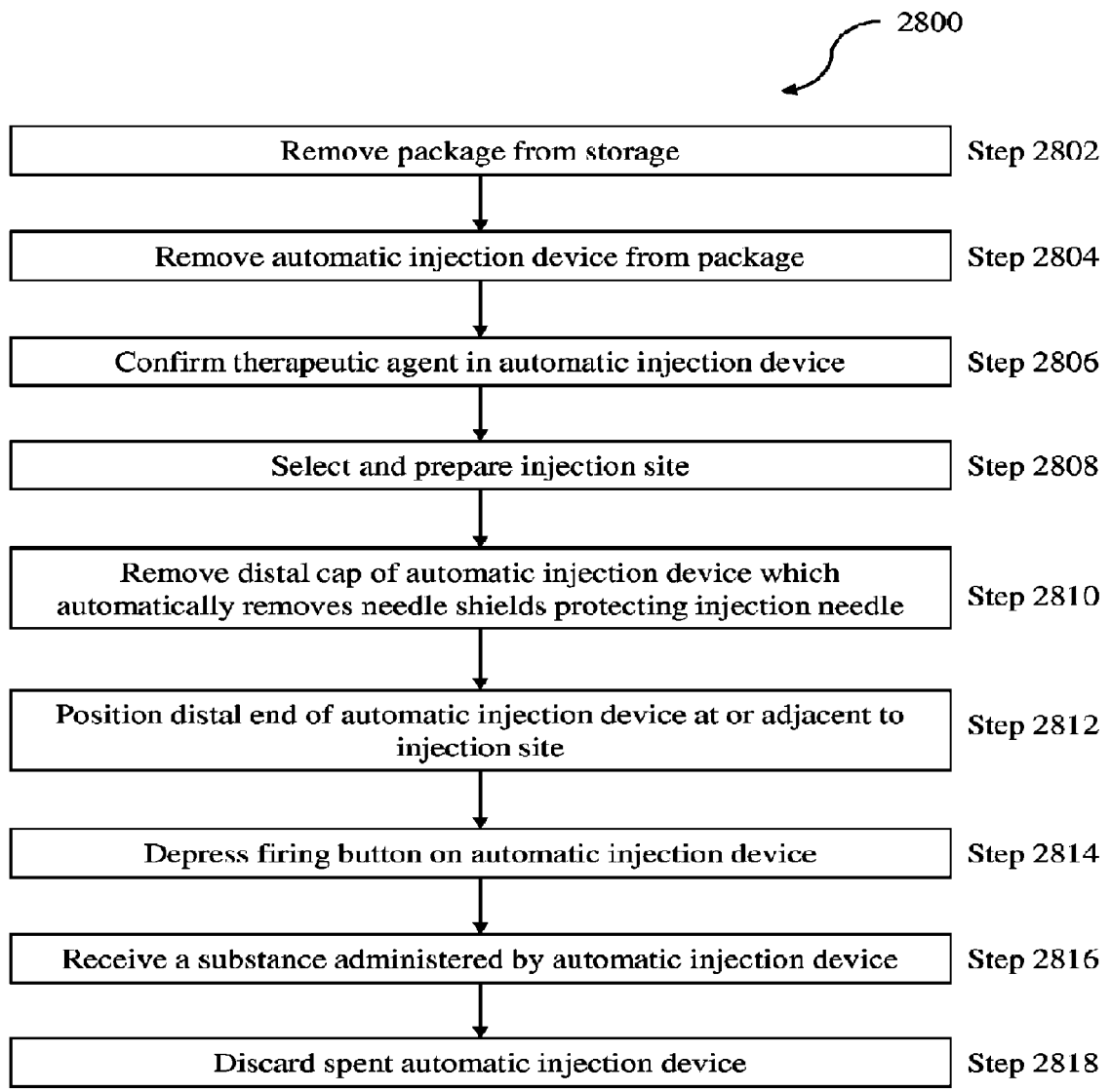
FIG. 28 is a flowchart of an exemplary method for using an exemplary automatic injection device to administer an injection.

FIG. 28 is a flowchart of an exemplary method 2800 for using an exemplary automatic injection device to administer an injection. An exemplary automatic injection device may be packaged and pre-filled with a therapeutic agent and may be stored in refrigerated storage before use. In step 2802, the packaged automatic injection device may be removed from storage. In step 2804, the automatic injection device may be removed from its packaging and any over-wrap and warmed to room temperature, for example, by leaving the device outside the packaging at room temperature or by warming the device. In step 2806, the user may view the contents of the device through a transparent inspection window or inspection aperture provided in the device housing to ensure that the device contains a volume of the therapeutic agent and to confirm the clarity of the therapeutic agent, if necessary. In step 2808, the injection site on a patient's body may be selected and prepared for the delivery of the therapeutic agent.

In step 2810, the user of the automatic injection device may remove the distal cap of the automatic injection device that protects the injection needle and any needle shields protecting the needle. A needle shield remover provided in the device automatically removes all of the needle shields when the user removes the distal cap. In step 2812, the user of the device may position the automatic injection device so that the distal end of the device is positioned at or adjacent to the injection site on the patient's body. In step 2814, a firing button on the device may be depressed or otherwise activated to cause the device to perform an injection at the injection site. In step 2816, the injection site on the patient's body may receive a therapeutically effective dose of the therapeutic agent administered by the device. In an exemplary embodiment, activating the firing button may cause a syringe to advance within and relative to the device housing so that the injection needle protrudes from an open distal end of the housing, and may cause a bung to move within the syringe to expel the therapeutic agent out of the syringe through the injection needle and into the injection site.

In step 2818, after administration of the therapeutic agent, the automatic injection device may be removed from the injection site on the patient's body and discarded in an appropriate manner.

IX. Incorporation by Reference

The entire contents of all references, including patents and patent applications, cited throughout this application are hereby incorporated herein by reference in their entirety. The appropriate components and methods of those references may be selected for the invention and embodiments thereof. Still further, the components and methods identified in the Background section are integral to this disclosure and may be used in conjunction with or substituted for components and methods described elsewhere in the disclosure within the scope of the invention.

X. Equivalents

In describing exemplary embodiments, specific terminology is used for the sake of clarity. For purposes of description, each specific term is intended to, at least, include all technical and functional equivalents that operate in a similar manner to accomplish a similar purpose. Additionally, in some instances where a particular exemplary embodiment includes a plurality of system elements or method steps, those elements or steps may be replaced with a single element or step. Likewise, a single element or step may be replaced with a plurality of elements or steps that serve the same purpose. Further, where parameters for various properties are specified herein for exemplary embodiments, those parameters may be adjusted up or down by 1/20th, 1/10th, 1/5th, 1/3rd, 1/2nd, and the like, or by rounded-off approximations thereof, unless otherwise specified. Moreover, while exemplary embodiments have been shown and described with references to particular embodiments thereof, those of ordinary skill in the art will understand that various substitutions and alterations in form and details may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than shown.

What is claimed is:

1. A needle shield remover for removing a needle shield from a syringe, comprising:
a cap having an open end and a closed end with a centrally located aperture,
a tubular needle shield remover disposed within the cap for removing a needle shield from a syringe, the tubular needle shield remover having a proximal tubular portion having a first outer diameter and a distal tubular portion having a second outer diameter less than the first outer diameter,
a platform structure projecting longitudinally from the distal tubular portion of the tubular needle shield remover along a longitudinal axis toward the aperture, and
a cap engagement mechanism projecting radially outwardly from the platform structure to cooperatively engage the tubular needle shield remover with the cap via the aperture.

2. The needle shield remover of claim 1, wherein the platform structure allows the cap and the tubular needle shield remover to move in an axial direction relative to each other.

3. The needle shield remover of claim 1, wherein the cap includes an inwardly-projecting stop portion provided in the aperture.

4. The needle shield remover of claim 1, wherein the platform structure defines a gap extending longitudinally between the cap engagement mechanism and the distal tubular portion of the tubular needle shield remover.

5. The needle shield remover of claim 4, wherein an inwardly-projecting stop portion of the cap is accommodated in the gap to define one of an upper or lower limit of axial movement between the cap and the tubular needle shield remover.

6. The needle shield remover of claim 1, wherein the cap and the tubular needle shield remover form a single assembly that is pre-assembled before the tubular needle shield remover is engaged with the needle shield.

7. The needle shield remover of claim 1, wherein the cap is a tubular cap.

8. The needle shield remover of claim 1, wherein the cap and the tubular needle shield remover slide in an axial direction relative to each other during attachment to the needle shield.

9. The needle shield remover of claim 1, wherein the cap and the tubular needle shield remover form a single assembly, and the single assembly is engaged to the needle shield after the syringe is loaded into an automatic injection device.

10. The needle shield remover of claim 1, wherein the platform structure includes a first longitudinally projecting portion, a second longitudinally projecting portion and a transverse portion at a distal end of the platform structure extending between the first longitudinally projecting portion and the second longitudinally projecting portion.

11. The needle shield remover of claim 10, wherein the cap engagement mechanism is cooperatively engaged with the transverse portion.

12. The needle shield remover of claim 1, wherein the proximal tubular portion of the tubular needle shield remover includes two needle shield engagement mechanisms engageable with the needle shield of the syringe.

13. The needle shield remover of claim 12, wherein the two needle shield engagement mechanisms project inwardly from a side wall of the proximal tubular portion.

14. The needle shield remover of claim 13, wherein each of the needle shield engagement mechanisms include a first inclined wall that extends from the side wall.

15. The needle shield remover of claim 14, wherein each of the two shield engagement mechanisms comprises a second inclined wall coupled to the first inclined wall and extending inwardly into a cavity of the tubular needle shield remover.

16. The needle shield remover of claim 15, further comprising two apertures disposed in a side wall of the proximal portion of the tubular needle shield remover, and wherein each of the two shield engagement mechanisms is provided in a respective one of the two apertures.

17. The needle shield remover of claim 16, further comprising two cutout portions formed in the side wall of the proximal portion of the tubular needle shield remover and circumferentially disposed in an alternating manner with the two apertures about the tubular needle shield remover.

18. An automatic injection device comprising:
a housing,
a syringe slidably disposed in the housing;
a needle shield covering a needle of the syringe; and
a needle shield remover according to claim 1 removably coupled to the housing and the needle shield.

19. The automatic injection device of claim 18, wherein the platform structure allows the cap and the tubular needle shield remover to move in an axial direction relative to each other.

20. The automatic injection device of claim 18, wherein the platform structure defines a gap extending longitudinally between the cap engagement mechanism and the distal tubular portion of the tubular needle shield remover.

21. The automatic injection device of claim 20, wherein an inwardly-projecting stop portion of the cap is accommodated in the gap to define one of an upper or lower limit of axial movement between the cap and the tubular needle shield remover.

22. The automatic injection device of claim 18, wherein the cap and the tubular needle shield remover slide in an axial direction relative to each other during attachment to the needle shield.

23. The automatic injection device of claim 18, wherein the platform structure includes a first longitudinally projecting portion, a second longitudinally projecting portion and a transverse portion at a distal end of the platform structure extending between the first longitudinally projecting portion and the second longitudinally projecting portion.

24. The automatic injection device of claim 23, wherein the cap engagement mechanism is cooperatively engaged with the transverse portion.

25. The automatic injection device of claim 18, wherein the proximal tubular portion of the tubular needle shield remover includes two needle shield engagement mechanisms engageable with the needle shield of the syringe.

26. The automatic injection device of claim 25, wherein the two needle shield engagement mechanisms project inwardly from a side wall of the proximal tubular portion.

27. The automatic injection device of claim 26, wherein each of the needle shield engagement mechanisms include a first inclined wall that extends from the side wall.

28. The automatic injection device of claim 27, wherein each of the two shield engagement mechanisms comprises a second inclined wall coupled to the first inclined wall and extending inwardly into a cavity of the tubular needle shield remover.

29. The automatic injection device of claim 28, further comprising two apertures disposed in a side wall of the proximal portion of the tubular needle shield remover, and wherein each of the two shield engagement mechanisms is provided in a respective one of the two apertures.

30. The automatic injection device of claim 29, further comprising two cutout portions formed in the side wall of the proximal portion of the tubular needle shield remover and circumferentially disposed in an alternating manner with the two apertures about the tubular needle shield remover.

* * * * *